US011791016B2

(12) United States Patent
Murray et al.

(10) Patent No.: US 11,791,016 B2
(45) Date of Patent: Oct. 17, 2023

(54) METHODS AND SYSTEMS FOR COMPUTER-GENERATED PREDICTIVE APPLICATION OF NEUROIMAGING AND GENE EXPRESSION MAPPING DATA

(71) Applicants: NEUMORA THERAPEUTICS, INC., Brisbane, CA (US); Yale University, New Haven, CT (US)

(72) Inventors: John D. Murray, New Haven, CT (US); Alan Anticevic, New Haven, CT (US); William J. Martin, San Francisco, CA (US)

(73) Assignees: Neumora Therapeutics, Inc., Brisbane, CA (US); Yale University, New Haven, CT (US)

( * ) Notice: Subject to any disclaimer, the term of this patent is extended or adjusted under 35 U.S.C. 154(b) by 970 days.

(21) Appl. No.: 16/150,137

(22) Filed: Oct. 2, 2018

(65) Prior Publication Data
US 2019/0355439 A1 Nov. 21, 2019

Related U.S. Application Data

(60) Provisional application No. 62/567,087, filed on Oct. 2, 2017.

(51) Int. Cl.
*G16B 20/00* (2019.01)
*G16H 50/20* (2018.01)
*G16H 20/10* (2018.01)
*G16B 25/10* (2019.01)
*G16B 40/00* (2019.01)
G16H 30/20 (2018.01)

(52) U.S. Cl.
CPC .............. *G16B 20/00* (2019.02); *G16B 25/10* (2019.02); *G16B 40/00* (2019.02); *G16H 20/10* (2018.01); *G16H 50/20* (2018.01); G16H 30/20 (2018.01)

(58) Field of Classification Search
CPC ........ G16B 20/00; G16B 25/10; G16B 40/00; G16H 50/20; G16H 20/10
See application file for complete search history.

(56) References Cited

U.S. PATENT DOCUMENTS

| 9,053,534 B2 | 6/2015 | Ross |
| 9,230,321 B2 | 1/2016 | El-Baz |
| 2008/0241839 A1 | 10/2008 | Potkin |
| 2010/0129818 A1 | 5/2010 | Sadee et al. |
| 2014/0162933 A1 | 6/2014 | Hatchwell et al. |
| 2015/0050215 A1 | 2/2015 | Novak et al. |
| 2015/0299792 A1 | 10/2015 | Gruen |
| 2016/0019693 A1 | 1/2016 | Silbersweig |
| 2016/0035093 A1 | 2/2016 | Kateb et al. |
| 2017/0145511 A1 | 5/2017 | Myers |
| 2018/0094248 A1 | 4/2018 | Oddo |
| 2019/0102511 A1 | 4/2019 | Murray |
| 2019/0272889 A1 | 9/2019 | Murray et al. |
| 2019/0355439 A1 | 11/2019 | Murray |
| 2021/0158892 A1 | 5/2021 | Murray et al. |

OTHER PUBLICATIONS

International Search Report (Application No. PCT/US2018/054009) dated Feb. 4, 2019.
A. Komorowski et al., "Association of Protein Distribution and Gene Expression Revealed by PET and Post-Mortem Quantification in the Serotonergic System of the Human Brain", Cerebral Cortex, vol. 27, No. 1, Nov. 30, 2016 (Nov. 30, 2016), pp. 117-130.
Jingwen Yan et al., "Transcriptome-guided Amyloid Imaging Genetic Analysis Via A Novel Structured Sparse Learning Algorithm", Bioinformatics., vol. 30, No. 17, Sep. 1, 2014 (Sep. 1, 2014), pp. i564-i571.
Written Opinion (Application No. PCT/US2018/054009) dated Feb. 4, 2019.
Jouandet, M.L. et al., "Brainprints: Computer-Generated Two-Dimensional Maps of the Human Cerebral Cortex in vivo," Journal of Cognitive Neuroscience, 1(1):88-117 (1989).
Aritan, S. et al., "Program for generation of three-dimensional finite element mesh from magnetic resonance imaging scans of human limbs," Med. Eng. Phys., 19(8):681-689 (1997).
Camacho, D.L.A. et al., "An improved method for finite element mesh generation of geometrically complex structures with application to the skullbase," J. Biomechanics, 30(10):1067-1070 (1997).
Xu, C. et al., "Reconstruction of the Human Cerebral Cortex from Magnetic Resonance Images," IEEE Transactions on Medical Imaging, 18(6):467-480 (1999).
Lederman, C. et al., "The generation of tetrahedral mesh models for neuroanatomical MRI," Neuroimage, 55(1):153-164 (2011).
Yan, J. et al., "Transcriptome-guided amyloid imaging genetic analysis via a novel structured sparse learning algorithm," Bioinformatics, 30(17): i564-i571, Sep. 1 2014.
Glasser, F.M. et al., "The human Connectome Project's Neuroimaging Approach," Nat. Neurosci. 19(9), pp. 1175-1187, Aug. 26, 2016 (13 pages).
Komorowski, A. et al., "Association of Protein Distribution and Gene Expression Revealed by PET and Post-Mortem Quantification in the Serotonergic System of the Human Brain," Cerebral Cortex, 27(1): 117-130, Nov. 30, 2016.

(Continued)

*Primary Examiner* — Jerry Lin
(74) *Attorney, Agent, or Firm* — NIXON PEABODY LLP

(57) ABSTRACT

The present disclosure relates to computer generated topographies from computer correlations of neurobehavioral phenotype mapping data and gene expression mapping data. Neurobehavioral phenotype mapping data is obtained for a selected phenotype and correlated with gene expression mapping data for one or more genes to define a phenotype-gene pair topography for each phenotype-gene pair. A score for each phenotype-gene pair is determined based on the correlation. The scores are used to identify genes, or drug targets, associated with the respective gene of the respective phenotype-gene pair. Conversely, gene expression mapping data is obtained for a selected gene and correlated with neurobehavioral phenotype mapping data for one or more phenotypes to define a gene-phenotype topography for each gene-phenotype pair. A score for each gene-phenotype pair is determined based on the correlation. The scores are used to identify a phenotype associated with the respective phenotype-gene pair.

25 Claims, 32 Drawing Sheets

(56) References Cited

OTHER PUBLICATIONS

International Search Report and Written Opinion of International Searching Authority for Application No. PCT/ US2018/054009, dated Apr. 11, 2019 (21 pages).
International Preliminary Repor on Patentability in International Application No. PCT/US2018/053984, dated Apr. 7, 2020 (11 pages).
Akbarian et al., The PsychENCODE project, Nature Neuroscience, vol. 18, No. 12, Dec. 2015.
Anticevic A. et al., Comparing surface-based and volume-based analyses of functional neuroimaging data in patients with schizophrenia, Neuroimage, 41(3):835-48, Jul. 1, 2008.
Bain et al., Therapeutic Development in the Absence of Predictive Animal Models of Nervous System Disorders: Proceedings of a Workshop, The National Academic Press (2017).
Baker et al., Disruption of cortical association networks in schizophrenia and psychotic bipolar disorder, JAMA Psychiatry 71:109-18 (2014).
Beliveau et al., A high-resolution in vivo atlas of the human brain's serotonin system, J. Neurosci. (2016).
Bider Jr et al., Mapping anterior temporal lobe language areas with fMRI: a multicenter normative study, Neuroimage, 54:1465-1475 (2011). https://www.ncbi.nlm.nih.gov/pubmed/20884358.
Bizzi A. et al., Presurgical functional MR imaging of language and motor functions: validation with intraoperative mapping, Radiology, 248:579-589 (2008).
Burt et al., Hierarchy of transcriptomic specialization across human cortex captured by structural neuroimaging topography, Nature Neuroscience 21:1251-9 (2018).
Caceres A. et al., Measuring fMRI reliability with the intra-class correlation coefficient, Neuroimage, 45:758-768 (2009).
Dale AM et al., Coritcal surface-based analysis I. Segmentation and surface reconstruction, Neuroimage, 9 (2), 179-194, 4931 (1999).
Dalwaldi et al., Molecular mechanisms of serotonergic action of the HIV-1 antiretroviral efavirenz, Pharmacol Res., 110:10-24 (2016).
Datta et al., Developmental expression patterns of gabaa receptor subunits in layer 3 and 5 pyramidal cells of monkey prefrontal cortex, Cereb. Cortex 25:2295-305 (2015).
Ditman T. et al., An investigation of concurrent ERP and self-paced reading methodologies, Psychophysiology, 44:927-935 (2007).
Drobyshevsky A. et al., A rapid fMRI task battery for mapping of visual, motor, cognitive, and emotional fuction, Neuroimage, 31:732-744 (2006) ("Drobyshevsky").
Drysdale et al., Resting-state connectivity biomarkers define neurophysiological subtypes of depression, Nat. Med. (2016), Epub Ahead of Print.
Egan et al., Randomized crossover study of the histamine H3 inverse agoinst MK-0249 for the treatment of cognitive impairment in patients with schizophrenia, Schizophr. Res., 146(1-3): 224-30 May 2013; doi: 10.1016/j.schres.2013.02.030 (2013).
Fischl B. et al, Cortical surface-based analysis. II: Inflation, flattening, and a surface-based coordinate system, NeuroImage, 9 (2), 195-207 (1999).
Fischl B. et al, Whole brain segmentation: Automated labeling of neuroanatomical structures in the human brain, Neuron, 33 (3), 341-355, 3776 (2002).
Gandal et al., Shared molecular neuropathology across major psychiatric disorders parallels polygenic overlap, Science, 359, 693-697, Feb. 9, 2018.
Gill et al., The role of α5 $GABA_a$ receptor agonists in the treatment of cognitive deficits in schizophrenia, Curr. Pharm. Des., 20(31):5069-76 (2014).
Glasser et al., A multi-modal parcellation of human cerebral cortex, Nature 536:171-8 (2016).
Glasser et al., Trends and properties of human cerebral cortex: correlations with cortical myelin content, Neuroimage 93 Pt 2:165-75 (2014).
Gonzalez-Burgos et. al, GABA neurons and the mechanisms of network oscillations: implications for understanding cortical dysfunction in schizophrenia; Schizophr. Bull. 39:944-961 (2008).
Granger, Essential circuits of cognition: The brain's basic operations, architecture, and representations (2006).
Gunn et al., Imaging in CNS Drug Discovery, Sminars in Nuclear Medicne, Updates in Molecular Brain Imaging, vol. 47, issue 1, Jan. 2017.
Hariri AR et al., The amygdala response to emotional stimuli: a comparison of faces and scenes, Neuroimage, 17:317-323 (2002).
Hawrylycz et al., Canonical genetic signatures of the adult human brain, Nature Neuroscience, vol. 18, No. 12, pp. 1832-1842 and online methods (Dec. 2015).
Hawrylycz et al., An anatomically comprehensive atlas of the adult human brain transcriptome, Nature 489:391-9, Figure 2 (2012).
Insel et al., Next-generation treatments for mental disorders, Sci. Transl. Med., 4:155ps19 (2012).
Kuperberg GR et al., Neuroanatomical distinctions within the semantic system during sentence compreshension: evidence from functional magnetic resonance imaging, Neuroimage, 40:367-388 (2008).
Manuck SB et al., Temporal stability of individual differences in amygdala reactivity, Am. J. Psychiatry, 164:1613-1614 (2007a).
Mittal et al., β2-Adrenoreceptor is a regulator of the α- synuclein gene driving risk of Parkinson's disase, Science, 357(6354):891-898 (2017).
Morioka T. et al., Comparison of magnetoencephalography, functional MRI, and motor evoked potentials in the localization of the sensory-motor cortex, Neurological Research, 17:361-367 (1995).
Phan, K. Luan et. al., Real-time fMRI of cortico-limbic brain activity during emotional processing, Neuroreport, 15:527-532 (2004).
Richiardi et al., Correlated gene expression supports synchronous activity in brain networks, Imagen consortium, Science 348:1241-4 (2015).
Romme et al., Conectome disconnectivity and cortical gene expression in patients with schizophrenia, Biol. Psychiatry (2016).
Tamminga et al., Biopolar and Schizophrenia Network for Intermediate Phenotypes: Outcomes Across the Psychosis Continuum. Schizophr. Bull. 40:S131-S137 (2014).
Tebbenkamp et al., The developmental transcriptome of the human brain: implications for neurodevelopmental disorders, www.coneurology.com, vol. 27, No. 00 (2014).
Tozzi et al., Dopamine D2 receptor activation potently inhibits striatal glutamatergic transmission in a G2019S LRRK2 genetic model of Parkinson's disease, Neurobiol Dis, 118: 1-8 (2018).
Whitaker et al., Adolescence is associated with genomically patterned consolidation of the hubs of the human brain connectome, NSPN Consortium, Proc. Natl. Acad. Sci. USA 113:9105-10 (2016).
Whitfield-Gabrieli et al., Hyperactivity and hyperconnectivity of the default network in schizophrenia and in first-degree relatives of persons with schizophrenia, Proc. Natl. Acad. Sci. USA 106:1279-84 (2009).
Wong et al., The Role of Imaging in Proof of Concept for CNS Drug Discovery and Development, Neuropsychopharmacology Reviews, 34, 187-203 (2009).
Yamada et al., Resting-State Functional Connectivity-Based Biomarkers and Functional MRI-Based Neurofeedback for Psychiatric Disorders: A Challenge for Developing Theranostic Biomarkers, Intl. J. of Neuropsychopharmacology, 20(10): 769-781 (2017).
Yang et al., Functional hierarchy underlies preferential connectivity disturbances in schizophrenia, Proc. Natl. Acad. Sci. USA 113:E219-28 (2016).
Yarkoni et al., Large-scale automated synthesis of human functional neuroimaging data, Nat. Methods 8:665-70 (2011).
Zhao et al., Connectome-scale group-wise consistent resting-state network analysis in autism spectrum disorder, NeuroImage: Clinical 12; 23-33 (2016).

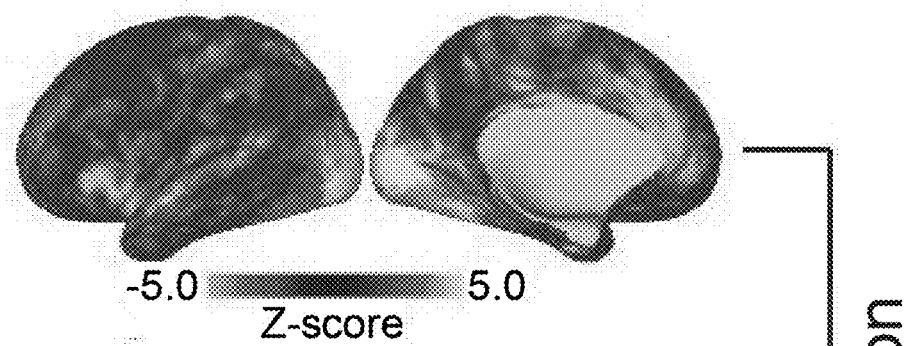
FIG. 12A
Gene expression maps
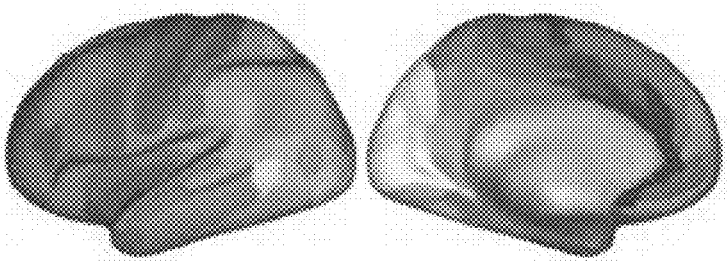
HTR2A
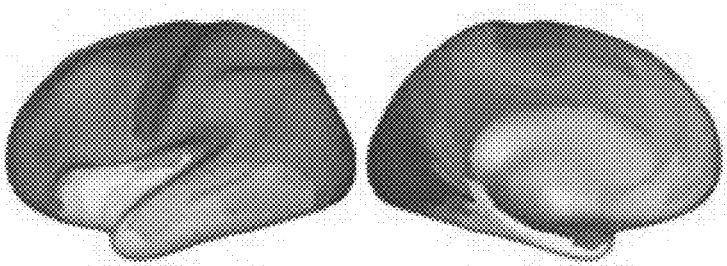
HTR1A
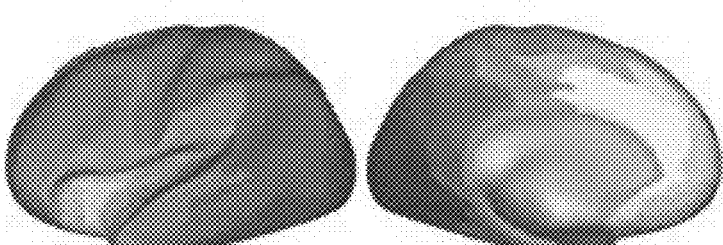
HTR7
FIG. 12B

Phenotype Gene Distribution

Achenbach Adult Self-Report Questionnaire Syndrome Scale

Cortex Only

CCR5  CXCR4  CXCR7

Add Gene  Submit

METHODS AND SYSTEMS FOR COMPUTER-GENERATED PREDICTIVE APPLICATION OF NEUROIMAGING AND GENE EXPRESSION MAPPING DATA

BACKGROUND

Technical Field

The tools and methods described herein relate to a genotype and neurophenotype topography-based approach for analyzing brain neuroimaging and gene expression maps to identify drug targets associated with neurobehavioral phenotypes and, conversely, neurobehavioral phenotypes associated with potential drug targets, to develop rational design and application of pharmacological therapeutics for brain disorders. These tools and methods also provide for treatment of subjects in need of neurological therapy. Described herein is the selection, optimization, and ultimately targeting of therapeutics to specific neural circuits based on the bi-directional alignment of the neurobehavioral phenotypes and gene expression maps. This approach produces an actionable set of practical steps to aid therapeutic design and decision making based on the alignment or comparison of neuro-behavioral and transcriptomic data and the definition, and exploitation of, new neurophenotype topographies and genotype topographies.

Among other things, this approach may facilitate clinical trial design, for example, by providing for screening of individual subjects for inclusion or exclusion in a trial based on neuroimaging or behavioral measurements, and helps determine for which measurements efficacy should be assessed.

Also, described herein is a set of specific computational procedures, including definition of unique neurophenotype topographies and genotype topographies and the ability to score alignment or comparison of neurobehavioral phenotype information and transcriptomic information using new neurophenotype topographies and genotype topographies to yield the desired results. Exemplary functional block diagrams of the computation workflow are provided and described herein.

Description of the Related Art

Development of new central nervous system (CNS) drugs is hindered by, among other things, a poor understanding of CNS disease biology. For example, choosing suitable targets and knowing when to intervene and how to move the biology effectively is difficult. This is particularly the case as some diseases such as schizophrenia and Parkinson's disease (PD) develop over may years, which makes target identification challenging. Moreover, this challenge is made greater by the massive variation across groups of patients suffering from neuropsychiatric disorders; picking the correct treatment for the correct patient based on their specific central nervous system alterations is currently out of reach. Also, while targets may be validated by animal models, genetics, pathophysiology, or human pharmacology, assessing validation study results is generally based on judgement that varies among individuals and companies about the strength and productivity of the data.

The many limitations of animal models used for CNS drug development are recognized; thus, alternative validation methods are becoming increasingly important. Also, there is a paucity of predictive animal models for CNS disorders. Bain et al., *Therapeutic Development in the Absence of Predictive Animal Models of Nervous System Disorders: Proceedings of a Workshop*, THE NATIONAL ACADEMIES PRESS (2017), available at: http://nap.edu/24672 ("Bain"). And even while animal models may be used to link well-described, distinct biological phenomena to symptoms of a complex disease such as schizophrenia, the explanatory power of such models comes from working out the mechanistic basis for a phenotype and application of great discipline to prevent overgeneralization of results. Generally, testing CNS behavioral paradigms in animals to measure neurobehavioral phenotype in the animal may only loosely relate to the human neurobehavioral phenotype of interest for clinical application.

Also, even as many animal models are based on an increased understanding of human genetics, it is understood that individual genes and variants may have only small effects and not be fully penetrant; meanwhile, large-effect variants often cause constellations of symptoms which further complicate interpretation. Also, large-effect risk factors may not be shared across species and an animal's genetic background can complicate phenotype interpretation. For some CNS disorders, existing animal models do not produce the key pathologic features or symptoms of the disease, and as a result may not be able to demonstrate whether a drug is going to be effective (e.g., Parkinson's disease animal models do not show Lewy bodies composed of aggregated alpha-synuclein and highly heterogeneous diseases such as schizophrenia would require several models for specific disease aspects or subtypes). Finally, there are simply aspects of the human nervous system that are not represented in virtually any other animal such that attempts to recapitulate human CNS disease in animal models may be fundamentally flawed.

Translational gaps also exist between identifying and validating a target and developing a clinical measure or biomarker that can predict a response and a disease. Moreover, even if a target is identified and validated, it may be inaccessible or difficult to move the biology in a way that will be therapeutic. These problems are especially severe for CNS disorders.

Another factor complicating further CNS drug development is that current CNS therapeutics are screened for broad symptom indications rather than specific neurobehavioral phenotypes and, ultimately, specific people. Thus, patient populations are defined at a group level to minimize adverse events while maintaining effects with respect to broad symptoms. This generalized 'group average' approach overlooks specific neurobehavioral phenotype complexities and may not best address patient needs.

The above-noted and other difficulties facing CNS drug development account for the fact that the success rates for development of CNS drugs are among the lowest of all therapeutic areas. TCSDD. 2014. *CNS drugs take longer to develop, have lower success rates, than other drugs*. IMPACT REPORT Volume 16, No. 6, Tufts University. Further, because many of the approved drugs are merely iterative, apparent gains in approved drug numbers can lead to a false sense of success. Thus, to serve patients well and to increase the flow of drugs needed to treat the hundreds of millions of people with CNS disorders (such as depression, schizophrenia, and Alzheimer's disease (AD)) and other problematic CNS symptoms and cognitive processes, more efficient discovery and development methods are needed. To allow practical and actionable difference and impact relative to existing approaches, such methods need to be grounded in human neurobiology.

Importantly, brain function has been conventionally described as involving neural circuits, or a collection of brain regions that are connected to carry out a particular function. That is, it is understood that biological systems achieve their cognitive capabilities solely through brain mechanisms: the physiological operation of anatomical circuitries. Brain circuits are important because neurons do not work in isolation and can constitute various sizes ranging from small (micro) scale to large (macro) scale. The brain circuits concept is built on the principle that what allows our brain to process information is the fact that one neuron sends information to the next and so on. Thus, it is the connection between the neurons that matters. Brain circuits, which can be observed and mapped with neuroimaging and related mapping data, reflect the fact that a number of different neurons in different regions may connect with each other to work together and to treat or process information jointly. Growing knowledge in neuroscience and related fields is revealing the data crucial for characterizing the layout and properties of these circuits, yet much remains to be learned and the characterization of various circuits is not totally or imperfectly defined.

It is generally believed that the human brain consists of evolutionarily recent forebrain circuit designs (telencephalic circuits) layered on top of preserved ancient (e.g., reptilian) circuits, with the new designs accounting for more than 90% of the volume of the human brain. There are four primary divisions of telencephalic forebrain (cortex, striatal complex, hippocampal formation, amygdala nuclei), and many subdivisions (e.g., anterior vs posterior cortex, five cortical layers, local circuits, striatal components, hippocampal fields CA1, CA3, dentate gyrus, subiculum, etc.), each with its own cell types and local circuit design layouts, thus presumably each conferring unique computational properties. R. Granger, *Essential circuits of cognition: The brain's basic operations, architecture, and representations* (2006). Nonetheless, understanding of brain circuitry continues to develop as new circuits are discovered and previously described circuits are redefined or better characterized.

Currently, efforts are underway to building a human "connectome," or a comprehensive map of the brain's circuits. This is an enormously challenging endeavor, for the brain consists of billions of cells, and each cell contacts thousands of others. It is believed that an improved understanding of brain circuits will bring scientists one step closer to understanding how the brain functions when healthy and how it fails to function when injured or diseased, and how to best return the brain to health.

Coincidentally, there is also a growing recognition that redefining mental disorders as disorders of brain circuits is vital for the rational design of pharmaceutical treatments for CNS disorders. Insel et al., *Next-generation treatments for mental disorders*, SCI. TRANSL. MED., 4:155ps19 (2012). Yet a great challenge remains in how to harness emerging findings of circuit definition and characterization for neurobehavioral processes and pathologies, such as specificity of effects at the level of brain regions as revealed by noninvasive neuroimaging for the rational design of pharmaceutical treatments for CNS disorders. This problem can be posed bi-directionally. That is, for a given drug, which neurobehavioral pathology might it be well suited to treat? Conversely, for a given pathology, which drug targets (e.g., synaptic receptors) or drugs might be well suited for its treatment?

Noninvasive neuroimaging methods, such as functional magnetic resonance imaging (fMRI), have enabled great progress in elucidating circuits involved in diverse neurobehavioral phenotypes, including disorders (e.g., schizophrenia), symptom dimensions (e.g. cognitive deficits), and processes (e.g., working memory). Moreover, these methods are being applied to discover neural biomarkers, which can potentially inform patient-specific treatments. See, e.g., Drysdale et al., *Resting-state connectivity biomarkers define neurophysiological subtypes of depression*, NAT. MED. (2016), Epub Ahead of Print available at: http://00ev39.myregisteredwp.com/wp-content/upload/sites/3661/2017/01/Resting-state-connectivity-biomarkers-define-neuro-physyiological-subtypes-of-depression.pdf; Drysdale et al., *Resting-state connectivity biomarkers define neurophysiological subtypes of depression*, NAT. MED., January; 23(1): 28-38 (2017) (collectively, "Drysdale"). Neuroimaging research reveals structure and variation of phenotype-related effects across different brain regions, which highlights the need for the circuit-based perspective so as to better include all regions of a particular circuit. This variation can be expressed as a brain map. In one example, a brain map may use an assignment of a numerical value to each brain region reflecting the magnitude of a particular feature which may relate to phenotype-related variation within or across subjects.

Meanwhile, to the extent that genetic information has been used to make circuit-based maps, these were based on post-mortem analyses without a reference functional map derived from within or between subject imaging data. See Tebbenkamp et al., *The developmental transcriptome of the human brain: implications for neurodevelopmental disorders*, www.co-neurology.com, vol. 27, no. 00 (2014); Akbarian et al., *The PsychENCODE project*, NATURE NEUROSCIENCE, Vol. 18, No. 12, December (2015); and Gandal et al., Shared molecular neuropathology across major psychiatric disorders parallels polygenic overlap, SCIENCE, 359, 693-697, 9 February (2018).

As described further below, conventionally understood neural circuits are readily distinguishable from the neurophenotype topographies and genotype topographies described herein. Here, neural circuit-based findings raise several questions, including the question of how administration of a pharmaceutical drug, which is systemic, can be tailored to preferentially target a specific brain circuit or subset of brain circuits. In rational drug design and real world patient treatment, an important consideration is minimization of "off-target" molecule effects. And a brain circuit-based approach may also consider the potential effects of systemic drug administration on "off-target" brain regions, or brain regions that fall outside of a brain circuit or subset of brain circuits.

Innovative modeling systems, such as cellular and computational models, may mitigate the current lack of predictive animal models. It has been suggested that data from human clinical studies and experimental medicine approaches should be better used to advance a fundamental understanding of human diseases. Also, significantly, the scientific community has gained open access to neuroimaging databases and spatially comprehensive maps of brain gene expression. And the amount of publicly available neuroimaging and gene expression data continues to increase. This data opens up exciting ways to use gene expression data and neuroimaging data to understand brain organization, with major benefits for both basic and clinical science. Yet these new opportunities also present numerous technical and theoretical challenges. Such challenges include, for example: (1) the absence of multimodal data analytic pipelines to scalaby, reproducibly and efficiently ingest and analyze neuroimaging data from open sources;

(2) the difficulty of projecting gene expression data into cortical surface and brain volumes within which neuroimaging results are interpreted; and (3) the use of categorical descriptions of patients populations without resolution into the underlying behavioral or symptom structures that characterize these patients.

Historically, the conventional approach to using neuroimaging to guide drug discovery or development has focused on identifying if a candidate drug binds (e.g. PET-based imaging) or changes the activity (e.g. fMRI-based imaging) in a brain region. Gunn et al., *Imagine in CNS Drug Discovery*, SEMINARS IN NUCLEAR MEDICINE, UPDATES IN MOLECULAR BRAIN IMAGING, vol. 47, issue 1, Jan. (2017); Wong et al., *The Role of Imaging in Proof of Concept for CNS Drug Discovery and Development*, NEUROPSYCHOPHARMACOLOGY REVIEWS, 34, 187-203 (2009). Each method relies on a Region of Interest (ROI) approach. By contrast, the approach proposed here incorporates surface-based topography and cortical parcellation to relate genes, and potential drug targets, to global brain activity associated with a phenotype of interest. The omission of cortical surface topography from ROI-based methods provides an inherent limitation to the conventional uses of neuroimaging for CNS drug discovery and development.

BRIEF SUMMARY

The tools and methods described herein relate to new genotype and neurophenotype topography-based methods and tools for analyzing brain neuroimaging and gene expression maps, or genotype topographies, to identify drug targets associated with neurobehavioral phenotypes and, conversely, neurobehavioral phenotypes associated with potential drug targets. In one embodiment, these tools and methods can be used to facilitate or develop rational design and application of pharmacological therapeutics for brain disorders. In another embodiment, the present tools and methods also provide topography-based methods and tools for treatment of subjects in need of neurological therapy.

These tools and methods may include a computational neuroinformatics software and computer platform. This platform integrates derived brain neuroimaging maps, which provide a numerical value to each brain region reflecting the magnitude of a particular feature which may relate to phenotype-related variation within or across subjects, with gene expression maps or genotype topographies, which provide a numerical value reflecting the expression levels of genes across brain regions obtain from one or more subjects, and leverages advances in large-scale brain mapping neuroinformatics to derive a score that reflects the alignment of the derived maps. By pooling, selecting, assessing, adjusting, weighting, masking, comparing, and quantifying the alignment of gene expression maps with neuroimaging maps, and using a topography-based approach to characterize those brain areas or regions, or circuits, associated with a particular neurophenotype, these tools and methods provide predictive capabilities for association of therapeutic targets with neurobehavioral phenotypes CLEAN VERSION OF THE SPECIFICATION (e.g., disorders, symptoms, cognitive processes, etc.). The present tools and methods may also provide enhanced capabilities for defining and assessing genotype and neurophenotype topography-based methods of treatment relating to CNS disorders. Thus, the present tools and methods open a new route to efficient rational design and refinement and application of genotype and neurophenotype topography-based therapeutics for modulating neurobehavioral phenotypes (i.e., for both treating dysfunction and augmentation of function).

The present tools and methods are needed to untangle, re-order, prioritize, layer, compare, interpret, integrate, and apply available brain mapping information (e.g., neuroimaging maps and gene expression maps) with respect to targets of therapeutic interest, and do so using a genotype and neurophenotype topography-based approach, i.e., an approach that is not necessarily confined by conventionally understood brain circuit characterizations.

The present tools and methods newly characterize neural circuits by taking into account neurobehavioral phenotype information and transcriptomic information. This approach includes methods designed to include or be informed or guided by data derived from individual or group behavioral or symptom phenotypes. In this aspect, the present approach differs from other approaches relying on ontological associations of transcriptomic profiles to implicate genes or drugs in particular genes, or descriptions of resting-state functional connectivity as a potential biomarker for psychiatric disorders without reference to particular genes or drug targets. Hawrylcz et al., *Canonical genetic signatures of the adult human brain*, NATURE NEUROSCIENCE, vol. 18, no. 12, pp. 1832-1842 and online methods (December 2015); Yamada et al., *Resting-State Functional Connectivity-Based Biomarkers and Functional MRI-Based Neurofeedback for Psychiatric Disorders: A Challenge for Developing Theranostic Biomarkers*, INTL. J. OF NEUROPSYCHOPHARMACOLOGY, 20(10): 769-781 (2017).

The present tools and methods address, among other things, certain gaps in the field. For example, many investigations focused on identifying gene transcripts that were differentially regulated between control and patient populations; accordingly, such studies defined patient populations at the "spectrum" level, i.e. without reference to underlying biology that accounts for particular symptom profiles. See e.g., Liu et al., *DAWN: a framework to identify autism genes and subnetworks using gene expression and genetics*, MOLECULAR AUTISM, 5:22 (2014); Zhao et al., *Connectome-scale group-wise consistent resting-state network analysis in autism spectrum disorder*, NEUROIMAGE: CLINICAL 12; 23-33 (2016). Here, the present tools and methods bridge such gaps by including reference to the underlying biology that accounts for neurobehavioral phenotypes.

Here, problems affecting rational CNS drug design and treatment of CNS disorders are addressed using a genotype and neurophenotype topography-based approach that incorporates gene expression data and neuroimaging data for the rational design of pharmaceutical treatments for CNS disorders. The present approach improves, builds on, and refines, and redefines, circuit-derived knowledge of how the biophysical properties of neural circuits and the drug target densities vary across brain regions for a particular neural phenotype, and integrates two types of brain mapping—neurobehavioral phenotype mapping and gene expression mapping—to provide the new genotype and neurophenotype topography-based approach detailed below.

Inquiries addressed by the present tools and methods may be, for example, directed to identification of drug targets associated with neurobehavioral phenotypes and, conversely, neurobehavioral phenotypes associated with potential drug targets. Accordingly, the present genotype and neurophenotype topography-based approach provides for the development of rational design and application of pharmacological therapeutics for brain disorders.

The present tools and methods address several problems, including providing greater specificity for discerning, identifying, comparing, determining, or mapping links between neurobehavioral phenotypes and therapeutics. In this instance, the conventional circuit-based approach is replaced by a genotype and neurophenotype topography-based approach that takes into consideration both neuroimaging maps and gene expression maps to define or characterize areas or regions of potential or actual therapeutic activity, and may also identify potential areas or regions of off-target delivery.

A problem addressed by the present tools and methods is the provision of more precise targeting which is needed to address variations existing within a broad neurobehavioral phenotype.

Another problem addressed by the present tools and methods is the provision of more precise targeting of therapeutics to specific brain areas needed to preferentially modulate more critical areas or regions and to minimize effects on off-target areas or regions by providing a genotype and neurophenotype topography-based approach.

Yet another problem addressed by the present tools and methods is the provision of formalism needed to identify potential therapeutics to more precisely target critical areas or regions involved with a particular neurobehavioral phenotype of interest. For example, the present tools and methods may be used to identify drugs which can selectively target the brain areas or regions involved in a neurobehavioral phenotype of interest.

Another problem addressed by the present tools and methods is the provision of the formalism needed to identify neurobehavioral phenotypes as candidates for treatment, which can be identified by phenotypes whose characteristic brain maps are aligned with the gene expression maps associated with a particular drug of interest.

Another problem addressed by the present tools and methods is the provision of the formalism needed to generate insight across species based on relating gene expression maps.

Another problem addressed by the present tools and methods is the provision of the brain genotype and neurophenotype topography-based formalism needed to rationally develop combinations of multiple therapeutics to precisely target key brain areas or regions. At present, no formalism exists for maximizing effects of polypharmacy to areas that express genes coding for drug targets.

The present tools and methods may also provide for individualized treatment selection. The present platform provides tools and methods to inform putative treatment response at the individual patient level based on either neural or behavioral data obtained from the patient.

The present tools and methods may also provide for identification of a drug target based on similarity to a gene implicated. For example, the present tools and methods may be sued to identify a drug target based on similarity to the APOE gene which is linked to Alzheimer's, and which is not directly drugable.

The present tools and methods may also provide for identification of drug targets based on one or more genes' similarity to a neural circuit implicated.

The present tools and methods may also provide for selection of a suitable patient population subset, or purification of patient population, to test efficacy of application (i.e. clinical trial optimization), by examining drug targets associated with neurobehavioral phenotypes or, conversely, neurobehavioral phenotypes associated with potential drug targets.

The present tools and methods may also provide for selection of drugs for a clinical trial or for animal testing.

The present approach provides a method to inform putative target engagement based on alignment of potential drug targets to a neuroimaging map.

The present tools and methods may also provide for animal applications of phenotype-transcriptome mapping. The present approach provides a method to produce a high-throughput screen via a disease animal model (e.g. knockout). Given a neurophenotype map in the animal, the present approach provides a method to sweep across genes that maximally align with such map. This provides a method of use for improved or more accurate therapeutic design.

The present tools and methods may also provide for diagnostic decisions for specific people based on implicated neural circuits, or based on behavioral variation for which there are quantitative links to relevant neurophenotypes.

The present tools and methods may also provide for prognosticating the effect of an administered therapy based on gene transcriptome alignment.

The present tools and methods may also provide for prognosticating the putative treatment response prior to full blown illness (i.e. risk) for neural circuit alteration based on gene transcriptome alignment.

The present tools and methods may also provide for bypassing invasive pharmacoimaging. Specifically, the present approach can provide a way to identify a neurophenotype if there is a known clinical pharmacological response in a group of individuals with known symptom responses. Here, if the neural-behavioral mapping is unknown then this application would pinpoint a given circuit based on known response in relation to gene transcriptome for that drug.

The present tools and methods may also provide for polypharmacy.

The present tools and methods may also inform neurobehavioral mapping in clinical response to a given drug via transcriptome profile, or gene mapping, for the receptor targeted by a given drug. For example, here "transcriptome profile" may refer to gene-gene mapping, i.e., because we know what a drug that targets a particular gene (gene #1) does based on clinical evidence, we can infer a similar clinical response based on the similarity of distribution of a drug that targets a novel gene (gene #2). And "gene mapping" may refer to the ability to infer effect of a therapeutic based solely on the pattern of expression of the gene it targets within functional circuits (i.e. collection of brain regions that together to carry out a particular function).

Specifically, if two drugs induce differential symptom response in a clinical trial, then the known alignment of their receptor targeting with a given transcriptome map implicates a neural circuit in that symptom change.

For instance, while conventional neural circuit boundaries are established by invasive or non-invasive neural recording or neuroimaging techniques, the present alignment between the neurophenotype topography and the gene expression maps, or genotype topography, can point to a circuit that would be invisible to the conventional circuit mapping techniques. Put differently, using the conjunction of the gene expression and neural or neurophenotype maps allows the definition of novel putative circuits that are maximally co-aligned.

Therefore, the neural circuit boundaries established using the present gene-neurophenotype alignment topographic approach may deviate from conventional neural circuit boundaries. One example of this deviation may be that the neurophenotypic variation map associated with a given disease exhibits maximal alignment with more than a single gene map, thus yielding an alignment across a circuit that would traditionally not be identifiable without such multi-gene alignment.

BRIEF DESCRIPTION OF THE SEVERAL VIEWS OF THE DRAWINGS

FIG. 5A illustrates the gene-to-phenotype direction. FIG. 5B illustrates the phenotype-to-gene direction. FIG. 5C illustrates the gene-to-gene direction, which identifies genes based on the statistical association of their topographies with the topography of a selected gene of interest.

FIG. 6A illustrates parcellated maps of cortical (left) and subcortical (right) expression topographies. FIG. 6B illustrates the mean expression values for the gene PDYN, at the resolution of brain structures (vertical axis) partitioned by functional networks (horizontal axis). FIG. 6C illustrates dense cortical maps.

FIGS. 9A and 9B show a gene-to-phenotype approach. FIG. 9A depicts a gene expression map for OPRK1 correlated with a set of neurobehavioral phenotype maps. FIG. 9B depicts a gene expression map for OPRL1 correlated with a set of neurobehavioral phenotype maps.

FIGS. 10A and 10B show a phenotype-to-gene approach.

FIG. 10A depicts story-math tasks correlated with a set of gene expression maps. FIG. 10B depicts fearful-neutral face stimuli correlated with a set of gene expression maps.

FIG. 11A shows the cortical gene similarity scores for four NMDA receptor subunits (GRIN2A, GRIN2B, GRIN2C, and GRIN2D). FIG. 11B shows the cortical gene similarity scores for four $GABA_A$ receptor subunits (GABRA1, GABRA2, GABRA3, GABRA4, and GABRA5).

FIGS. 12A, 12B, 12C, and 12D show that the platform can link from gene expression patterns to the neural effects of a drug. FIG. 12A shows the fMRI-derived cortical map showing the change in mean functional connectivity (Global Brain Connectivity, GBC), which exhibits a large increase in occipital visual cortex. FIG. 12B shows gene expression maps for three serotonin receptor genes, including HTR2A. FIG. 12C shows the gene-map correlation between the LSD-related neurophenotype map and six candidate genes which code for serotonin and dopamine receptors. FIG. 12D shows these correlation values in relation to the gray background distribution histograms showing the distribution of scores across all available genes in the AHBA dataset, showing that HTR2A is in the top 5% of all genes in its alignment with the LSD-related neurophenotype map.

FIG. 14A provides brain mapping images for the gene HRH3. FIG. 14B provides brain mapping images for the phenotype map BSNIP Symptom Correlations/GBC N436 BACS Comp Correlation. FIG. 14C provides alignment brain mapping images for the brain mapping images provided as FIG. 14A and FIG. 14B.

FIG. 15A provides a screen shot of the phenotypic gene distribution relating to Achenback Adult Self-Report Questionnaire Syndrome Scale. FIG. 15B provides an image showing the gene-map correlation for six (6) genes (HTR6, CHRM3, CHRM1, MAOA, HTR2A, and HTR2C). FIG. 15C provides a phenotype map HCP Cognitive Behavioral/HCP N338 GBC ASR SS Correlation. FIG. 15D provides another screen shot of the phenotypic gene distribution relating to Achenback Adult Self-Report Questionnaire Syndrome Scale. FIG. 15E provides another image showing the gene-map correlation for six (6) genes (HTR6, CHRM3, CHRM1, MAOA, HTR2A, and HTR2C). FIG. 15F provides a screen shot of the phenotypic gene distribution relating to Achenback Adult Self-Report Questionnaire Syndrome Scale. FIG. 15G provides another image showing the gene-map correlation for three (3) genes (CCR5, CXCR7, and CXCR4).

DETAILED DESCRIPTION

Figure 1A:
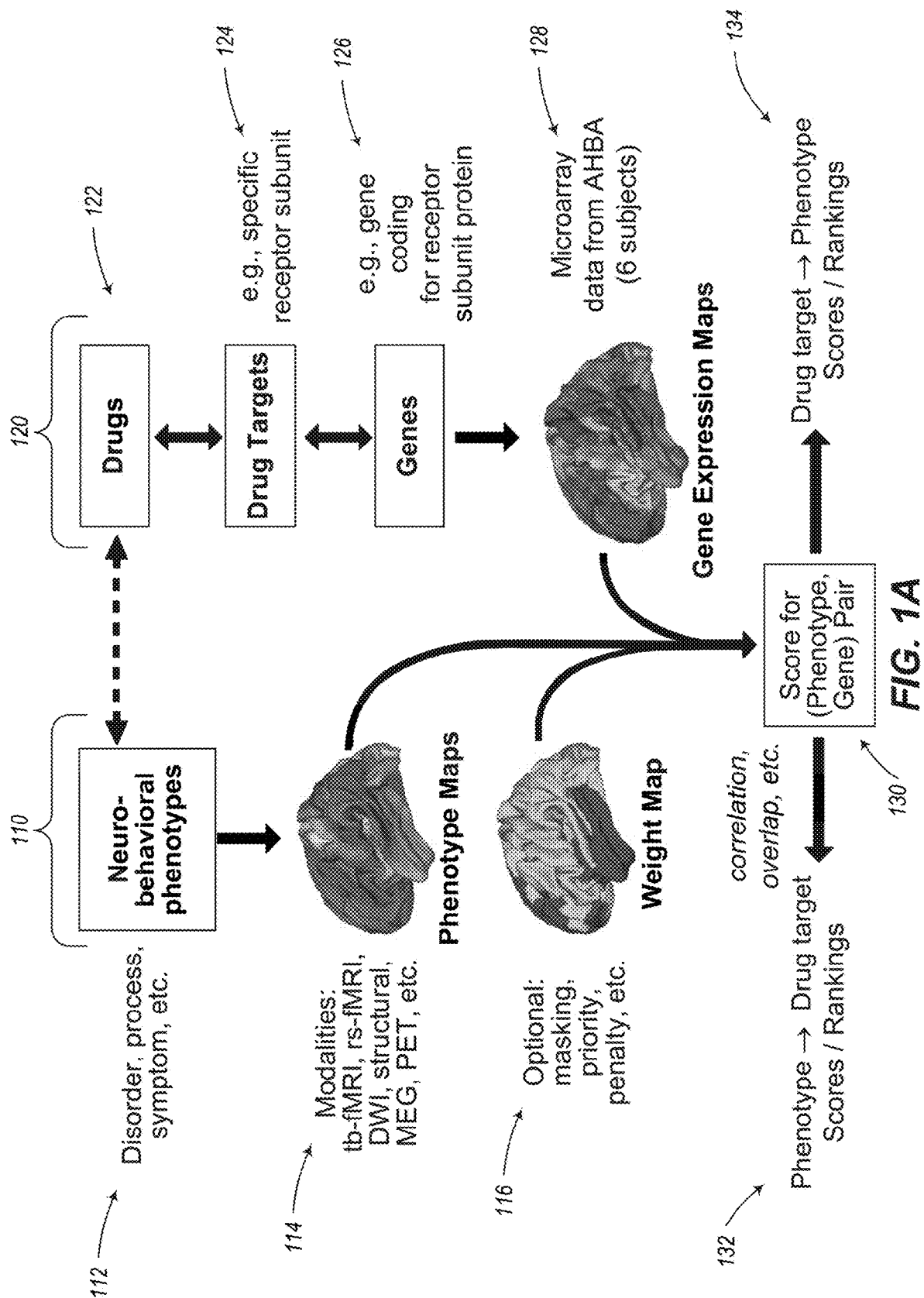
FIGS. 1A and 1B provide computational frameworks relating the scoring of pairs of neurophenotype maps and gene expression maps.

The present tools and methods integrate neurobehavioral phenotype mapping and gene expression mapping information for targeted genotype and neurophenotype topography delivery and comprise a computational neuroinformatics platform. This platform integrates neuroimaging maps with maps of gene expression in the human brain, leveraging advances in large-scale brain-mapping neuroinformatics. By quantifying the alignment of gene expression maps with neuroimaging maps and defining brain areas and regions of interest using a genotype and neurophenotype topography-based approach, this platform provides a method to associate drug targets with neurobehavioral phenotypes (e.g., disorders, symptoms, cognitive processes, etc.) and opens a route to efficient rational design of pharmacological therapeutics for brain disorders.

Generally, the tools and methods comprise two primary data inputs, neurobehavioral phenotype mapping and gene expression mapping, which is combined and processed to produce a numerical score for a given map-gene pair. The numerical score reflects the alignment of a given phenotype and gene expression mapping and includes a measure of statistical significance or confidence for this relationship based on a particular genotype and neurophenotype topography. The numerical score may also reflect the correlation of map values across brain locations, and may relate to one or more map-gene pairs, maps, genes, or neurobehavioral phenotypes.

The neuroimaging maps and gene expression maps may be from distinct sources, and may comprise heterogeneous source materials. The neuroimaging maps and gene expression maps may be pre-processed to sort or to exclude certain information or averaged prior to or during processing by a computational neuroinformatics platform. The neuroimaging maps and gene expression maps may be pre-processed or averaged in view of, or in keeping with, a particular genotype and neurophenotype topography prior to or during processing by a computational neuroinformatics platform. Optionally, the neurophenotype mapping information may be weighted or explicitly restricted to select brain locations. Optionally, the gene mapping information may be weighted or explicitly restricted to select brain locations.

The platform outputs comprise neuroimaging data files of all computed map data. These outputs include maps characterizing aligned and misaligned brain locations of phenotypic and gene expression mapping. Such outputs may relate to "off target" brain locations/regions. Output maps may be visualized using publically available neuroimaging software. Platform outputs may be provided in a format that reflects a particular genotype and neurophenotype topography as determined by the present tools and methods.

Definition of Terms

Unless defined otherwise, all technical and scientific terms used herein have the same meaning as is commonly understood by one of skill in the art to which these tools and methods belongs. Additional definitions are set forth throughout this disclosure.

As used herein, the term "neurophenotype topography" refers to the spatial pattern of values from a given neuroimaging measure associated with a neurophenotype. This is in contrast with a more conventional circuit-based approach because such an approach would provide a location-specific readout of some measure. Here the tools and methods consider distributed whole-brain or neural systems for spatial mapping of on-target versus off-target relationships of gene expression with a neurophenotype. In turn, this method moves well beyond a circuit-based approach based on a neuroimaging maps alone because it permits a spatial quantification of putative therapeutic effect beyond a punctate pre-defined circuit. As used herein, the terms neuroimaging map, neurobehavioral phenotype map, and neurophenotype topography are synonymous with one another.

As used herein, the term "gene expression mapping" and "genotype topography" may be used interchangeably.

As used herein, the term "neurobehavioral phenotype" refers to a behavioral or neural measurable feature depicted or provided, for example, as neuroimaging mapping data. Examples of neurobehavioral phenotype include, but are not limited to: broad psychiatric or neurological disorders or spectrums (e.g., schizophrenia); symptom dimensions (e.g., executive function); mental processes (e.g., working memory); functional features (e.g., resting-state functional connectivity derived from BOLD fMRI); structural features (e.g., DWI-derived probabilistic tractography, myelin, cortical curvature, cortical thickness, subcortical volume, fractional anisotropy); metabolic features (e.g., PET tracer map); electrophysiological features (e.g., EEG map); latent measures derived from a feature (e.g., latent measure of network topology); and features reflecting effect of pharmacological manipulations (e.g., effect of antipsychotic medication of PET metabolism and/or BOLD functional connectivity). As used herein, a neurobehavioral phenotype may be synonymous with a neurophenotype.

As used herein, the term "brain map" refers to an assignment of a numerical value to each brain location/region from a given analysis.

As used herein, the term "neuroimaging maps" refers to a numerical value for each brain region reflecting the magnitude of a particular feature which may relate to phenotype-related variation within or across subjects.

As used herein, the term "gene expression map" refers to a numerical value reflecting the expression levels of a specific gene across brain regions obtained from one or more subjects.

As used herein in neurophenotype map generation, the term "location" refers to a specific point, the term "region" or "area" refers to some broader areal extent, and the terms "system" or "network" refers group of regions that are functionally organized.

As used herein, the term "pre-processing" data refers to any cleanup strategy on the data leading to an neurophenotype map. For instance, in the case of BOLD data, these steps may involve but are not limited to motion correction, alignment across frames, phase unwrapping, removal of nuisance signal that may be artefactual, data-driven removal of spatially specific or pervasive artifact, registration to the group atlas, etc.

As used herein, the term "contacting" may be used with respect to data from a first source communicating, touching, coming into proximity with, aligning, or interacting with data from a second source, wherein said contacting allows for data from a first source to be one or more of analyzed, compared, assessed for similarity or contrast, likened, correlated, associated with, linked, or related to data from a second source. "Contacting" may occur in any physical or electronic medium that stores and allows distribution, processing, or other use of data.

As used herein, the term "normalizing" data refers to the procedure of quantitatively scaling the data to value relative to a common reference.

As used herein, the term "weighting" data refers to procedure of quantitatively scaling the values of data according to a relative priority.

As used herein, the term "masking" data refers to the procedure of excluding or including portions of the data from further analyses.

Neurobehavioral Phenotypes and Mapping

Neurobehavioral phenotypes refer to disorders, symptoms, cognitive processes, etc. (and may be collectively referred to herein as "disorders"). Examples of such disorders include, but are not limited to, the following disorders: schizophrenia, including psychosis; anxiety disorders, including panic disorder, post-traumatic stress disorder, and anxiety; mood and other affective disorders, including major depression, geriatric depression, and bipolar disorder; mood disorders in epilepsy; personality disorders, such as borderline personality disorder, obsessive-compulsive disorder; cognitive changes associated with chemotherapy; attention deficit hyperactivity disorder (ADHD); sex differences in brain function in health and disease (e.g., premenstrual dysphoric disorder); and traumatic brain injury.

Main classes of mental illness include, for example, the following. Neurodevelopmental disorders refer to a mental illness class that covers a wide range of problems that usually begin in infancy or childhood, often before the child begins grade school. Examples include autism spectrum disorder, attention-deficit/hyperactivity disorder (ADHD) and learning disorders. Schizophrenia spectrum and other psychotic disorders refer to a class of psychotic disorders that cause detachment from reality, such as delusions, hallucinations, and disorganized thinking and speech. The most notable example is schizophrenia, although other classes of disorders can be associated with detachment from reality at times. Bipolar and related disorders refer to a class that includes disorders with alternating episodes of mania, periods of excessive activity, energy and excitement, and depression. Depressive disorders refers to a class that include disorders that affect how you feel emotionally, such as the level of sadness and happiness, and they can disrupt your ability to function. Examples include major depressive disorder and premenstrual dysphoric disorder. Anxiety disorders relate to feelings of anxiety, an emotion characterized by the anticipation of future danger or misfortune, along with excessive worrying. Anxiety disorders can include behavior aimed at avoiding situations that cause anxiety. This class includes generalized anxiety disorder, panic disorder and phobias. Obsessive-compulsive and related disorders include disorders that involve preoccupations or obsessions and repetitive thoughts and actions. Examples include obsessive-compulsive disorder, hoarding disorder and hair-pulling disorder (trichotillomania). Trauma- and stressor-related disorders include adjustment disorders in which a person has trouble coping during or after a stressful life event. Examples include post-traumatic stress disorder (PTSD) and acute stress disorder. Dissociative disorders include disorders in which your sense of self is disrupted, such as with dissociative identity disorder and dissociative amnesia. Somatic symptom and related disorders may be found in person that may have physical symptoms with no clear medical cause, but the disorders are associated with significant distress and impairment. The disorders include somatic symptom disorder (previously known as hypochondriasis) and factitious disorder. Feeding and eating disorders may include disturbances related to eating, such as anorexia nervosa and binge-eating disorder. Elimination disorders may relate to the inappropriate elimination of urine or stool by accident or on purpose. Bedwetting (enuresis) is an example. Sleep-wake disorders may include disorders of sleep severe enough to require clinical attention, such as insomnia, sleep apnea and restless legs syndrome. Sexual dysfunctions may include disorders of sexual response, such as premature ejaculation and female orgasmic disorder. Gender dysphoria may refer to the distress that accompanies a person's stated desire to be another gender. Disruptive, impulse-control and conduct disorders may include problems with emotional and behavioral self-control, such as kleptomania or intermittent explosive disorder. Substance-related and addictive disorders may include problems associated with the excessive use of alcohol, caffeine, tobacco and drugs. This class also includes gambling disorder. Neurocognitive disorders may affect a person's ability to think and reason. These acquired (rather than developmental) cognitive problems include delirium, as well as neurocognitive disorders due to conditions or diseases such as traumatic brain injury or Alzheimer's disease. Personality disorders may involve a lasting pattern of emotional instability and unhealthy behavior that causes problems in your life and relationships. Examples include borderline, antisocial and narcissistic personality disorders. Paraphilic disorders may include sexual interest that causes personal distress or impairment or causes potential or actual harm to another person. Examples are sexual sadism disorder, voyeuristic disorder and pedophilic disorder. Other mental disorders may include mental disorders that are due to other medical conditions or that don't meet the full criteria for one of the above disorders.

The defining symptoms for each mental illness are detailed in the Diagnostic and Statistical Manual of Mental Disorders (DSM-5), published by the American Psychiatric Association. This manual is used by mental health providers to diagnose mental conditions and by insurance companies to reimburse for treatment.

Conventional diagnosis of a mental illness may include a physical exam to try to rule out physical problems that could cause your symptoms, lab tests including, for example, a check of your thyroid function or a screening for alcohol and drugs, and a psychological evaluation. During a psychological evaluation a doctor or mental health provider may talk to a person about his or her symptoms, thoughts, feelings and behavior patterns, and a person may be asked to fill out a questionnaire to help answer these questions.

Psychiatrists tend to use a system of diagnosis which identifies 10 types of personality disorder: paranoid personality disorder; schizoid personality disorder; schizotypal personality disorder; antisocial personality disorder; borderline personality disorder; histrionic personality disorder; narcissistic personality disorder; avoidant (or anxious) personality disorder; dependent personality disorder; and obsessive compulsive personality disorder. The types are grouped into three categories: (1) Suspicious—paranoid, schizoid, schizotypal and antisocial; (2) Emotional and impulsive—borderline, histrionic and narcissistic; and (3) Anxious—avoidant, dependent and obsessive compulsive.

Attention deficit hyperactivity disorder may be divided into three different types: inattentive type; hyperactive-impulsive type; and combination type.

Neurodegenerative diseases may include, for example, Alzheimer's disease, Parkinson's disease; amyotrophic lateral sclerosis; Friedreich's ataxia; Huntington's disease; Lewy body disease; and spinal muscular atrophy.

Signs and symptoms of mental illness can vary, depending on the disorder, circumstances and other factors. Mental illness symptoms can affect emotions, thoughts and behaviors. Examples of signs and symptoms may include, for example: feeling sad or down, confused thinking or reduced ability to concentrate, excessive fears or worries, or extreme feelings of guilt, extreme mood changes of highs and lows, withdrawal from friends and activities, significant tiredness, low energy or problems sleeping, detachment from reality (delusions), paranoia or hallucinations, inability to cope with daily problems or stress, trouble understanding and relating to situations and to people, alcohol or drug abuse, major changes in eating habits, sex drive changes, excessive anger, hostility or violence, and suicidal thinking. Sometimes symptoms of a mental health disorder appear as physical problems, such as stomach pain, back pain, headache, or other unexplained aches and pains.

Symptoms of major depression include feelings of sadness, loss of interest in normally pleasurable activities (anhedonia), changes in appetite and sleep, loss of energy, and problems with concentration and decision-making. Episodes of dysthymia resemble depression but are milder and often last longer. Bipolar disorder is characterized by alternating cycles of depression and mania. Symptoms of mania include elevated or expansive mood, inflated sense of self-esteem or self-importance, decreased need for sleep, racing thoughts, and impulsive behavior. Episodes of hypomania are typically shorter in length and less severe than mania. Cyclothymia is marked by cycles of low-level depression and hypomania.

Affective disorders may include Unipolar Depression and its variants including: postpartum depression, atypical depression, seasonal affective disorder; bipolar disorder; dysthymia and cyclothymia; generalized anxiety disorder; panic disorder; phobias including agoraphobia; obsessive compulsive disorder (OCD); and post-traumatic stress disorder (PTSD). There are several types of mood disorders: major depression, bipolar disorder (also known as manic depression), dysthymia, and cyclothymia.

Mental illnesses, in general, are thought to be caused by a variety of genetic and environmental factors. These factors may include inherited traits, environmental exposures before birth, and brain chemistry. For example, mental illness is more common in people whose blood relatives also have a mental illness. Certain genes may increase your risk of developing a mental illness, and your life situation may trigger it. Also, exposure to environmental stressors, inflammatory conditions, toxins, alcohol or drugs while in the womb can sometimes be linked to mental illness. Additionally, neurotransmitters are naturally occurring brain chemicals that carry signals to other parts of your brain and body. When the neural networks involving these chemicals are impaired, the function of nerve receptors and nerve systems change, leading to depression.

Certain factors may increase a person's risk of developing mental health problems, including: having a blood relative, such as a parent or sibling, with a mental illness; stressful life situations, such as financial problems, a loved one's death or a divorce; an ongoing (chronic) medical condition, such as diabetes; brain damage as a result of a serious injury (traumatic brain injury), such as a violent blow to the head; traumatic experiences, such as military combat or being assaulted; use of alcohol or recreational drugs; being abused or neglected as a child; having few friends or few healthy relationships; and a previous mental illness.

Mental illness is common. About one in five adults has a mental illness in any given year. Mental illness can begin at any age, from childhood through later adult years, but most begin earlier in life. The effects of mental illness can be temporary or long lasting. A person also can have more than one mental health disorder at the same time. For example, a person may have depression and a substance use disorder.

Mental illness is a leading cause of disability. Untreated mental illness can cause severe emotional, behavioral and physical health problems. Complications sometimes linked to mental illness include: unhappiness and decreased enjoyment of life; family conflicts; relationship difficulties; social isolation; problems with tobacco, alcohol and other drugs; missed work or school, or other problems related to work or school; legal and financial problems; poverty and homelessness; self-harm and harm to others, including suicide or homicide; weakened immune system, so your body has a hard time resisting infections; heart disease and other medical conditions.

Such neurobehavioral phenotypes, including associated neural areas, may be elucidated using, for example, noninvasive neuroimaging methods.

A range of neuroimaging types is available, such as, structural magnetic resonance imaging (MRI), resting-state or task-based functional MRI (fMRI), diffusion weighted imaging (DWI), positron emission tomography (PET), electroencephalography (EEG), magnetoencephalography (MEG), electrocorticography (ECoG), etc., from nonpublic and public databases.

These neuroimaging techniques can produce brain maps, i.e., an assignment of a numerical value to each location in the brain reflecting the magnitude of a feature, which can be associated with a neurobehavioral phenotype. Examples of features assessed or quantified by neuroimaging techniques include, but are not limited to, MR-based (e.g. activation in response to a cognitive paradigm, geometry of the brain, diffusivity properties of tissue such as diffusion-weighted imaging, relationships between signals across time such as functional connectivity analyses, individual difference maps between any imaging measure and behavioral measures, etc.), non-MR-based (e.g. electrophysiological recordings via EEG, MEG, ECoG, changes in spectra properties of power, oscillatory signatures, etc.), stimulation-based brain changes in any of the aforementioned techniques such as transcranial magnetic stimulation (TMS), pharmacological manipulations of aforementioned MR-based and non-MR-based signals, etc.

Data sources include neuroimaging maps from public and private databases or future studies. Examples include, but are not limited to, The Human Connectome Project Database, The National Institute of Mental Health Data Archive, and the Neuroimaging Informatics Tools and Resources Clearinghouse, which are further described below.

The Human Connectome Project Database. The Human Connectome Project (HCP) has tackled key aspects of this challenge by charting the neural pathways that underlie brain function and behavior, including high-quality neuroimaging data in over 1100 healthy young adults. Using greatly improved methods for data acquisition, analysis, and sharing, the HCP has provided the scientific community with data and discoveries that greatly enhance our understanding of human brain structure, function, and connectivity and their relationships to behavior. The 'HCP-style' neuroimaging approach is generalizable and is being applied to other projects as well.

The National Institute of Mental Health Data Archive (NDA). NDA makes available human subjects data collected from hundreds of research projects across many scientific domains. The NDA provides infrastructure for sharing research data, tools, methods, and analyses enabling collaborative science and discovery. De-identified human subjects data, harmonized to a common standard, are available to qualified researchers. Summary data is available to all.

Neuroimaging Informatics Tools and Resources Clearinghouse (NITRC). NITRC is a free one-stop-shop collaboratory for science researchers that need resources such as neuroimaging analysis software, publicly available data sets, or computing power. Since its debut in 2007, NITRC has helped the neuroscience community to use software and data produced from research that, before NITRC, was routinely lost or disregarded, to make further discoveries.

Here the inventors leveraged neuroimaging phenotype maps derived from the publically available Human Connectome Project (HCP) database. Maps from this dataset relate fMRI activity to neurobehavioral phenotypes. It is contemplated that the utility of the present platform will increase upon increasing interface with a database of phenotype maps.

The HCP dataset includes resting-state and task-based fMRI data and a range of demographic, behavioral measures from a large number of healthy subjects. Barch D M et al., *Function in the Human Connectome: Task-fMRI and Individual Differences in Behavior*, NEUROIMAGE, 80: 169-189, Oct. 15 (2013). HCP-derived maps used here provide group-level activation (N=334) across, for example, the following cognitive tasks: (i) Motor Strip Mapping Task (Right versus left toe movements or finger movements; tongue movements). See Bizzi A. et al., *Presurgical functional MR imaging of language and motor functions: validation with intraoperative electrocortical mapping*, RADIOLOGY, 248: 579-589 (2008); Morioka T. et al., *Comparison of magnetoencephalography, functional MRI, and motor evoked potentials in the localization of the sensory-motor cortex*, NEUROLOGICAL RESEARCH, 17:361-367 (1995); (ii) Language Processing Task. ((a) Auditory sentence presentation with detection of semantic, syntactic and pragmatic violations; versus (b) auditory story presentation with comprehension questions versus math problems.) See Binder J R et al., *Mapping anterior temporal lobe language areas with fMRI: a multicenter normative study*, NEUROIMAGE, 54:1465-1475 (2011); Ditman T. et al., *An investigation of concurrent ERP and self-paced reading methodologies*, PSYCHOPHYSIOLOGY, 44:927-935 (2007); and Kuperberg G R et al., *Neuroanatomical distinctions within the semantic system during sentence comprehension: evidence from functional magnetic resonance imaging*, NEUROIMAGE, 40:367-388 (2008); (iii) Working Memory & Cognitive Control Task. (Alternating blocks of 0-back and 2-back working memory; faces, nonliving man-made objects, animals, body parts, houses, or words. N-back Task (2-back versus 0-back) embedded in Category Specific Representation Task). See Drobyshevsky A. et al., *A rapid fMRI task battery for mapping of visual, motor, cognitive, and emotional function*, NEUROIMAGE, 31:732-744 (2006) ("Drobyshevsky"); and Caceres A. et al., *Measuring fMRI reliability with the intra-class correlation coefficient*, NEUROIMAGE, 45:758-768 (2009); and Emotion Processing. ((i) Valence Judgments (negative and neutral pictures from IAPS) versus (ii) Hariri Hammer Task). See Drobyshevsky; Phan K L et. al., *Real-time fMRI of corticolimbic brain activity during emotional processing*, NEUROREPORT, 15:527-532 (2004); Manuck S B et al., *Temporal stability of individual differences in amygdala reactivity*, AM. J. PSYCHIATRY, 164:1613-1614 (2007a); Hariri A R et al., *The amygdala response to emotional stimuli: a comparison of faces and scenes*, NEUROIMAGE, 17:317-323 (2002).

Additional sources of maps could be derived from meta-analytic sources, such as the Neurosynth online database. Yarkoni et al., *Large-scale automated synthesis of human functional neuroimaging data*, NAT. METHODS 8:665-70 (2011) ("Yarkoni"). Neurosynth generates statistical maps from automated meta-analysis of published fMRI studies. One can download from the Neurosynth site a map whose values are the statistical strength of modulation related to a given term, such as "working memory," derived from synthesis of hundreds of fMRI studies labeled with that term. There are two main caveats with using Neurosynth data. First, they are thresholded maps, and therefore lacking values for large portions of the brain. Unthresholded statistical maps, which have full coverage, would be better suited for gene-map correlations. Second, these maps are given in the volumetric Neuroimaging Informatics Technology Initiative (NIfTI) format. The present inventors found that conversion of these maps to the Connectivity Informatics Technology Initiative (CIFTI) format is possible, but the spatial resolution may be coarse because such maps are not inherently CIFTI-optimized. Nonetheless, it is contemplated that maps related to terms of interest may be selected for use with the present tools and methods. For instance, maps related to the following terms: working memory, cognitive control, motivation, decision-making, and emotional processing may be extracted.

Collections of current neuroimaging maps are heterogeneous. As one illustrative example of regional neural specificity in clinical neuroimaging, the present inventors studied the pattern of cortical dysconnectivity in schizophrenia with fMRI. The present inventors found that patients with schizophrenia exhibited an overall increase in the covariance of resting-state BOLD signals. Yang et al., *Functional hierarchy underlies preferential connectivity disturbances in schizophrenia*, PROC. NATL. ACAD. SCI. USA 113:E219-28 (2016) ("Yang"). Strikingly, this neuroimaging-derived map of increased covariance was not uniform across cortex, but preferentially elevated in association cortex relative to sensory cortex, which are consistent with other findings revealing preferential alterations to higher-order association regions. Whitfield-Gabrieli et al, *Hyperactivity and hyperconnectivity of the default network in schizophrenia and in first-degree relatives of persons with schizophrenia*, PROC. NATL. ACAD. SCI. USA 106:1279-84 (2009) ("Whitfield-Gabrieli"); Baker et al., *Disruption of cortical association networks in schizophrenia and psychotic bipolar disorder*, JAMA PSYCHIATRY 71:109-18 (2014) ("Baker"). This provides an example that a neuroimaging map of clinical relevance (here, resting-state dysconnectivity in schizophrenia) shows potentially important regional variation across cortex. Currently, no neuro-informatics platform links, extrapolates, associates, construes, or derives from, these patterns with variation in biophysical properties such as gene expression. Targeted drug discovery for neurobehavioral phenotypes could be better informed by neuroimaging maps related to: particular functions (e.g. activation during working memory, or reward processing), symptom dimensions (e.g. negative symptoms in schizophrenia), or data-driven "biotypes" within a categorical disorder. Drysdale.

Gene Expression and Mapping

Genes code for proteins, e.g., receptor subunits, which may be targets of drugs or otherwise involved in effects of therapeutics. Gene expression is remarkably heterogeneous across different brain locations, across the lifespan, across different disease stages, different treatment stages. Also, some genetic traits are fully penetrant (i.e. all individuals that carry a mutation present with the phenotype) versus not fully penetrant (i.e. proportion of individuals carrying a particular variant (or allele) of a gene (the genotype) that also express an associated trait (the phenotype) is not 100%). This distinction matters because in the case of a fully penetrant mutation that gene may be a high candidate target. That said a further distinction needs to be drawn between genes that are associated with risk of developing a given phenotype and genes that code for potential therapeutic targets. It is contemplated that maps related to fully penetrant, not fully penetrant, or downstream therapeutic target genes of interest may be selected for use with the present tools and methods.

Gene expression can be measured through techniques including DNA microarray, in situ hybridization and RNA sequencing. Gene expression in brain structures, e.g. cortex, can be measured at multiple levels of spatial resolution, including bulk tissue, specific cortical layers, and individual cells.

Data sources for gene expression across brain locations, across humans and other species, include the Allen Human Brain Atlas (AHBA) (gene expression across the whole adult human brain); the Allen Mouse Brain Atlas (gene expression across the whole adult mouse brain); the Allen Developing Mouse Brain Atlas (gene expression across the mouse brain at multiple stages of development); the BrainSpan Atlas of the Developing Human Brain (transcriptome of the human brain at multiple stages of development); the NIH Blueprint Non-Human Primate (NHP) Atlas (gene expression data and neuroanatomical data from the developing rhesus macaque brain); the Aging, Dementia and Traumatic Brain Injury (TBI) Study (neuropathologic, molecular and transcriptomic characterization of brains of control and TBI exposure cases); the Allen Cell Types Database (single-cell level gene expression from neuronal cell types); and the BrainCloud database (transcriptome in human prefrontal cortex across the lifespan).

Collections of current gene expression maps are also heterogeneous. To achieve regional specificity of pharmaceutical effects, regional variation in expression of drug target across brain areas is needed. These patterns can be revealed by analysis of the expression of genes coding proteins involved in the drug targets.

The AHBA is a publicly available database of gene expression from around 30,000 genes represented by about 60,000 microarray probes, sampled from hundreds of brain locations (cortical and subcortical) from six subjects. Hawrylycz et al., *Canonical genetic signatures of the adult human brain*, NAT. NEUROSCI. 18:1832-44 (2015) ("Hawrylycz 2015"). The AHBA database provides a unique opportunity to characterize the regional variation in drug targets. Indeed, gene expression is remarkably heterogeneous across different brain regions. For instance, there is strong variation in the expression of dopamine signaling pathway genes across cortical and subcortical brain regions. See e.g., Hawrylycz et al., *An anatomically comprehensive atlas of the adult human brain transcriptome*, NATURE 489:391-9, FIG. 2 (2012) ("Hawrylycz 2012"). Even within neocortex, gradients of gene expression reveal the coordinated specialization of microcircuitry, such as from primary sensory to association cortex. Burt et al., *Hierarchy of transcriptomic specialization across human cortex captured by structural neuroimaging topography*, NATURE NEUROSCIENCE 21:1251-9 (2018) ("Burt"). Prior studies using the AHBA data had already demonstrated the feasibility of integrating gene expression and neuroimaging maps. Cortical regions with similar gene expression profiles are more likely to be structurally interconnected and more likely to have high functional connectivity (as characterized by resting-state BOLD signals). (Hawrylycz 2015; Richiardi et al., *Correlated gene expression supports synchronous activity in brain networks*, IMAGEN consortium, SCIENCE 348:1241-4 (2015) ("Richiardi"). Studies have also found that risk genes for schizophrenia are expressed in meaningful patterns related to neurodevelopment, and to schizophrenia-related alterations of diffusion-MRI-derived structural connectivity. Whitaker et al., *Adolescence is associated with genomically patterned consolidation of the hubs of the human brain connectome*, NSPN Consortium, PROC. NATL. ACAD. SCI. USA 113:9105-10 (2016) ("Whitaker"); Romme et al., *Connectome disconnectivity and cortical gene expression in patients with schizophrenia*, BIOL. PSYCHIATRY (2016) ("Romme"). These prior studies, as well as the inventors' analyses, support the validity of the AHBA dataset as a high-quality source of meaningful gene expression variation across the human brain. The present tools and methods go beyond these prior studies to bi-directionally identify genes and neurobehavioral phenotypes based on quantitative alignment of their spatial maps.

Here, the inventors used the AHBA dataset. The AHBA dataset contains gene expression levels across the human brain, for about 30,000 genes represented by about 60,000 microarray probes, sampled from hundreds of regions in the left hemisphere (cortical and subcortical), from six subjects. Hawrylycz 2012; Hawrylycz 2015. In the terminology used by the AHBA, a "sample" is a gene expression measurement from a specific location in the brain. For a gene of interest, a microarray probe (specific DNA sequence) is selected for which expression values are measured.

The present tools and methods may include three levels for analysis of cortical gene expression data: (1) sparse samples or specific locations; (2) interpolated dense map or across an entire continuous map at its native (i.e., dense) resolution; and (3) a map parcellated into discrete regions or areas. Map coordinates for locations of expression can be transformed into different neuroimaging brain atlases (e.g., the Montreal Neurological Institute (MNI) atlas). The level of sparseness used can be selected based on resolution of neurobehavioral phenotype mapping data or area of interest for which one seeks to quantify the gene expression profile.

The AHBA dataset provides MNI coordinates for each sample. For samples in cortex, the method maps the coordinates to the nearest grayordinate in CIFTI cortical surface. There are two ways to achieve this. A courser way would involve mapping of the AHBA provided MNI coordinates for each location of gene expression onto a common atlas. The second more precise method would involve computing a complete segmentation of all gray and white matter for each individual subject for whom gene expression data exists. Then these segmentations would be used to compute cortical surface boundaries for each subject via automated tools such as FreeSurfer (See e.g., Dale A M et al., *Cortical surface-based analysis I. Segmentation and surface reconstruction*, NEUROIMAGE, 9 (2), 179-194, 4931 (1999); Fischl B. et al, *Whole brain segmentation: Automated labeling of neuroanatomical structures in the human brain*, NEURON, 33 (3), 341-355, 3776 (2002); and Fischl B. et al, *Cortical surface-based analysis. II: Inflation, flattening, and a surface-based coordinate system*, NEUROIMAGE, 9 (2), 195-207 (1999)). In turn, the subject-specific 'native space' locations of gene expression would be mapped onto that subject's cortical surface mesh. In turn, the values on the mesh would then be transformed into a common atlas based on state-of-the-art surface-based registration methods (See above, and Anticevic A. et al., *Comparing surface-based and volume-based analyses of functional neuroimaging data in patients with schizophrenia*, NEUROIMAGE, 41(3):835-48, July 1 (2008); Glasser M F et al., *A multi-modal parcellation of human cerebral cortex*, NATURE, 536, 171-178 (11 Aug. 2016)).

For samples in sub-cortex, the AHBA-assigned label for the brain region may be used. Similarly to the second method described for cortex, an alternative method would involve computing a complete segmentation of all gray and white matter for each individual subject for whom gene expression data exists. Then these segmentations would be used to compute subcortical volume boundaries for each subject via automated tools such as FreeSurfer (Dale A M et al., *Cortical surface-based analysis I. Segmentation and surface reconstruction*, NEUROIMAGE, 9 (2), 179-194, 4931 (1999); Fischl B. et al, *Whole brain segmentation: Automated labeling of neuroanatomical structures in the human brain*, NEURON, 33 (3), 341-355, 3776 (2002) Fischl B. et al, *Cortical surface-based analysis. II: Inflation, flattening, and a surface-based coordinate system*, NEUROIMAGE, 9 (2), 195-207 (1999)). In turn, the subject-specific 'native space' locations of gene expression would be mapped onto that subject's subcortical volumes and transformed into a common atlas based on state-of-the-art registration methods (Anticevic A. et al., *Comparing surface-based and volume-based analyses of functional neuroimaging data in patients* with schizophrenia, NEUROIMAGE, 41(3):835-48, July 1 (2008); Glasser M F et al., *A multi-modal parcellation of human cerebral cortex*, NATURE, 536, 171-178 (11 Aug. 2016)).

Analyses can proceed at the sample level, using the sparse grayordinates to which AHBA samples are mapped.

The dense and parcellated maps require interpolation of gene expression values to all grayordinates in cortex. To perform this interpolation, multiple methods may be used. Our current method is to construct a Voronoi diagram, assigning each grayordinate to its nearest AHBA sample location; that sample's gene expression values are then given to those grayordinate. Other methods may be used, including weighted averaging based on exponential decay with increasing geodesic distance from the sample along the cortical surface (e.g. with characteristic length constant determined by the gene expression spatial autocorrelation structure). This provides the dense map. To produce a parcellated map, the dense map may be parcellated with a CIFTI-defined parcellation using, for instance, the Connectome Workbench software or any other matrix manipulation software that can read the CIFTI format (e.g. Matlab, R statistical computing environment, Octave, Python, etc.). For example, the new cortical parcellation from the HCP team may be used. Glasser et al., *A multi-modal parcellation of human cerebral cortex*, NATURE 536:171-8 (2016) ("Glasser"). For parcels that contain gene expression, one method is to assign the parcel value as an average of the samples within that parcel, which can be a weighted average (e.g., based on the samples' relative Voronoi diagram coverages within the parcel).

As noted, additional coordinates can be assigned to measurement sites by explicitly computing the cortical and subcortical segmentation of each individual subject contributing to the AHBA based on their high-resolution structural post-mortem scans. In turn, such segmentations can be leveraged to compute a cortical mesh and subcortical anatomical nucleus assignment. In turn, the mesh forms a surface along with proximity that can then be calculated for each individual subject, yielding a set of subject-specific coordinates. In turn, such a cortical surface mesh can be aligned across subjects to the group atlas using surface-based features. This also applies to subcortical locations of expression, which can be defined at the subject level based on their anatomy and in turn aligned to a given group atlas. Following this spatial transformation, each subjects' individual coordinates are brought into alignment. Next, analyses can proceed at the specific location level, using specific coordinates for gene expression at that location. Importantly, neuroimaging maps would also capture the relevant cortical and subcortical locations.

Conversely, the continuous "dense" and discrete "parcellated" maps require assigning a gene expression value to a given cortical location either the native resolution of a given dense map or into a given discrete parcel/area. Example methods for this assignment include: (1) assignment of value to a given map location based its proximity to the locations at which gene expression was measured, i.e., the gene expression measurement sites. This can be done via, for example, nearest neighbor assignment; e.g., through construction of a Voronoi diagram; (2) assignment by a weighted sum to a map location based on the proximity to the locations at which gene expression was measured; e.g., weighted by distance along cortical surface from the gene expression measurement sites; and (3) assignment by a weighted sum across gene expression measurement sites which are within parcel boundaries according to a given parcellation.

Subcortical gene expression data can be used to assign values to subcortical locations or regions. Methods for this assignment include labeling by neuroanatomical evaluation, weighted sum within a parcellation of subcortical regions, or other forms of anatomical or functional location assignment.

Further processing steps can be applied to gene expression data to remove extraneous biases and improve signal-to-noise before combination with the neurobehavioral phenotype mapping data. These steps can improve the reproducibility of the maps, which can be quantified by a stability metric across subjects. Example steps include: (1) expression values can be normalized within each subject (i.e., brain) before combining across subjects (e.g., via mean or median); (2) gene expression measurement sites can be filtered out on the basis of their exhibiting exceptionally low similarity with other measurement sites in their expression levels across genes; and (3) signal-to-noise of the spatial expression pattern can be improved through data processing techniques such as dimensionality reduction via principal component analysis (PCA).

The present inventors encountered a variety of complications in using the raw AHBA dataset, necessitating further preprocessing for use with the platform of the present tools and methods. These problems necessitate the development a number of additional pre-processing steps to remove extraneous biases and improve signal-to-noise. For instance, the present inventors found biases in the mean expression levels across AHBA samples which should be corrected. Best ways to combine data across the six subjects are also assessed, which requires de-meaning and normalizing data.

It is also noted that selection of probes for a given gene of interest is non-trivial. For many genes there are multiple probes, which can be selected based on their expression levels and overall coverage across samples. The present tools and methods test whether a probe or gene is suitable for analyses by characterizing it differential stability across subjects (i.e., the average between-subject correlation of expression values). Hawrylycz 2015. Also, the present tools and methods may use differential stability to select subsets of subjects with stable across-subject expression maps for further analysis. Careful characterization of these steps is expected to greatly improve the ability to get meaningful results from the AHBA dataset. For instance, the present inventors filtered out probes whose coverage across cortical parcels (defining coverage scores) were below a threshold percentage and therefore not well suited to interpolation to form dense or parcellated gene expression maps. If two probes were available for a gene, each with acceptable coverage and differential stability scores, the selected probe was set as the one with maximum gene expression variance. If three or more acceptable probes were available, the selected probe is the one with the highest similarity to the other probes, as it is most highly representative among available gene probes.

For gene expression datasets derived from DNA microarray measurements, selection of the microarray probe for a gene of interest is important. Probes are selected on the basis of multiple factors, including their coverage across brain regions, and their consistency of expression patterns across subjects (e.g., post-mortem human or animal brains). Example DNA microarray probes in the AHBA (made by Agilent) are: A_23_P40262 (for PDYN), A_23_P132619 (for OXTR), A_23_P169061 (for OPRK1), A_24_P382579 (for OXT), A_23_P9883 (for AVP), and A_23_P345564 (for OPRL1]. Multiple selected probes can be combined in a weighted sum to improve signal-to-noise, e.g., by using the first principal component from PCA, by using the mean or median value across probes, or by using the most representative probe through some central tendency measure. The probe information can be obtained through, for example, publically available databases or optimized through future experiments.

Computational Framework

The overall computational framework for the present platform is shown schematically in FIG. 1. Briefly, embodiments described herein relate to correlating neurobehavioral phenotypes (e.g., a disorder, symptom, cognitive process, etc.) and genes (or their associated drugs or drug targets) by pre-processing brain mapping data and gene expression data, and computing similarities between a brain map related to a neurobehavioral phenotype (as can be produced by human neuroimaging) and a brain map of expression values for a gene.

Figure 1B:
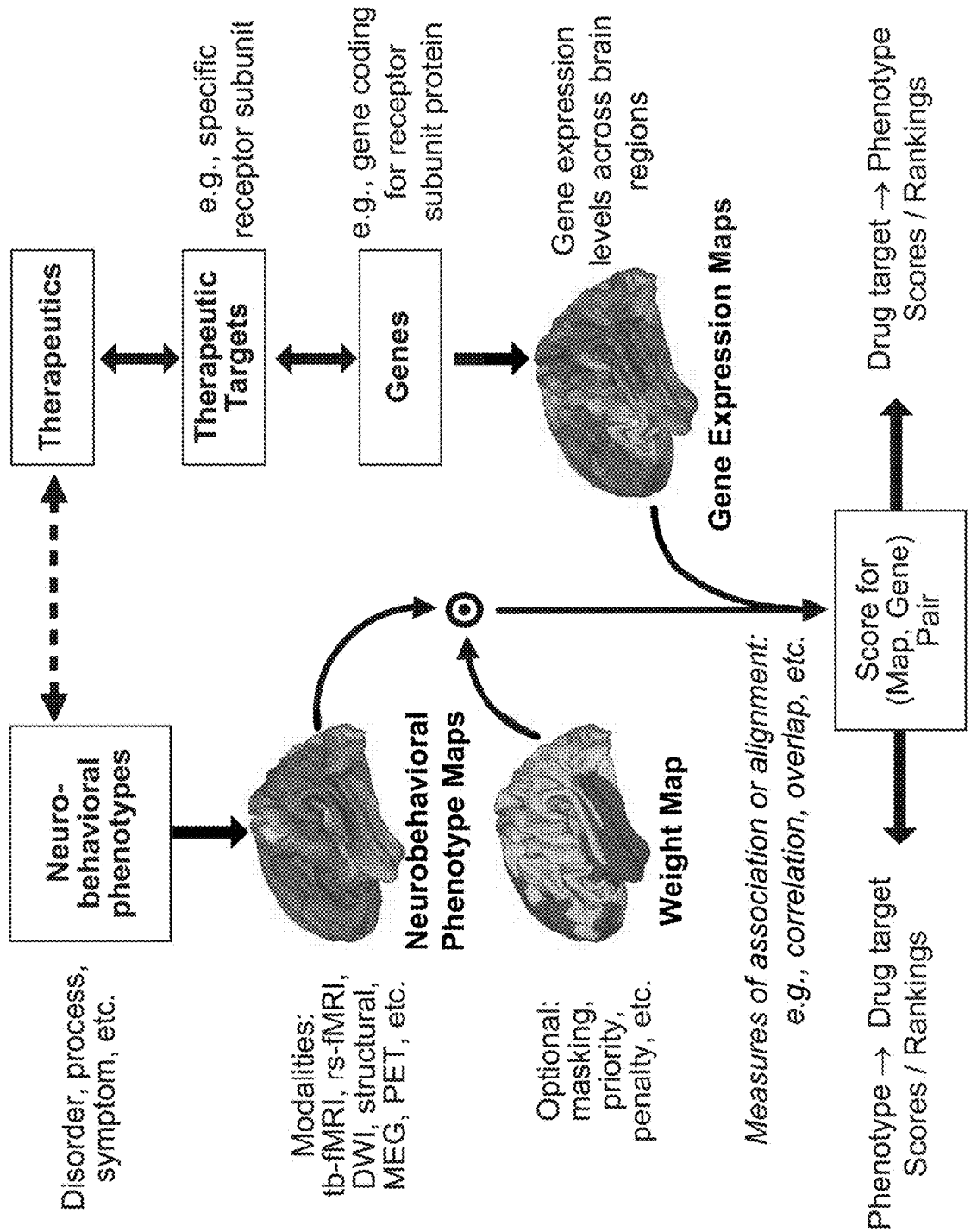

In general, the platform involves two paths, which are represented as path 110 and path 120 in FIGS. 1A and 1B.

Path 110 of the schematic platform depiction begins with a list of one or more neurobehavioral phenotypes 112. As described in more detail herein, the process may begin with a selected neurobehavioral phenotype to identify or predict a gene or drug target, or it may begin with a selected gene or drug target to identify or predict a neurobehavioral phenotype. A set of neurobehavioral phenotype maps 114 (i.e., neurophenotype topographies) are generated from neurobehavioral phenotype mapping data from one or a plurality of neural images for one or more people. These neurobehavioral phenotype maps 114 reflect characteristics of disorders, symptoms, and cognitive processes at the level of whole-brain measurement or across select locations or brain regions. Such neurobehavioral phenotype maps 114 can be derived for use with the genotype topography and neurophenotype topography-based methods described herein from a range of neuroimaging modalities: task-based fMRI, resting-state fMRI, DWI, structural, EEG, MEG, PET maps, etc. These neurobehavioral phenotype maps are labeled by their associated neurobehavioral phenotypes. The neurobehavioral phenotype mapping datasets used to generate the neurobehavioral phenotype maps 114 can therefore come from a variety of sources as well as from publicly available databases. Therefore, the system can interface with a database relating an ontology of neurobehavioral phenotypes with neuroimaging maps.

In various embodiments, the system utilizes neuroimaging maps that reflect neurobehavioral phenotype characteristics either at a whole-brain level or across select locations or brain regions as the neurobehavioral phenotype maps. The neurobehavioral phenotype maps can be derived by precomputing and/or gathering information from prior sources or can be empirically generated in new observational and experimental work across animal and human studies.

In some embodiments, optional weighting and masking 116 of neurobehavioral phenotype maps 114 may be employed. That is, for optional weighting, a weight value may be assigned for each brain location or region. Such weighting allows for prioritization of particular locations or brain regions, penalization of expressions in certain locations or brain regions, etc. For example, prioritizing particular brain regions may include assigning those regions with a weight above a threshold, and assigning other brain regions with a weight below the threshold. Also, optional masking may be accomplished by weighting that is used to mask or remove information from specific locations or brain regions, such as by assigning weights to zero or below another, lower threshold. Masking allows flexibility of assessing alignment of neurobehavioral phenotype maps with gene expression maps prioritization of particular brain structures or only within certain brain structures, rather than at the whole-brain level, e.g., only within cortex (masking out subcortical structures).

For example, the flexibility of the neurobehavioral phenotype maps 114 can be extended by combining it with an optional weight map, in which a weight value is defined for each brain region as part of the present genotype topography and neurophenotype topography-based methods. The weight map then can be used in calculation of the alignment measure, e.g., via the weighted Pearson correlation coefficient. This allows flexible implementation of operations such as masking out certain brain regions, giving priority to some regions over others, penalizing expression in certain regions, etc. The neurobehavioral phenotype maps 114 and weight maps are then contacted with and used for comparison to the gene expression maps 128.

Path 120 of the diagram, aligns therapeutic action related to the molecular targets of select therapeutics (e.g., drugs targeting the specific neurotransmitter receptors and their subunits), which are encoded by specific genes 126. The gene expression maps 128 (i.e., genotype topographies) characterize the differential expression of specific genes 126 across the brain. These gene expression maps 128 may be computed from the AHBA dataset and may result for pre-processed gene mapping information. The proteins encoded by these genes 126, and the biochemical pathways in which they are involved, can be linked with specific drug targets 124, and in turn with specific drugs 122 or therapeutics. Thus, the present platform may create new gene expression maps (i.e., genotype topographies) showing linkage with specific genes, associated drug targets or specific drugs. The system may interface with a database relating drugs 122 and drug targets 124 with genes 116.

In some embodiments, these two paths are used as input and contacted and correlated to define one or more phenotype-gene pair topographies for a given neurobehavioral phenotype (i.e., one or more phenotype-gene pairs for a same phenotype with different genes). A numerical score 130 is generated for each phenotype-gene pair topography for each phenotype-gene pair based on the contacting of data and alignment of the corresponding neurobehavioral phenotype map with the respective gene expression map.

For example, weighted neurobehavioral phenotype maps (i.e., neurophenotype topographies) and gene expression maps (genotype topographies) may be contacted and compared to define a corresponding phenotype-gene pair topography for a phenotype-gene pair, and a score reflecting the level of association is calculated for such maps. The numerical score for a given phenotype-gene pair may be based on the contact and alignment of the weighted neurobehavioral phenotype map with the gene expression map, and can be computed as the correlation of the map values across regions. Definition and characterization of the brain region or regions contacted, correlated, or aligned between the neurobehavioral phenotype map data and the gene expression map data results in a phenotype-gene pair topography for that phenotype-gene pair. This score can be derived from a measure of statistical association (e.g., correlation calculation or other measures of shared variance) with stronger associations ranked higher. Higher associations indicate stronger relationships between neurobehavioral phenotype maps and gene expression maps, suggesting a stronger possible link between associated therapeutic effects and neurobehavioral phenotypes. To assess this score, a measure of statistical significance or confidence intervals is also generated and provided.

In other embodiments, these two paths are used as input and contacted and correlated to define one or more gene-phenotype pair topographies for a given gene (i.e., one or more gene-phenotype pairs for a same gene with different phenotypes). A numerical score 130 is generated for each gene-phenotype pair topography for each gene-phenotype pair based on the contacting of data and alignment of the corresponding gene expression map with the respective neurobehavioral phenotype map. Similar to above, weighted neurobehavioral phenotype maps (i.e., neurophenotype topographies) and gene expression maps (genotype topographies) may be contacted and compared to define a corresponding gene-phenotype pair topography for a gene-phenotype pair, and a score reflecting the level of association is calculated for such maps.

In other embodiments, and not illustrated in FIG. 1, path 120 may be used as input and contacted and correlated to define one or more gene-gene pair topographies for a given gene (i.e., one or more gene-gene pairs for a same gene with different other genes). A numerical score 130 is generated for each gene-gene pair topography for each gene-gene pair based on the contacting of data and alignment of the corresponding gene expression maps with each other. Similarly, gene expression maps (genotype topographies) (which may be weighted or masked) may be contacted and compared to define a corresponding gene-gene pair topography for a gene-gene pair, and a score reflecting the level of association is calculated for such maps.

In various embodiments, the outputs of the platform comprise neuroimaging data files of all computed maps or other information and data in tangible, audible, or other formats. This includes maps characterizing in which regions the neurobehavioral phenotype map and gene expression map are contacted and aligned (i.e., a pair topography) and contacted and misaligned. Misaligned neurobehavioral phenotype map and gene expression maps can provides insight into potential "off-target" circuit effects. For visualization, maps data files may be compatible with Human Connectome Project (HCP) Connectome Workbench software. The outputs may also include identification of genes (e.g., when scoring phenotype-gene pairs or gene-gene pairs) or neurobehavioral phenotypes (e.g., when scoring gene-phenotype pairs). In some embodiments, the output may be a highest scoring pair or those pairs with a score above a threshold value.

In one embodiment, all brain maps (neuroimaging and gene expression), and the present inventive platform may use the new CIFTI file format for neuroimaging data utilized by the HCP. Glasser. In contrast to the purely volumetric NIfTI format, CIFTI represents cortex as a geometrically faithful two-dimensional mesh, and subcortical samples as volumes, collectively comprising about 95,000 grayordinates. The present inventors integrated legacy NIfTI data with CIFTI-based analyses to allow integration of the present inventive platform with existing data, such as large neuroimaging databases, as well as emerging CIFTI-compliant datasets.

CIFTI-based analyses have several advantages, including superior management and alignment of cortical folding using surface-based analysis, which minimizes signal bleed across sulci. Anticevic et al., *Comparing surface-based and volume-based analyses of functional neuroimaging data in patients with schizophrenia*, NEUROIMAGE 41:835-48 (2008) ("Anticevic"); Glasser. CIFTI-style formats are highly flexible and able to represent 'matrix-level' information under parcellation. As described herein, the CIFTI format is advantageous for working with gene expression data, as it allows surface-based interpolation from discrete samples onto a dense cortical mantle. Furthermore, CIFTI is compatible with visualization and analysis in the HCP Connectome Workbench software, which the present inventive platform may use for map visualization.

The present inventive platform requires improvements in statistical analysis. As described above, proper analysis of AHBA gene expression data will require substantial pre-processing to support interpretable results. For instance, characterizing differential stability will allow us to distinguish whether a low gene-map correlation value is due to dissimilar maps or just due to poor differential stability. For a given gene, selecting subsets of subjects with high differential stability may improve the signal-to-noise relative to combining all subjects.

Another important issue involves assessing the probability observed correlations could occur by chance, i.e., their statistical significance. A simple correlation (e.g., Pearson or Spearman) provides an associated parametric p-value. However, this p-value is derived under the assumption of statistical independence across data points (here, brain regions); this independence assumption may be violated in different brain maps because the measures are spatially autocorrelated across brain regions. The present inventors may use statistical tests for spatial autocorrelation (e.g., Moran's I, Mantel's test) to evaluate the impact of autocorrelation on inferences of statistical significance for correlations scores. To correct for autocorrelation-induced biases in model inference, the present inventors can calculate statistical significance with a Spatial Autoregression (SAR) model. These statistical and data analytic advances may further improve the inferential power of the platform.

Figure 2:
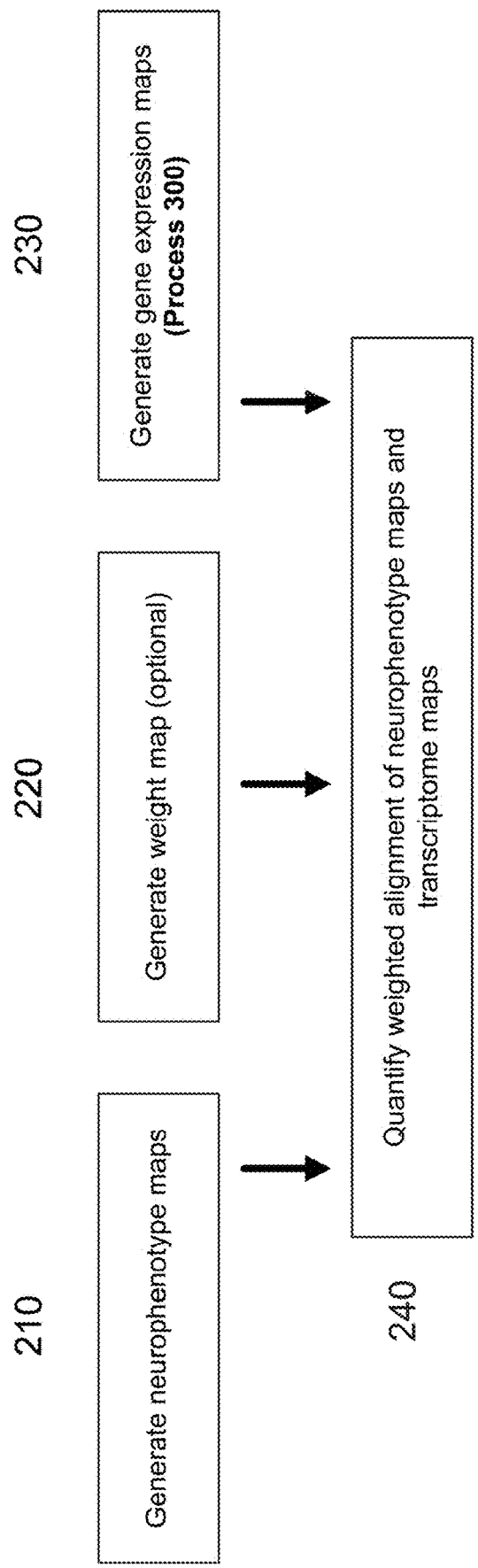
FIGS. 2-4 are block diagrams of a process for performing the computation framework relating to correlating phenotype maps and gene expression map between neurobehavioral phenotypes to drug targets.

Turning to FIG. 2, the processing steps involve the generation of three types of maps: neurobehavioral phenotype maps (i.e., neurobehavioral phenotype topographies), weight maps (optionally), and gene expression maps (i.e., genotype topographies). These maps are contacted and used to define one or more pair topographies for phenotype-gene pairs, gene-phenotype pairs, or gene-gene pairs. The maps are also used to calculate scores quantifying a weighted measure of alignment between neurobehavioral phenotype maps and gene expression maps for corresponding pairs. Processing begins with the generation of behavioral neurophenotype maps (box 210) and gene expression maps (box 230). The generation of the behavioral neurophenotype maps is discussed in more detail above in the "Neurobehavioral phenotypes and mapping" sub-section. The generation of the gene expression maps is discussed in more detail above in the "Gene expression and mapping" sub-section and in more detail below in conjunction with FIGS. 3 and 4.

In some embodiments, weight or masking maps may be optionally generated (box 220), which is described in more detail above with respect to optional weighting and masking 116 in FIGS. 1A and 1B.

Figure 3:
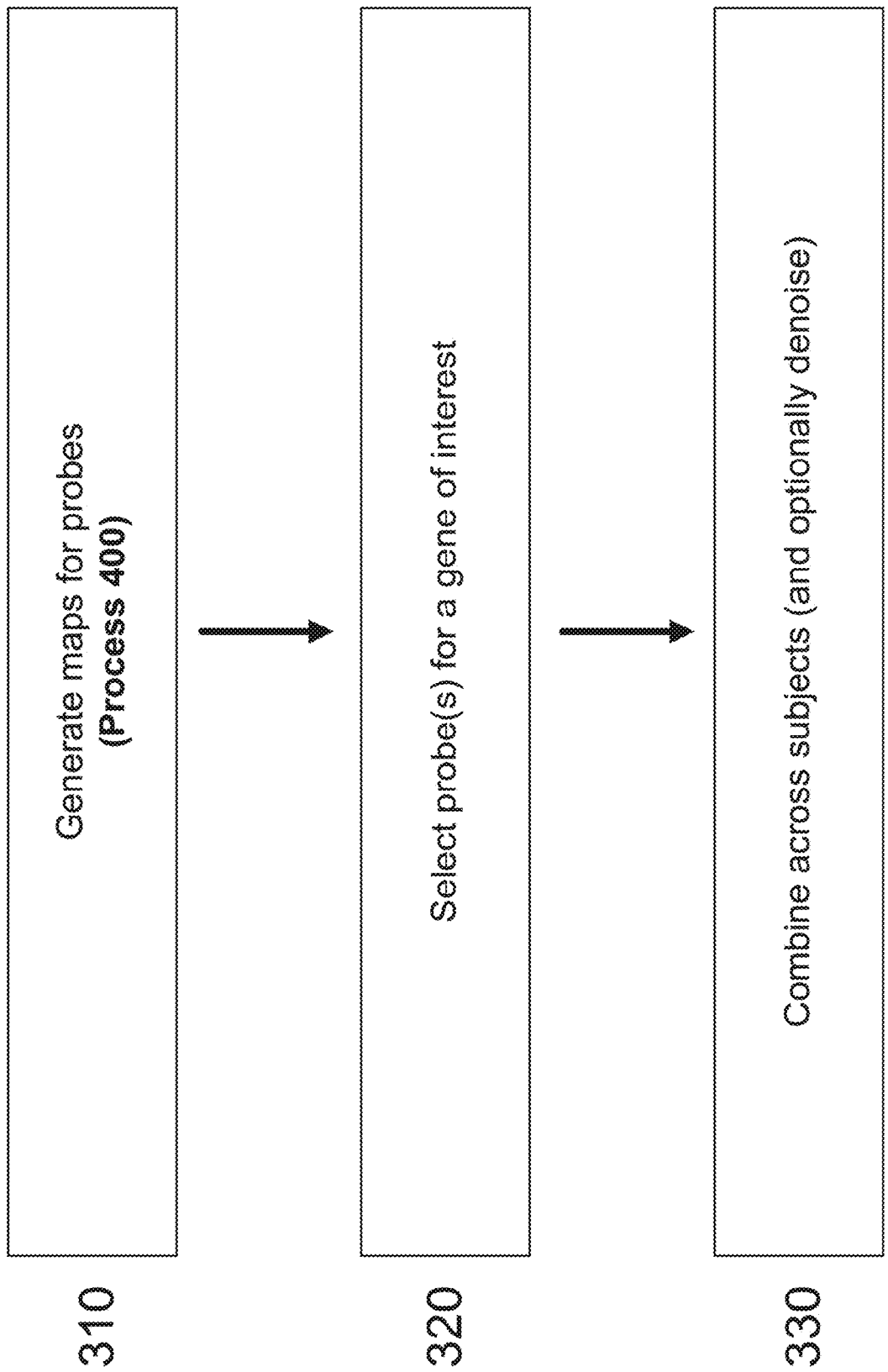

Generation of gene expression maps (230) from the AHBA dataset involves multiple steps (FIG. 3). For each subject, brain maps are generated for gene expression probes (310), which involves multiple stages of data processing (shown in more detail below in conjunction with FIG. 4).

As denoted in Box 320 (FIG. 3), for each gene of interest, one or more representative probes is selected for each subject. Probe-gene associations can be obtained through, for example, publically available databases or optimized through experimental trials. For many genes there are multiple associated probes, which can be selected based on their expression levels and overall coverage across samples. The present tools and methods test whether a probe or gene is suitable for analyses by characterizing its differential stability across multiple subjects (i.e., the average between-subject correlation of expression values). Hawrylycz 2015. Also, the present tools and methods may use differential stability to select subsets of subjects with stable across-subject expression maps for further analysis.

Careful characterization of these steps is expected to greatly improve the ability to get meaningful results from the AHBA dataset. For instance, in some embodiments, probes whose coverage across cortical parcels (defining coverage scores) are below a threshold percentage and therefore not well suited to interpolation to form dense or parcellated gene expression maps may be filtered out. If two probes are available for a gene, each with acceptable coverage and differential stability scores, the selected probe can be set as the one with maximum gene expression variance. If three or more acceptable probes are available, the selected probe is the one with the highest similarity to the other probes, as it is most highly representative among available gene probes.

For gene expression datasets derived from DNA microarray measurements, the microarray probe for a gene of interest may be selected on the basis of multiple factors, including their coverage across brain regions, and their consistency of expression patterns across subjects (e.g., post-mortem human or animal brains). Example DNA microarray probes in the AHBA (made by Agilent) are: A_23_P40262 (for PDYN), A_23_P132619 (for OXTR), A_23_P169061 (for OPRK1), A_24_P382579 (for OXT), A_23_P9883 (for AVP), and A_23_P345564 (for OPRL1]. Multiple selected probes can be combined in a weighted sum to improve signal-to-noise, e.g., by using the first principal component from PCA, by using the mean or median value across probes, or by using the most representative probe through some central tendency measure. The probe information can be obtained through, for example, publically available databases or optimized through future experiments.

As denoted in Box 330 (FIG. 3), a group-level gene expression map for a gene of interest can be computed by contacting and combining the individual-level gene expression maps across subjects. This step can be performed by averaging, and improved through additional processing steps. For instance, each subject-level gene expression profile can be z-scored before computing group-level expression profiles, which are obtained by computing the mean across subjects which are assigned a probe for that gene. Subjects may be excluded from inclusion if too few of their samples contained values for probes associated with that gene, as determined by a threshold number. Finally, group-level expression profiles may be z-scored across all areas for each gene. Other optional steps in computing group-level maps may include preferential weighting across subjects, for each parcel, based on whether the parcel contained a sample for each subject.

Figure 4:
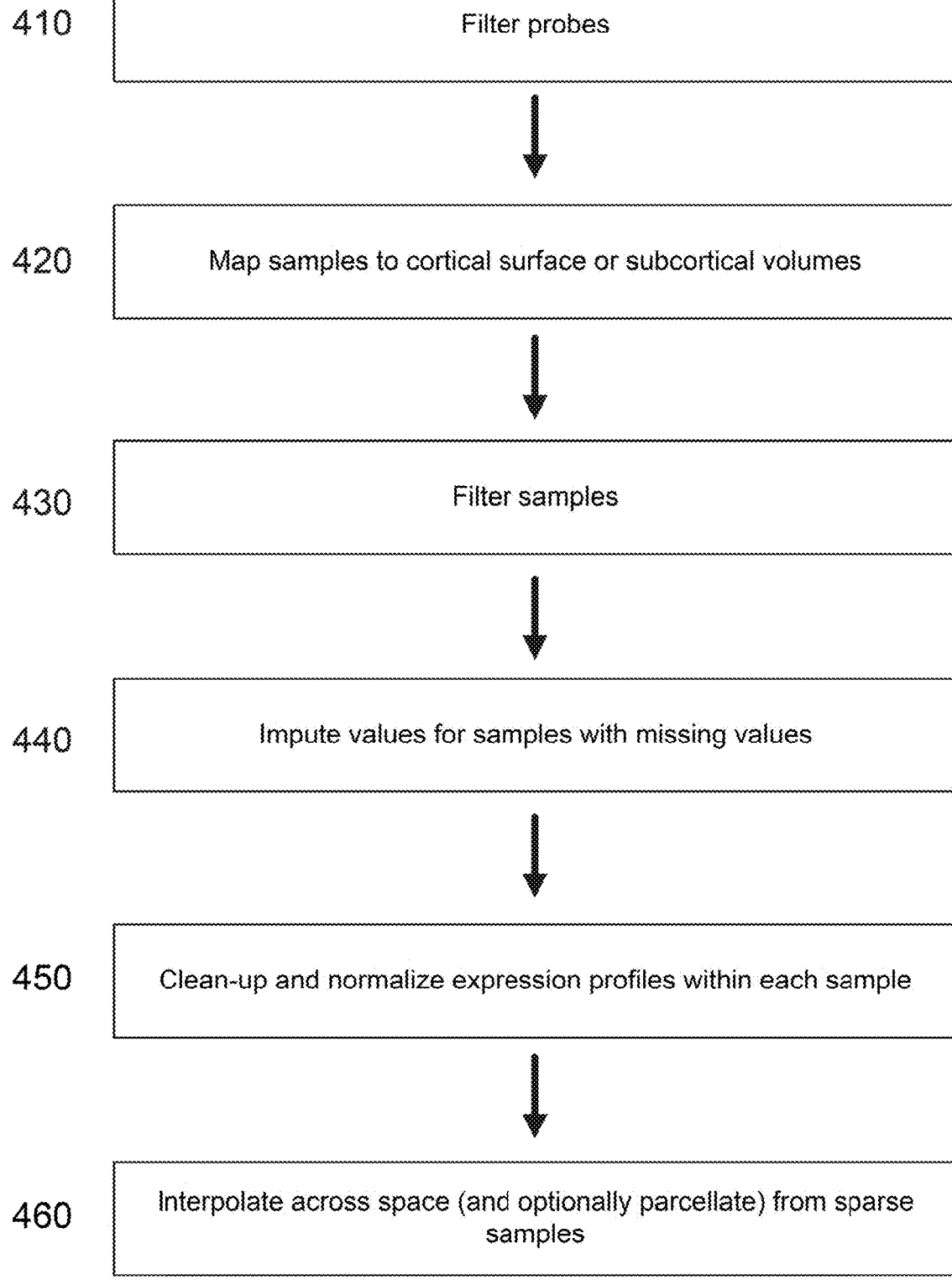

Turning to FIG. 4, gene probes are filtered, so that they correspond to known genes, as denoted in Box 410. For instance, probes without a valid Entrez Gene ID can be excluded.

In general, embodiments include three levels for analysis of cortical or subcortical gene expression data: (1) sparse samples or specific locations; (2) interpolated dense map or across an entire continuous map at its native (i.e., dense) resolution; and (3) a map parcellated into discrete regions or areas. Map coordinates for locations of expression can be transformed into different neuroimaging brain atlases (e.g., the Montreal Neurological Institute (MNI) atlas). The level of sparseness used can be selected based on resolution of neurobehavioral phenotype mapping data or area of interest for which one seeks to quantify the gene expression profile.

As denoted in Box 420 (FIG. 4), gene expression samples are mapped to locations in brain structures from their volumetric imaging space. The AHBA dataset provides MNI coordinates for each sample.

In some embodiments, for samples in cortex, there are two ways to map the coordinates to the nearest grayordinate in CIFTI cortical surface. A courser way may involve mapping of the AHBA provided MNI coordinates for each location of gene expression onto a common atlas. A second, more precise method, may involve computing a complete segmentation of all gray and white matter for each individual subject for whom gene expression data exists.

For example, a sample from cortex can be mapped to a CIFTI-format surface grayordinate by selecting the grayordinate with minimum Euclidian distance between the stereotaxic MNI coordinates for that sample and the coordinates of grayordinate vertices in each subject's native cortical surface mesh.

Single-subject surface registration for each of the six subjects in the AHBA can be performed following a procedure adapted from the HCP's minimal preprocessing pipelines. Briefly, the T1w image can be first rigidly aligned to the MNI coordinate axes to produce a native space volume, which can be then nonlinearly registered to the standard MNI template using FSL's FLIRT and FNIRT. Cortical surface boundaries for each subject can be computed via automated tools such as FreeSurfer (See e.g., Dale A M et al., *Cortical surface-based analysis I. Segmentation and surface reconstruction*, NEUROIMAGE, 9 (2), 179-194, 4931 (1999); Fischl B. et al, *Whole brain segmentation: Automated labeling of neuroanatomical structures in the human brain*, NEURON, 33 (3), 341-355, 3776 (2002); and Fischl B. et al, *Cortical surface-based analysis. II: Inflation, flattening, and a surface-based coordinate system*, NEUROIMAGE, 9 (2), 195-207 (1999)). Here, the native space image can be run through FreeSurfer's recon-all pipeline, which performs automated segmentation of brain structures to reconstruct the white matter and pial surfaces. The FreeSurfer output surface is then converted to standard GIFTI format to produce each subject's native surface mesh. Finally, subjects' native surface meshes may be registered to the standard HCP surface mesh.

A sample from subcortical structure is mapped to a volumetric voxel, in contrast to a surface grayordinate. Subcortical samples in the AHBA are annotated by the structure from which they are taken (e.g., thalamus, or striatum). A sample can be mapped to a voxel in a similar procedure as for cortex, in which it is mapped to the voxel with minimum Euclidean distance for voxels labeled with that Freesurfer structure (e.g. thalamus, striatum) segmented in each subject's native space. This method involves computing a complete segmentation of all gray and white matter for each individual subject for whom gene expression data exists. Then these segmentations can be used to compute subcortical volume boundaries for each subject via automated tools such as FreeSurfer (Dale A M et al., *Cortical surface-based analysis I. Segmentation and surface reconstruction*, NEUROIMAGE, 9 (2), 179-194, 4931 (1999); Fischl B. et al, *Whole brain segmentation: Automated labeling of neuroanatomical structures in the human brain*, NEURON, 33

(3), 341-355, 3776 (2002) Fischl B. et al, *Cortical surface-based analysis. II: Inflation, flattening, and a surface-based coordinate system*, NEUROIMAGE, 9 (2), 195-207 (1999)). In turn, the subject-specific 'native space' locations of gene expression can be mapped onto that subject's subcortical volumes and transformed into a common atlas based on state-of-the-art registration methods (Anticevic A. et al., *Comparing surface-based and volume-based analyses of functional neuroimaging data in patients with schizophrenia*, NEUROIMAGE, 41(3):835-48, July 1 (2008); Glasser M F et al., *A multi-modal parcellation of human cerebral cortex*, NATURE, 536, 171-178 (11 Aug. 2016)).

As denoted in Box 430 (FIG. 4), samples are filtered for quality according to various criteria. For instance, samples whose measured expression level is not well above background, as provided in the AHBA dataset, can be excluded. Samples surviving this step (i) belonged to a probe whose mean signal is significantly different from the corresponding background, and (ii) had a background-subtracted signal which is at minimum 2.6 times greater than the standard deviation of the background. Furthermore, samples whose Euclidean distance to the nearest surface grayordinate is more than 2 standard deviations above the mean distance computed across all samples can be excluded.

As denoted in Box 440 (FIG. 4), imputation can be performed on samples which are missing values. For a given gene probe, not all AHBA samples contain values for that probe. These missing values can be estimated via multiple algorithmic approaches. For instance, missing values can be imputed via a Singular Value Decomposition (SVD) approach. This utilizes the property that although a sample is missing a value for some probes, it contains values for many other probes which are shared across samples. SVD-based imputation uses the similarity of samples, with respect to the shared probes, to estimate the expression value for a sample missing a probe. Other imputation approaches can include methods based on Principal Component Analysis (PCA), and spatial proximity.

As denoted in Box 450 (FIG. 4), various steps of data quality clean-up can be performed, such as to remove extraneous biases and improve signal-to-noise before combination with the neurobehavioral phenotype mapping data. These steps can improve the reproducibility of the maps, which can be quantified by a stability metric across subjects (differential stability). Example steps include: (1) expression values can be normalized within each subject (i.e., brain) before combining across subjects (e.g., via mean or median); (2) gene expression measurement sites can be filtered out on the basis of their exhibiting exceptionally low similarity with other measurement sites in their expression levels across genes; and (3) signal-to-noise of the spatial expression pattern can be improved through data processing techniques such as dimensionality reduction via principal component analysis (PCA).

For instance, expression levels for samples mapped onto the same surface vertex can be averaged. Using the raw AHBA dataset, however, can present additional challenges that can be addressed with further preprocessing. For instance, In some situations biases may be in the mean expression levels across AHBA samples, which should be corrected. Therefore, expression levels within each remaining sample can be de-meaned and normalized by z-scoring across all gene probes, to correct for variation across samples in the overall mean of data values, which may be driven by experimental artifacts.

As denoted in Box 460 (FIG. 4), generation brain-wide maps entails interpolation from the sparse samples to other brain regions which are not directly sampled, based on spatial proximity within a brain structure (e.g., cortex, or thalamus). These maps can be calculated at 'dense' or 'parcellated' levels.

Multiple methods can be used for interpolation. For instance, the method of 'Burt' to generate parcellated cortical maps is the following. Using cortical samples mapped onto subjects' native surface meshes, expression profiles for each of the 180 unilateral parcels in the HCP's MMP1.0 cortical parcellation can be computed in one of the two following ways. (i) For parcels that had at least one sample mapped directly onto one of their constituent surface vertices, parcellated expression values can be computed by averaging expression levels across all samples mapped directly onto the parcel. (ii) For parcels that had no samples mapped onto any of their constituent vertices, first a densely interpolated expression maps is created, in which each vertex in the native surface mesh is assigned the expression level associated with the most proximal surface vertex onto which a sample had been directly mapped, determined using surface-based geodesic distance along each subject's cortical surface mesh (i.e., a Voronoi diagram approach); the average of expression levels across parcels' constituent vertices is then computed to obtain parcellated expression values, effectively equivalent to performing a weighted average.

A dense cortical map could be generated directly from a Voronoi tessalation of the cortical surface. Other methods may be used, including weighted averaging based on exponential decay with increasing geodesic distance from the sample along the cortical surface (e.g. with characteristic length constant determined by the gene expression spatial autocorrelation structure).

Gene expression maps for subcortical structures can be computed at the parcellated or dense level. This follows a similar procedure as for cortex, described above, except that parcellations are defined as sets of 3-dimensional voxels, and distance is taken as Euclidean distance rather than geodesic distance along a surface.

The dense and parcellated maps include interpolation of gene expression values to all grayordinates in cortex. To perform this interpolation, multiple methods may be used. For example, a Voronoi diagram is constructed, assigning each grayordinate to its nearest AHBA sample location; that sample's gene expression values are then given to those grayordinate. Other methods may be used, including weighted averaging based on exponential decay with increasing geodesic distance from the sample along the cortical surface (e.g., with characteristic length constant determined by the gene expression spatial autocorrelation structure). This provides the dense map. To produce a parcellated map, the dense map may be parcellated with a CIFTI-defined parcellation using, for instance, the Connectome Workbench software or any other matrix manipulation software that can read the CIFTI format (e.g. Matlab, R statistical computing environment, Octave, Python, etc.). For example, the new cortical parcellation from the HCP team may be used. Glasser et al., *A multi-modal parcellation of human cerebral cortex*, NATURE 536:171-8 (2016) ("Glasser"). For parcels that contain gene expression, one method is to assign the parcel value as an average of the samples within that parcel, which can be a weighted average (e.g., based on the samples' relative Voronoi diagram coverages within the parcel).

As noted, additional coordinates can be assigned to measurement sites by explicitly computing the cortical and subcortical segmentation of each individual subject contributing to the AHBA based on their high-resolution structural post-mortem scans. In turn, such segmentations can be leveraged to compute a cortical mesh and subcortical anatomical nucleus assignment. In turn, the mesh forms a surface along with proximity that can then be calculated for each individual subject, yielding a set of subject-specific coordinates. In turn, such a cortical surface mesh can be aligned across subjects to the group atlas using surface-based features. This also applies to subcortical locations of expression, which can be defined at the subject level based on their anatomy and in turn aligned to a given group atlas. Following this spatial transformation, each subjects' individual coordinates are brought into alignment. Next, analyses can proceed at the specific location level, using specific coordinates for gene expression at that location. Neuroimaging maps can also capture the relevant cortical and subcortical locations.

Conversely, the continuous "dense" and discrete "parcellated" maps include assigning a gene expression value to a given cortical location either the native resolution of a given dense map or into a given discrete parcel/area. Example methods for this assignment include: (1) assignment of value to a given map location based its proximity to the locations at which gene expression is measured, i.e., the gene expression measurement sites. This can be done via, for example, nearest neighbor assignment; e.g., through construction of a Voronoi diagram; (2) assignment by a weighted sum to a map location based on the proximity to the locations at which gene expression is measured; e.g., weighted by distance along cortical surface from the gene expression measurement sites; and (3) assignment by a weighted sum across gene expression measurement sites which are within parcel boundaries according to a given parcellation.

Subcortical gene expression data can be used to assign values to subcortical locations or regions. Methods for this assignment include labeling by neuroanatomical evaluation, weighted sum within a parcellation of subcortical regions, or other forms of anatomical or functional location assignment.

Figure 5A:
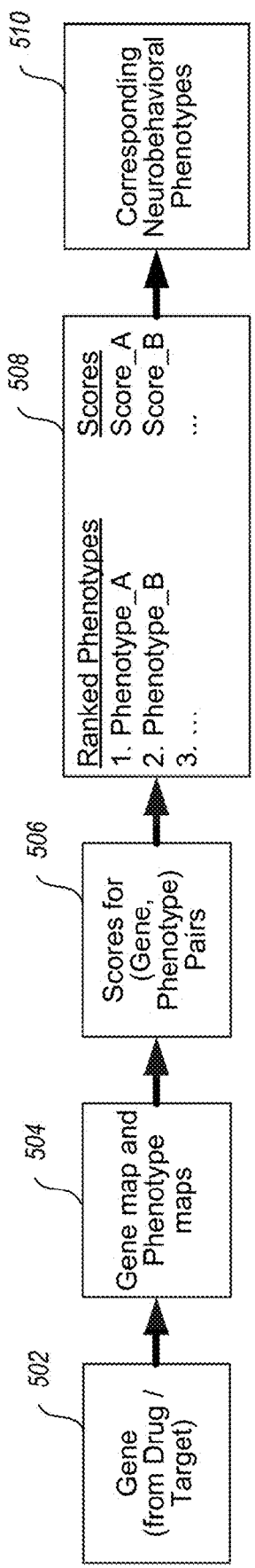
FIGS. 5A-5C illustrates the bi-directionality of innovation, showing gene to neuroimaging map and, conversely, neuroimaging map to drug target.
Figure 5B:
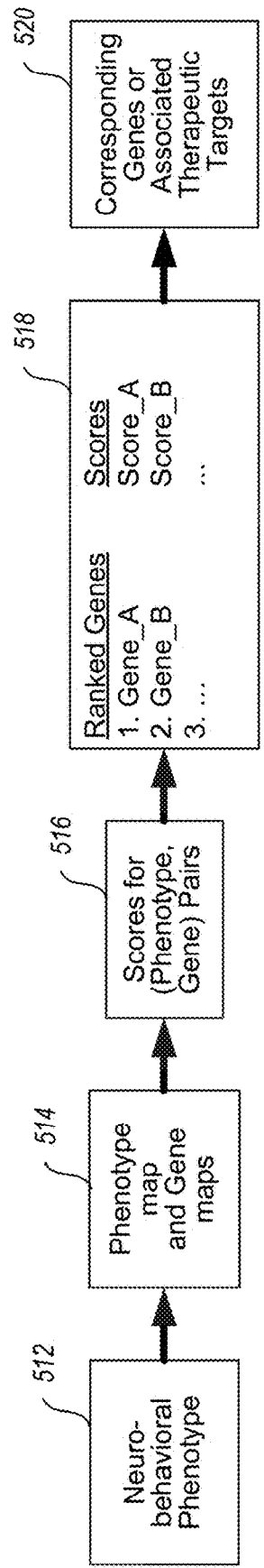
Figure 5C:
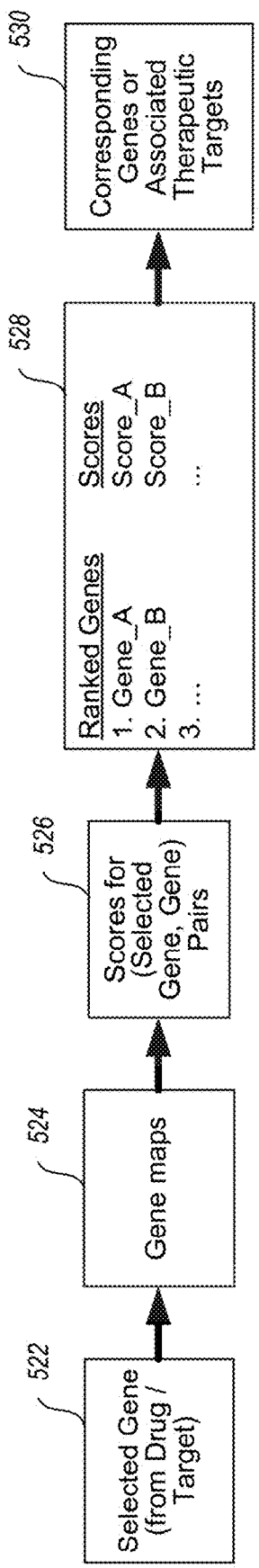

The present platform can function bidirectionally. In the gene (or drug target)-to-phenotype direction (FIG. 5A) or the phenotype-to-gene (or drug target) direction (FIG. 5B), or the gene-to-gene direction (FIG. 5C). With respect to FIG. 5A the platform can identify one or more neurobehavioral phenotypes whose characteristic brain maps (neurobehavioral phenotype mapping data) are aligned with the gene expression map for a given drug target of interest. This direction will be increasingly powerful with a larger database of neuroimaging maps linked with phenotypes. The goal is to go from a gene or drug target and identify a gene expression map, which in turn is used to identify one or more neurobehavioral phenotypes that statistically aligns with that gene expression map. This can in turn yield neurobehavioral phenotypes that are identified from gene or drug targets.

Specifically, a gene is identified (box 502), which may include selecting the gene based on an association with a selected drug or drug target. Gene expression mapping data for the identified gene and neurobehavioral phenotype mapping for one or more phenotypes are obtained (box 504). Scores are generated for each respective gene-phenotype pair by contacting and correlating the gene expression mapping data for the identified gene with the neurobehavioral phenotype mapping data for the respective phenotype of the respective pair (box 506). The gene-phenotype pairs are ranked based on their corresponding scores (box 508). And a highest score pair is identified for the selected gene (or drug or drug target) (box 510).

Conversely, in the phenotype-to-gene (or drug target) direction (FIG. 5B), the platform can identify genes or drug targets whose associated gene expression maps are contacted and aligned with the brain map (neurobehavioral phenotype mapping data) associated with a given neurobehavioral phenotype of interest. The goal is to go from a specific neurobehavioral phenotype and identify one or more gene expression maps that statistically aligns with that neurobehavioral phenotype, which in turn is used to identify which drug target aligns with those identified gene expression maps. This can in turn yield drug targets that are identified from neurobehavioral phenotypes.

Specifically, a neurobehavioral phenotype is selected (box 512). Neurobehavioral phenotype mapping for the selected phenotype and gene expression mapping data for one or more genes are obtained (box 514). Scores are generated for each respective phenotype-gene pair by contacting and correlating the neurobehavioral mapping data for the selected neurobehavioral phenotype with the gene expression mapping data for the respective gene of the respective pair (box 516). The phenotype-gene pairs are ranked based on their corresponding scores (box 518). And genes (or drug target) associated with a highest score pair is identified for the selected neurobehavioral phenotype (box 520).

In some embodiments, in the gene-to-gene direction (FIG. 5C), the platform can identify genes or drug targets whose associated gene expression maps are contacted and aligned with the gene expression maps of other genes or drug targets. The goal is to go from a specific gene and identify one or more gene expression maps for other genes that statistically aligns with that specific gene, which in turn is used to identify which drug target aligns with those identified gene expression maps. This can in turn yield drug targets that are identified from other genes.

Specifically, a gene is selected (box 522). Gene expression mapping for the selected gene and gene expression mapping data for one or more other genes are obtained (box 524). Scores are generated for each respective gene-gene pair by contacting and correlating the gene expression mapping data for the selected gene with the gene expression mapping data for the respective other gene of the respective pair (box 526). The gene-gene pairs are ranked based on their corresponding scores (box 528). And genes (or drug target) associated with a highest score pair is identified for the selected gene (box 530).

In some embodiments, previously generated phenotype-gene pair topographies may be utilized to identify a gene or drug target from a plurality of genes or drug targets for a specific individual. For example, an individual subject's neuroimaging may be obtained and the neurophenotype topography generated. This neurophenotype topography is then compared to a plurality of previously generated phenotype-gene pair topographies (when generated as described herein). A target phenotype-gene pair topography that most closely aligns with the individual's neurobehavioral phenotype topography is then selected. The corresponding genotype topography that was used to generate the target phenotype-gene pair topography is identified and its corresponding gene selected. From this gene selection, a drug target associated with the selected gene is then selected as a specific drug target for that individual.

In other embodiments, previously generated gene-phenotype pair topographies may be utilized to identify individuals for a specific drug or drug target. For example, genotype topography for a gene associated with a selected drug target may be generated. This genotype topography is then compared to a plurality of previously generated gene-phenotype pair topographies (when generated as described herein). A target gene-phenotype pair topography that most closely aligns with the genotype topography is then selected. Neurobehavioral phenotype mapping data of individuals is then compared to the target gene-phenotype pair topography, and those individuals whose neurobehavioral phenotype mapping data aligns with the target gene-phenotype pair topography (within a threshold level) are selected as being candidates that can benefit from the selected drug target.

In this way individual subject's neuroimaging and/or gene expression data can be contacted/aligned with a previously generated topography pair for detecting, diagnosing, predicting, prognosticating, or treating a neurobehavioral phenotype in a subject.

Implementation of embodiments described herein may be performed by one or more computing devices or systems. One or more special-purpose computing systems may be used to implement such embodiments described herein. Accordingly, various embodiments described herein may be implemented in software, hardware, firmware, or in some combination thereof. Such a computing system includes memory or other computer-readable media, one or more processors, a display device, a network interface, other input/output (I/O) interfaces, and other components.

The one or more processors include processing device(s) that execute computer instructions to perform actions, including at least some embodiments described herein. In various embodiments, the processor may include one or more central processing units (CPUs), programmable logic, or other processing circuitry.

The memory may include one or more various types of non-volatile and/or volatile storage technologies. Examples of such memory include, but are not limited to, flash memory, hard disk drives, optical drives, solid-state drives, various types of random access memory (RAM), various types of read-only memory (ROM), other computer-readable storage media (also referred to as processor-readable storage media), or other memory technologies, or any combination thereof. The memory may be utilized to store information, including computer-readable instructions that are utilized by the one or more processors to perform actions, including at least some embodiments described herein. The memory may also store other programs and other content, such as operating systems, user applications, other computer programs, the neurobehavioral phenotype mapping data, the gene expression mapping data, the generated neurophenotype topographies and scores/rankings, or other data. The computing system may include other computer-readable media that may include other types of stationary or removable computer-readable media, such as removable flash drives, external hard drives, or the like.

The display device is any display device capable of rendering content to a user, such as the neurophenotype topographies, scores, drug target or neurobehavioral phenotype selections, etc. Examples of such a display device may include a liquid crystal display, light emitting diode, or other type of display device, and may include a touch sensitive screen capable of receiving inputs from a user's hand, stylus, or other object.

The network interfaces are configured to communicate with other computing devices, via a wired or wireless communication network. Such network interfaces include transmitters and receivers to send and receive data, such as, but not limited to, gene expression mapping data or neurobehavioral phenotype mapping data. The other I/O interfaces may include interfaces for various other input or output devices, such as audio interfaces, other video interfaces, USB interfaces, physical buttons, keyboards, or the like.

In some embodiments, the present platform includes a computing device, comprising: a memory that stores computer instructions; a processor that, when executing the computer instructions, performs actions to: generate a neurophenotype topography for a selected neurobehavioral phenotype based on neurobehavioral phenotype mapping data for the selected neurobehavioral phenotype; generate a genotype topography for each respective gene of a plurality of genes based on gene expression mapping data for the respective gene; define a plurality of phenotype-gene pair topographies between the selected neurobehavioral phenotype and the plurality of genes, each phenotype-gene pair topography for each respective phenotype-gene pair being defined based on the neurophenotype topography of the selected neurobehavioral phenotype and the genotype topography of the respective gene for the respective phenotype-gene pair; determine a quantitative score for each of the plurality of phenotype-gene pair topographies based on a correlation between the neurophenotype topography of the selected neurobehavioral phenotype and the genotype topography of the respective gene for the respective phenotype-gene pair; select one or more of the plurality of phenotype-gene pair topographies having a respective score above a selected threshold; and display the respective genes of the selected one or more phenotype-gene pair topographies to a user. In an embodiment, the processor, when executing the computer instructions, further performs actions to identify one or more respective neural drug targets associated with the respective genes of the selected one or more phenotype-gene pair topographies. In an embodiment, the processor generates the neurophenotype topography by executing further computer instructions to generate the neurophenotype topography from the neurobehavioral phenotype mapping data for each of a plurality of people having the selected neurobehavioral phenotype. In an embodiment, the processor determines the score for each of the plurality of phenotype-gene pair topographies by executing further computer instructions to determine a statistical significance for each phenotype-gene pair topography based on an alignment between the gene expression mapping data for the respective gene with the neurobehavioral phenotype mapping data. In an embodiment, the processor selects the one or more phenotype-gene pair topographies by executing further computer instructions to select a target phenotype-gene pair topography having a highest determined measure of association between the neurophenotype topography of the selected neurobehavioral phenotype and the genotype topography of the respective gene for the target phenotype-gene pair topography. In an embodiment, the gene expression mapping data for each of the plurality of genes includes gene expression mapping data for a plurality of gene expressions from a plurality of people without the selected neurobehavioral phenotype. In an embodiment, the processor generates the genotype topography for each respective gene by executing further computer instructions to select a representative probe for each of the plurality of genes across the plurality of gene expressions for the plurality of people. In an embodiment, the processor generates the genotype topography for each respective gene by executing further computer instructions to map gene expression mapping samples to locations in brain structures. In an embodiment, the processor generates the genotype topography for each respective gene by executing further computer instructions to filter gene expression mapping samples by excluding samples with measured expression levels below a threshold level above background signals. In an embodiment, the processor generates the genotype topography for each respective gene by executing further computer instructions to impute probe values in gene expression mapping samples that are missing probe values. In an embodiment, the processor generates the genotype topography for each respective gene by executing further computer instructions to remove extraneous biases from the gene expression mapping data. In an embodiment, the processor removes the extraneous biases by executing further computer instructions to de-mean and normalize z-scores across gene probes used to capture the gene expression mapping data. In an embodiment, the processor generates the genotype topography for each respective gene by executing further computer instructions to increase a signal-to-noise ratio in the gene expression mapping data. In an embodiment, the processor increases the signal-to-noise ratio by executing further computer instructions to average expression levels of the gene expression mapping data for samples mapped onto a same surface vertex. In an embodiment, the processor generates the genotype topography for each respective gene by executing further computer instructions to interpolate sparse gene expression samples from sampled brain regions to other non-sampled brain regions. In an embodiment, the processor interpolates the sparse gene expression samples by executing further computer instructions to generate at least one of parcellated cortical or subcortical maps or a dense cortical or subcortical map. In an embodiment, the processor generates the genotype topography for each respective gene by executing further computer instructions to assign a weight value for each of a plurality of brain regions in the gene expression mapping data. In an embodiment, the processor generates the neurobehavioral topography by executing further computer instructions to assign a weight value for each of a plurality of brain regions in the neurobehavioral phenotype mapping data. In an embodiment, the processor assigns the weight value for each of the plurality of brain regions by executing further computer instructions to: assign a first set of weight values above a threshold value for a first set of brain regions of the plurality of brain regions in the neurobehavioral phenotype mapping data; and assign a second set of weight values below the threshold value for a second set of brain regions of the plurality of brain regions in the neurobehavioral phenotype mapping data. In an embodiment, the processor assigns the weight value for each of the plurality of brain regions by executing further computer instructions to assign a masking weight value to a target brain region of the plurality of brain regions to remove information associated with the target brain region from the neurobehavioral phenotype mapping data. In an embodiment, the processor defines the plurality of phenotype-gene pair topographies by executing further computer instructions to define at least one combination phenotype-gene pair topography between the neurobehavioral phenotype topography and a combination of genotype topographies for a combination of genes. In an embodiment, the processor, when executing the computer instructions, further performs actions to: select the at least one combination phenotype-gene pair topography as the one or more of the plurality of phenotype-gene pair topographies having the respective score above the selected threshold; and display the combination of genes to the user. In an embodiment, the processor, when executing the computer instructions, further performs actions to: identify combinations of genes or neural drug targets by combining gene expression mapping data that exhibits improved alignment with the neurobehavioral phenotype mapping data relative to the alignment of gene expression mapping data and neurobehavioral phenotype mapping data for each separate gene or neural drug target. In an embodiment, the neurobehavioral phenotype mapping data is for one of a brain disorder, a symptom, or a cognitive process.

In some embodiments, the present platform includes a method, comprising: obtaining, by a computing device, neuro phenotype mapping data for a selected neurophenotype; obtaining, by the computing device, gene expression mapping data for one or more genes; determining, by the computing device, a quantitative score for each respective phenotype-gene pair between the selected neurobehavioral phenotype and a respective gene of the one or more genes based on a correlation between the neurobehavioral phenotype mapping data for the selected neurobehavioral phenotype and the gene expression mapping data for the respective gene of the respective phonotype-gene pair; and presenting, by the computing device, the determined score for each phenotype-gene pair to a user.

In some embodiments, the present platform includes a computing device, comprising: a memory that stores computer instructions; a processor that, when executing the computer instructions, performs actions to: generate, by the computing device, a genotype topography for a selected gene based on gene expression mapping data for the selected gene; generate, by a computing device, a neurophenotype topography for each respective neurobehavioral phenotype of a plurality of neurobehavioral phenotypes based on neurobehavioral phenotype mapping data for the respective neurobehavioral phenotype; define, by the computing device, a plurality of gene-phenotype pair topographies between the selected gene and the plurality of neurobehavioral phenotypes, each gene-phenotype pair topography for each respective gene-phenotype pair being defined based on the genotype topography of the selected gene and the neurophenotype topography of the respective neurobehavioral phenotype for the respective gene-phenotype pair; determine, by the computing device, a quantitative score for each of the plurality of gene-phenotype pair topographies based on a correlation between the genotype topography of the selected gene and the neurophenotype topography of the respective neurobehavioral phenotype for the respective gene-phenotype pair; select one or more of the plurality of gene-phenotype pair topographies having a respective score above a selected threshold; and display the respective neurobehavioral phenotypes of the selected one or more gene-phenotype pair topographies to a user. In an embodiment, the processor, when executing the computer instructions, further performs actions to select the selected gene based on a user selected neural drug target associated with the selected gene. In an embodiment, the processor generates the neurophenotype topography by executing further computer instructions to generate the neurophenotype topography from the neurobehavioral phenotype mapping data for each of a plurality of people having the selected neurobehavioral phenotype. In an embodiment, the processor determines the score for each of the plurality of gene-phenotype pair topographies by executing further computer instructions to determine a statistical significance for each gene-phenotype pair topography based on an alignment between the neurobehavioral phenotype mapping data for the respective neurobehavioral phenotype with the gene expression mapping data. In an embodiment, the processor selects the one or more gene-phenotype pair topographies by executing further computer instructions to select a target gene-phenotype pair topography having a highest determined measure of association between the genotype topography of the selected gene and the neurophenotype topography of the respective neurobehavioral phenotype for the target gene-phenotype pair topography. In an embodiment, the gene expression mapping data for the selected gene includes gene expression mapping data for a plurality of gene expressions from a plurality of people without one of the plurality of neurobehavioral phenotypes. In an embodiment, the processor generates the genotype topography for the selected gene by executing further computer instructions to select a representative probe for the selected gene across the plurality of gene expressions for the plurality of people. In an embodiment, the processor generates the genotype topography for the selected gene by executing further computer instructions to map gene expression mapping samples to locations in brain structures. In an embodiment, the processor generates the genotype topography for the selected gene by executing further computer instructions to filter gene expression mapping samples by excluding samples with measured expression levels below a threshold level above background signals. In an embodiment, the processor generates the genotype topography for the selected gene by executing further computer instructions to impute probe values in gene expression mapping samples that are missing probe values. In an embodiment, the processor generates the genotype topography for the selected gene by executing further computer instructions to remove extraneous biases from the gene expression mapping data. In an embodiment, the processor removes the extraneous biases by executing further computer instructions to de-mean and normalize z-scores across gene probes used to capture the gene expression mapping data. In an embodiment, the processor generates the genotype topography for the selected gene by executing further computer instructions to increase a signal-to-noise ratio in the gene expression mapping data. In an embodiment, the processor increases the signal-to-noise ratio by executing further computer instructions to average expression levels of the gene expression mapping data for samples mapped onto a same surface vertex. In an embodiment, the processor generates the genotype topography for the selected gene by executing further computer instructions to interpolate sparse gene expression samples from sampled brain regions to other non-sampled brain regions. In an embodiment, the processor interpolates the sparse gene expression samples by executing further computer instructions to generate at least one of parcellated cortical or subcortical maps or a dense cortical or subcortical map. In an embodiment, the processor generates the genotype topography for the selected gene by executing further computer instructions to assign a weight value for each of a plurality of brain regions in the gene expression mapping data. In an embodiment, the processor generates the neurobehavioral topography for each respective neurobehavioral phenotype by executing further computer instructions to assign a weight value for each of a plurality of brain regions in the neurobehavioral phenotype mapping data. In an embodiment, the processor assigns the weight value for each of the plurality of brain regions by executing further computer instructions to: assign a first set of weight values above a threshold value for a first set of brain regions of the plurality of brain regions in the neurobehavioral phenotype mapping data; and assign a second set of weight values below the threshold value for a second set of brain regions of the plurality of brain regions in the neurobehavioral phenotype mapping data. In an embodiment, the processor assigns the weight value for each of the plurality of brain regions by executing further computer instructions to assign a masking weight value to a target brain region of the plurality of brain regions to remove information associated with the target brain region from the neurobehavioral phenotype mapping data. In an embodiment, the processor defines the plurality of gene-phenotype pair topographies by executing further computer instructions to define at least one combination gene-phenotype pair topography between the genotype topography and a combination of neurophenotype topographies for a combination of neurobehavioral phenotypes. In an embodiment, the processor, when executing the computer instructions, further performs actions to: select the at least one combination gene-phenotype pair topography as the one or more of the plurality of gene-phenotype pair topographies having the respective score above the selected threshold; and display the combination of neurobehavioral phenotype to the user. In an embodiment, the processor, when executing the computer instructions, further performs actions to: identify combinations of neurobehavioral phenotypes by combining neurophenotype mapping data that exhibits improved alignment with the gene expression mapping data relative to the alignment of neurophenotype mapping data and gene expression mapping data for each separate neurobehavioral phenotype. In an embodiment, the neurobehavioral phenotype mapping data is for one of a brain disorder, a symptom, or a cognitive process.

In some embodiments, the present platform includes a method, comprising: obtaining, by the computing device, gene expression mapping data for one or more genes; obtaining, by a computing device, neurophenotype mapping data for a selected neurophenotype; determining, by the computing device, a quantitative score for each respective gene-phenotype pair between the selected gene and a respective neurophenotype of the one or more neurobehavioral phenotypes based on a correlation between the gene expression mapping data for the selected gene and the neurophenotype mapping data for the respective neurobehavioral phenotype of the respective gene-phonotype pair; and presenting, by the computing device, the determined score for each gene-phenotype pair to a user.

In some embodiments, the present platform includes a computing device, comprising: a memory that stores computer instructions; a processor that, when executing the computer instructions, performs actions to: generate a plurality of genotype topographies for a plurality of genes based on respective gene expression mapping data for each respective gene; select a first genotype typography from the plurality of genotype topographies for a first gene from the plurality of genes; select a plurality of second genotype topographies from the plurality of genotype topographies for a plurality of second genes from the plurality of genes; define a plurality of gene-gene pair topographies between the first gene and the plurality of second genes, each gene-gene pair topography for each respective gene-gene pair being defined based on the first genotype topography of the selected gene and a respective second genotype topography of the respective second gene for the respective gene-gene pair; determine a quantitative score for each of the plurality of gene-gene pair topographies based on a correlation between the first genotype topography of the first gene and the second genotype topography of the respective second gene for the respective gene-gene pair; select one or more of the plurality of gene-gene pair topographies having a respective score above a selected threshold; and display the respective second genes of the selected one or more gene-gene pair topographies to a user. In an embodiment, the processor, when executing the computer instructions, further performs actions to select the first gene based on a user selected neural drug target associated with the first gene. In an embodiment, the processor, when executing the computer instructions, further performs actions to identify one or more respective neural drug targets associated with the respective second genes of the selected one or more gene-gene pair topographies. In an embodiment, the processor determines the score for each of the plurality of gene-gene pair topographies by executing further computer instructions to determine a statistical significance for each gene-gene pair topography based on an alignment between the respective gene expression mapping data for the respective second gene with the respective gene expression mapping data for the first gene. In an embodiment, the processor selects the one or more gene-gene pair topographies by executing further computer instructions to select a target gene-gene pair topography having a highest determined measure of association between the first genotype topography of the first gene and the respective second genotype topography of the respective second gene for the target gene-gene pair topography. In an embodiment, the gene expression mapping data includes gene expression mapping data for a plurality of gene expressions from a plurality of people. In an embodiment, the processor generates the plurality of genotype topographies by executing further computer instructions to select a representative probe for a respective gene across the plurality of gene expressions for the plurality of people. In an embodiment, the processor generates the plurality of genotype topographies by executing further computer instructions to map gene expression mapping samples to locations in brain structures. In an embodiment, the processor generates the plurality of genotype topographies by executing further computer instructions to filter gene expression mapping samples by excluding samples with measured expression levels below a threshold level above background signals. In an embodiment, the processor generates the plurality of genotype topographies by executing further computer instructions to impute probe values in gene expression mapping samples that are missing probe values. In an embodiment, processor generates the plurality of genotype topographies by executing further computer instructions to remove extraneous biases from the gene expression mapping data. In an embodiment, the processor removes the extraneous biases by executing further computer instructions to de-mean and normalize z-scores across gene probes used to capture the gene expression mapping data. In an embodiment, the processor generates the plurality of genotype topographies by executing further computer instructions to increase a signal-to-noise ratio in the gene expression mapping data. In an embodiment, the processor increases the signal-to-noise ratio by executing further computer instructions to average expression levels of the gene expression mapping data for samples mapped onto a same surface vertex. In an embodiment, the processor generates the plurality of genotype topographies by executing further computer instructions to interpolate sparse gene expression samples from sampled brain regions to other non-sampled brain regions. In an embodiment, the processor interpolates the sparse gene expression samples by executing further computer instructions to generate at least one of parcellated cortical or subcortical maps or a dense cortical or subcortical map. In an embodiment, the processor generates the plurality of genotype topographies by executing further computer instructions to assign a weight value for each of a plurality of brain regions in the gene expression mapping data. In an embodiment, the processor assigns the weight value for each of the plurality of brain regions by executing further computer instructions to: assign a first set of weight values above a threshold value for a first set of brain regions of the plurality of brain regions in the gene expression mapping data; and assign a second set of weight values below the threshold value for a second set of brain regions of the plurality of brain regions in the gene expression mapping data. In an embodiment, the processor assigns the weight values for each of the plurality of brain regions by executing further computer instructions to assign a masking weight value to a target brain region of the plurality of brain regions to remove information associated with the target brain region from the gene expression mapping data. In an embodiment, the processor defines the plurality of gene-gene pair topographies by executing further computer instructions to define at least one combination gene-gene pair topography between the first genotype topography and a combination of second genotype topographies for a combination of second genes. In an embodiment, the processor, when executing the computer instructions, further performs actions to: select the at least one combination gene-gene pair topography as the one or more of the plurality of gene-gene pair topographies having the respective score above the selected threshold; and display the combination of second genes to the user.

In some embodiments, the present platform includes a method, comprising: obtaining, by the computing device, gene expression mapping data for a plurality of genes; determining, by the computing device, a quantitative score for each respective gene-gene pair between a selected gene and one or more other genes based on a correlation between the gene expression mapping data for the selected gene and the gene expression mapping data for the one or more other genes of the respective gene-gene pair; and presenting, by the computing device, the determined score for each gene-gene pair to a user.

In some embodiments, the present platform includes a method for identifying a neural drug target comprising: selecting a neurobehavioral phenotype; processing gene expression mapping data and neurobehavioral phenotype mapping data; defining a relevant neurophenotype topography; and predicting the likelihood of association between gene expression for the neural drug target and the neurobehavioral phenotype, wherein at least one method step is performed using one of a computer-implemented method or a computer-readable medium. In an embodiment, this method further comprises pre-processing the neurobehavioral phenotype mapping data. In an embodiment, this method further comprises one of weighting or masking the neurobehavioral phenotype mapping data. In an embodiment, this method further comprises at least one of removing extraneous biases from the gene expression mapping data or improving gene expression mapping data signal-to-noise ratio. In an embodiment, this method includes a step of defining the relevant neurophenotype topography that includes pre-processing the gene expression mapping data associated with at least one brain location or region. In an embodiment, this method includes gene expression mapping data that occurs at one of a sparse sample level, an interpolated dense map level, or a discrete parcellated brain map level. In an embodiment, this method further comprises assigning one or more gene expression values to continuous dense locations in cortex or to discrete locations in cortex. In an embodiment, this method includes neurobehavioral phenotype mapping data that is for one of a brain disorder, a symptom, or a cognitive process. In an embodiment, this method further comprises predicting the likelihood of a neural drug target therapy to affect off-target brain regions. In an embodiment, this method further comprises identifying combinations of neural drug targets by combining gene expression mapping data, wherein said combined gene expression mapping data exhibits improved alignment with the neurobehavioral phenotype mapping data relative to the alignment of gene expression mapping data and neurobehavioral phenotype mapping data for each separate neural drug target.

In some embodiments, the present platform includes a method for identifying neurobehavioral phenotypes comprising: aligning pre-processed gene expression mapping data with neurobehavioral phenotype mapping data; and defining a relevant neural neurophenotype topography. In an embodiment, this method further comprises pre-processing the gene expression mapping data. In an embodiment, this method further comprises one of weighting or masking the gene expression mapping data. In an embodiment, this method further comprises pre-processing the gene expression mapping data either to remove extraneous biases or to improve signal-to-noise ratio. In an embodiment, this method includes a step of defining the relevant neurophenotype topography that includes pre-processing the gene expression mapping data associated with at least one brain location or region. In an embodiment, this method includes gene expression mapping data that occurs at one of a sparse sample level, an interpolated dense map level, or a discrete parcellated brain map level. In an embodiment, this method further comprises assigning one or more gene expression values to continuous dense locations in cortex or to discrete locations in cortex. In an embodiment, this method includes neurobehavioral phenotype mapping data that is for one of a brain disorder, a symptom, or a cognitive process. In an embodiment, this method further comprises predicting the likelihood of a neural drug target therapy to affect off-target brain regions.

In some embodiments, the present platform includes a non-transitory computer-readable medium having instructions stored thereon that, upon execution by a computing device, cause the computing device to perform operations for identifying a therapeutic target comprising: quantifying alignment of gene expression mapping data with neurobehavioral phenotype mapping data and defining a relevant neural neurophenotype topography.

In some embodiments, the present platform includes a non-transitory computer-readable medium having instructions stored thereon that, upon execution by a computing device, cause the computing device to perform operations for identification of a neurobehavioral phenotype comprising: quantifying alignment of gene expression mapping data with neurobehavioral phenotype mapping data and defining a relevant neural neurophenotype topography.

In some embodiments, the present platform includes a computer-implemented system for analyzing alignment of gene expression mapping data with neurobehavioral phenotype mapping data, comprising: a memory; and one or more processors coupled to the memory, wherein the one or more processors are configured to quantify alignment of gene expression mapping data with neurobehavioral phenotype mapping data.

Methods of Use

Individualized treatment selection. A common problem when making treatment choices for central nervous system (CNS) disorders and neuropsychiatric disorders is optimally tailoring treatment for a given individual. At present this problem remains unaddressed and the way the medical field makes these decisions is at the group level based on group categorical assignment made via clinician behavioral observation and/or patients' self-report.

The present tools and methods provide for optimization of a putative treatment response at the individual patient level. Specifically, one can take a neurobehavioral phenotype for a given patient, which can be measured either neurally or behaviorally. That is, the neurophenotype information can be derived from the neurophenotype map directly or by leveraging a set of behavioral scores that are associated with a neurophenotype map sensitive to variation in this neurobehavioral phenotype. Once the neurobehavioral phenotype map is derived then one would compute the maximal alignment with a gene expression map, or genotype topography, to determine a suitable neurophenotype topography. In one scenario, for example, five (5) drugs that target somewhat distinct mechanisms but are all indicated for a range of neuropsychiatric diagnoses may be examined relative to a neurophenotype topography. Thus, this method would allow a quantitative ranked ordering of the five (5) drugs based on the relative similarity or linkage between gene expression and the neuro-phenotype map for a specific patient as determined using this genotype and neurophenotype topography approach. This method may be used to prioritize treatment decisions for a patient.

The present tools and methods also provide for identification of drug targets based on similarity to a gene implicated. At present if a molecule is implicated in a given disease but that target is not directly drugable then a way is needed to pharmacologically target the neural circuits involved in the disease. To achieve this, alternative drugs are needed that can be screened based on their similarity to the implicated target which is not drugable. The present approach enables this by starting with a gene implicated in a given disease. Because such a gene and its associated proteins may be difficult to modulate directly via pharmacological treatments, an alternative strategy is needed whereby one can modulate another drug target whose brain-wide gene expression pattern is aligned with that of a disrupted target. The present tools and methods can identify such genes by computing similarity scores for genes that show expression topographies highly similar to disrupted genes and therefore would exhibit high gene-gene map similarity scores. This gene-to-gene alignment suggests that drugs which target the receptor proteins associated with the derived genes are well-distributed to preferentially modulate the same regions that strongly express the disrupted mechanism that may not be directly modulated.

The present tools and methods also provide for identification of drug targets based on a gene similarity to a neural circuit implicated. A major knowledge gap in treating neuropsychiatric conditions is the ability to identify drug targets for a specific neural alteration. Put differently, if one is able to identify a neural circuit alteration that is associated with a neuropsychiatric symptom then the challenge is mapping that neural circuit to a drug target. Here the present tools and methods provide a method for quantifying the obtained neurobehavioral map in relation to a gene expression profile. As noted, the neurobehavioral phenotype information can be derived from the neurobehavioral phenotype map directly or by leveraging a set of behavioral scores that are associated with a neurobehavioral phenotype map sensitive to group variation in this behavior. Once the group neurobehavioral phenotype map is derived, one would compute or compare the maximal alignment of the neurobehavioral phenotype map with gene expression maps. This would yield a quantitative score for the genes that are maximally aligned with the disrupted circuit, which in turn would allow development of molecules for such circuits.

The present tools and methods also provide for selection of a suitable patent population subset, or purification of patient population, to test efficacy of application (i.e. clinical trial optimization), either via brain or behavior. For example, this means that one could select patients based on their brain map, which the tool has previously mapped to a behavior or symptom profile or could select patients using responses to a question or performance of a behavioral task which the tool has mapped previously to a brain map.

A key challenge in therapeutic development is identification of the optimal cohort of patients for which the new treatment may be optimal. At present, these decisions are made based on broad indication at the categorical level (e.g. depression versus psychosis). Ultimately, this broad approach does not allow for a quantitatively-driven selection or purification of the patient population that may be best aligned with a given drug that is used to investigate clinical efficacy. The present tools and methods provides a quantitative method for deriving a gene expression map for a given molecular target (i.e. gene map). In turn, the present tools and methods would screen patients based on a neurobehavioral phenotype mapping that produces maximal alignment with the given gene expression map. In doing so, the present tools and methods provide guidance or direction for the inclusion or exclusion of patients in a given study or trial based on alignment of their neurobehavioral phenotype mapping or profiles and the gene expression mapping of interest.

The present tools and methods also provide for selection of putative molecules for a human clinical trial. A major challenge in design of new molecules for a given human clinical population involves the selection of molecular targets that may be relevant for such a population based on the pattern of disrupted brain-behavior relationships. The present approach provides a method to inform putative target engagement based on alignment to a neurobehavioral phenotype map of interest with a given gene expression map. In doing so, the present tools and methods may directly inform a choice of which existing molecule to use in a clinical trial by selecting the molecule that exhibits the maximal alignment with the clinical neurobehavioral phenotype of interest.

The present tools and methods also provide for preclinical or animal applications of neurobehavioral phenotype mapping and transcriptome or gene expression mapping for drug molecule selection. A fundamental challenge for design of new molecules involves selection of the right molecules for a given neural target. The present approach provides a method to produce a high-throughput screen via a disease animal model (e.g. knockout). Specifically, if one obtains a neurobehavioral phenotype map in the animal (e.g. via animal neuroimaging), then this approach provides a method to quantitatively screen across genes that maximally align with such a neurobehavioral phenotype map. This method allows application of the present tools and methods to therapeutic design by screening for potential molecular targets.

The present tools and methods also provide for diagnostic decisions for specific people based on implicated neural circuits. A major need in the field of neuropsychiatry is the ability to derive diagnostically relevant decisions based on implicated neural circuits. At present, the field fundamentally lacks a framework to achieve this goal. The present tools and methods provide a method for quantifying the level of alignment between an existing neurobehavioral phenotype for a given person and a given gene expression profile. To the extent that the two maps deviate from each other (i.e. reflect a dis-similarity), this information also can be used to reach a diagnostic decision for a given individual.

The present tools and methods also provide for diagnostic decisions for specific people based on behavioral variation for which there are quantitative links to relevant neurobehavioral phenotypes. A related major need in the field of neuropsychiatry is the ability to inform diagnostically relevant variation in a neural circuit that is linked to an altered neurobehavioral phenotype profile (e.g. psychosis). At present there is no method to quantify if such a neural circuit is exhibiting variation that is similar or dissimilar from a normative gene expression profile. The present tools and methods provide a method for establishing a genotype and neurophenotype topography by quantifying the level of alignment between a neurobehavioral phenotype for a given person and a given gene expression profile. To the extent that the two maps deviate from each other (i.e. reflect a dis-similarity), this information also can be used to reach a diagnostic decision for a given individual.

The present tools and methods also provide for prognosticating the effect of an administered therapy based on gene transcriptome or gene expression mapping alignment. A critical goal in treatment decisions for neuropsychiatric disorders involves the ability to make clinically meaningful predictions over time. One method of use available using the present tools and methods would be to quantify the level of similarity between a neurobehavioral phenotype for a given person and a given gene expression mapping profile for that same person over time, for instance before and after treatment. Specifically, the present tools and methods would provide a genotype and neurophenotype topography quantitative score reflecting whether the neurobehavioral phenotype is, or is not, more closely aligned with the gene expression map after treatment.

The present tools and methods also provide for prognosticating the putative treatment response prior to full blown illness (i.e. risk) for neural circuit alteration based on gene transcriptome alignment with a neurobehavioral phenotype. Another key goal in treatment decisions for neuropsychiatric disorders involves the ability to make clinically meaningful predictions prior to the onset of full-blow illness. In other words, often times it is vital to identify people 'at risk' for severe neuropsychiatric illness prior to the onset of the full range of neurobehavioral phenotype symptoms. One method of use of the present tools and methods would be to quantify the level of similarity between a neurobehavioral phenotype for a given person and a given gene expression profile or gene expression mapping in individuals at elevated genetic or clinical risk for a given neuropsychiatric condition. In this context, a "gene expression profile" may refer to a next-level analysis of the gene expression within canonical functional networks (i.e. specific collections of brain regions that we know are involved in a specific function); whereas "gene expression mapping" may refer to expression pattern across all brain regions sampled. For instance, a specific actionable method of use would be to derive neurobehavioral phenotype mapping for individuals at risk for psychosis and then quantify the level of neurobehavioral phenotype mapping similarity to a gene expression profile or gene expression mapping that would reflect variation in the neurobehavioral phenotype mapping of interest. Specifically, the present tools and methods would provide a quantitative score reflecting the level of 'risk' for psychosis conversion based on the quantitative similarity to or deviation from a given gene expression map.

The present tools and methods also provide for practical application of bypassing invasive pharmacoimaging. A frequent bottleneck in rational drug design in human clinical trials is the verification of target engagement, typically via invasive pharmaconeuroimaging (e.g. fMRI or PET). In this context specifically, this approach can provide a way to identify a neurobehavioral phenotype if there is a known clinical pharmacological response in a group of individuals with known symptom response. Here, if there is no prior evidence for target engagement based on the drug of interest, then the present tools and methods provide a method of use that would pinpoint a given neural circuit that is responsive to the drug molecule by alignment of such a neural circuit with a gene transcriptome or gene expression map for that drug to establish a relevant genotype and neurophenotype topography. Put differently, the present tools and methods can derive a neurophenotype topography for a given molecule based on the transcriptome pattern or gene expression mapping of that the gene involved in a given mechanism, pharmacological response. In turn, this neurophenotype topography can be used to select neural circuits that would be maximally aligned with the mechanism of interest, effectively bypassing the need for target engagement pharmacoimaging.

The present tools and methods also provide for optimization of polypharmacy. It is often the case that many patients respond best to more than a single drug. The process of 'fine tuning' the selection of such a polypharmacy treatment regimen is at present not driven by quantitative or neurobiologically principled methods but rather a clinician's qualitative assessment of the patient or the patient's self-report. Consequently, this process of polypharmacy administration is often difficult to precisely optimize. Furthermore, prior to initiating any treatment it is at present impossible to arrive at a quantitatively-grounded choice for which combination of drugs may be efficacious for a given person, symptom or set of symptoms. Therefore, the present tools and methods provide for a method of use to select and optimize polypharmacy for a specific person or set of symptoms.

The present tools and methods also provide for informing therapeutic dosing decisions. It is often the case that many patients do not respond best to the initially prescribed dose of one or more drugs. The process of 'fine tuning' the selection of the optimal dose range at present is not driven by quantitative or neurobiologically principled methods but rather a clinican's qualitative assessment of the patient or the patient's self-report. Consequently, the process of fine tuning dosing decisions often difficult to precisely optimize. Therefore, the present tools and methods provide for a method of use to select and optimize dose ranges for a specific person or set of symptoms based on similarity of a derived neurobehavioral phenotype map to the gene transcriptome profile or gene expression map as a function of different doses. Relatedly, the present tools and methods provide a method of use whereby the initial pre-treatment neurobehavioral phenotype mapping alignment with a given gene expression map provides a guide to potentially optimize a dose level.

The present tools and methods also provide for informing exclusion of drug targets. It is often the case that many patients do not respond at all or respond poorly to a given treatment of choice that may be indicated for the broad range of symptoms the person is experiencing. At present, there is no quantitative or neurobiologically principled methods to decide prior to treatment if a given drug may be a poor candidate for a given neural circuit. Therefore, there is high risk of no response or poor response to a given drug or dose. The present tools and methods provide a method of use to inform which drugs or dose ranges may be exclusionary for a specific person or set of symptoms based on dissimilarity of a derived neurobehavioral phenotype map to the gene transcriptome profile or gene expression map.

The present tools and methods also provide for informing differential neurobehavioral phenotype clinical response to a given treatment. At present it is difficult to make decisions in humans which of the two or more drugs may be optimal for a given neural circuit based on behavioral efficacy. Specifically, if two drugs induce differential symptom response in a clinical trial then the known alignment of their receptor targeting with a given transcriptome map or gene expression map implicates a neural circuit in that symptom change. This method of use provides guidance in the context of clinical trial design concerning which drug may be optimal for a given pipeline of development and targeting of specific circuits.

In some embodiments, the present tools and methods provide a method of detecting a neurobehavioral phenotype in a subject, said method comprising: obtaining or having obtained a sample of neurobehavioral phenotype mapping data from the subject; defining a genotype topography of a first brain area for a gene based on gene expression mapping data; defining a neurophenotype topography of a second brain area for the neurobehavioral phenotype based on neurobehavioral phenotype mapping data; contacting the genotype topography of the first brain area and the neurophenotype topography of the second brain area to establish an alignment; detecting whether the neurobehavioral phenotype is present in the sample by contacting the sample with the aligned genotype topography and neurophenotype topography. In an embodiment of this method, the neurobehavioral phenotype is at least one of: an affective disorder, a personality disorder, an attention deficit hyperactivity disorder, a neurodegenerative disease, a neurodevelopmental disorder, a cognitive change associated with chemotherapy; a psychiatric symptom associated with neurodegenerative diseases, a sex difference in brain function in health and disease, a traumatic brain injury, and a measurable neural feature.

In some embodiments, the present tools and methods provide a method of diagnosing, predicting, prognosticating, or treating a neurobehavioral phenotype in a subject, said method comprising: obtaining or having obtained a sample of neurobehavioral phenotype mapping data from the subject; defining a genotype topography of a first brain area for a gene based on gene expression mapping data; defining a neurophenotype topography of a second brain area for the neurobehavioral phenotype based on neurobehavioral phenotype mapping data; contacting the genotype topography of the first brain area and the neurophenotype topography of the second brain area to establish an alignment; detecting whether the neurobehavioral phenotype is present in the sample by contacting the sample with the aligned genotype topography and neurophenotype topography; and diagnosing, predicting, prognosticating, or treating the subject when the neurobehavioral phenotype is detected. In an embodiment, this method further comprises administering a therapeutic agent to the subject. In an embodiment, this method further comprises identifying one or more therapeutic agents suitable for treatment of the detected neurobehavioral phenotype. In an embodiment, this method includes one or more therapeutic agents are selected based on a gene associated with the detected neurobehavioral phenotype. In an embodiment, this method includes one of more of the PDYN, OXTR, OPRK1, PNOC, OXT, AVP, OPRL1, APOE, GRIN2C, GABRA2, HTR2A, HTR3A, HRTR2C, HTR6, MAOA, CHRM1, CHRM3, CCR5, CXCR4, CXCR7, HRH3, ADRB2, DRD2, SNCA, GBA, GPR88, GPR139, and LRRK2 genes. In an embodiment, this method further comprises identifying gene expression targets associated with the detected neurobehavioral phenotype. In an embodiment, this method further comprises combining one or more therapeutic agents indicated to be suitable for treatment of the detected neurobehavioral phenotype. In an embodiment, this method further comprises dosing of one or more therapeutic agents in amounts indicated to be effective for treatment of the detected neurobehavioral phenotype. In an embodiment, this method further comprises selecting a therapeutic agent indicated to be most suitable for treatment of the detected neurobehavioral phenotype. In an embodiment, this method further comprises not administering one or more therapeutic agents to the subject indicated to not be suitable for treatment of the detected neurobehavioral phenotype. In an embodiment, this method includes one or more therapeutic agents that is shown to have activity in a brain area outside the alignment of the first brain area and the second brain area. In an embodiment, this method includes repeating one or more steps of the method after the subject has been diagnosed, prognosticated to be at risk for, or treated for the detected neurobehavioral phenotype. In an embodiment, this method further comprises altering a therapeutic regimen for the subject based on changes in the detected neurobehavioral phenotype. In an embodiment, this method further comprises selecting the subject for inclusion in a clinical study. In an embodiment, this method further comprises forming a patient population suitable for inclusion in the clinical study. In an embodiment, this method includes a neurobehavioral phenotype that is one of: an affective disorder such as obsessive compulsive disorder, bipolar disorder, unipolar depression, dysthymia and cyclothymia, generalized anxiety disorder, panic disorder, phobias, and post-traumatic stress disorder; a personality disorder such as schizophrenia, paranoid personality disorder; schizoid personality disorder; schizotypal personality disorder; antisocial personality disorder; borderline personality disorder; histrionic personality disorder; narcissistic personality disorder; avoidant (or anxious) personality disorder; dependent personality disorder; and obsessive compulsive personality disorder; an attention deficit hyperactivity disorder such as inattentive type, hyperactive-impulsive type, and combination type; a neurodegenerative diseases such as Alzheimer's disease, Parkinson's disease; amyotrophic lateral sclerosis; Friedreich's ataxia; Huntington's disease; Lewy body disease; and spinal muscular atrophy; a neurodevelopmental disorders such as autism spectrum disorder, attention-deficit/hyperactivity disorder (ADHD) and learning disorders; cognitive changes associated with chemotherapy; a psychiatric symptom associated with neurodegenerative diseases such as feeling sad or down, confused thinking or reduced ability to concentrate, excessive fears or worries, or extreme feelings of guilt, extreme mood changes of highs and lows, withdrawal from friends and activities, significant tiredness, low energy or problems sleeping, detachment from reality (delusions), paranoia or hallucinations, inability to cope with daily problems or stress, trouble understanding and relating to situations and to people, alcohol or drug abuse, major changes in eating habits, sex drive changes, excessive anger, hostility or violence, and suicidal thinking; a sex differences in brain function in health and disease; a traumatic brain injury; and any measurable neural feature. In an embodiment, this method includes a subject that does not undergo invasive pharmacoimaging.

In some embodiments, the present tools and methods provide a method for treating a subject with a neurobehavioral phenotype, the method comprising the steps of: determining whether the subject has neurobehavioral phenotype mapping data indicative of the neurobehavioral phenotype by: obtaining or having obtained a sample of neurobehavioral phenotype mapping data from the subject; defining a genotype topography of a first brain area for a gene based on gene expression mapping data; defining a neurophenotype topography of a second brain area for the neurobehavioral phenotype based on neurobehavioral phenotype mapping data; contacting the genotype topography of the first brain area and the neurophenotype topography of the second brain area to establish an alignment; performing or having performed a comparison of the sample with the aligned genotype topography and neurophenotype topography to determine if the subject has the neurobehavioral phenotype; and (i) if the subject has the neurobehavioral phenotype as determined by comparison of the sample with the aligned genotype topography and neurophenotype topography, then administering a therapeutic agent targeted to one or more genes associated with the aligned genotype topography and neurophenotype topography, or (ii) if the subject has the neurobehavioral phenotype as determined by comparison of the sample with the aligned genotype topography and neurophenotype topography, then administering a therapeutic agent targeted to one or more neurobehavioral phenotypes associated with the aligned genotype topography and neurophenotype topography. In an embodiment, this method further comprises increasing the likelihood that the treatment for the subject will be effective for treatment of the neurobehavioral phenotype.

In some embodiments, the present tools and methods provide a method of detecting a neurobehavioral phenotype in subjects of a patient population, said method comprising: obtaining or having obtained a sample of neurobehavioral phenotype mapping data from each subject in the patient population; defining a neurophenotype topography of a second brain area for the neurobehavioral phenotype based on neurobehavioral phenotype mapping data; contacting the genotype topography of the first brain area and the neurophenotype topography of the second brain area to establish an alignment; detecting whether the neurobehavioral phenotype is present in the sample by contacting the sample with the aligned genotype topography and neurophenotype topography.

EXAMPLES

Example 1: Gene Expression Maps for Genes of Interest and Map Validation

The present inventors developed algorithms to produce group-averaged parcellated gene expression maps from the AHBA dataset.

Figure 6A:
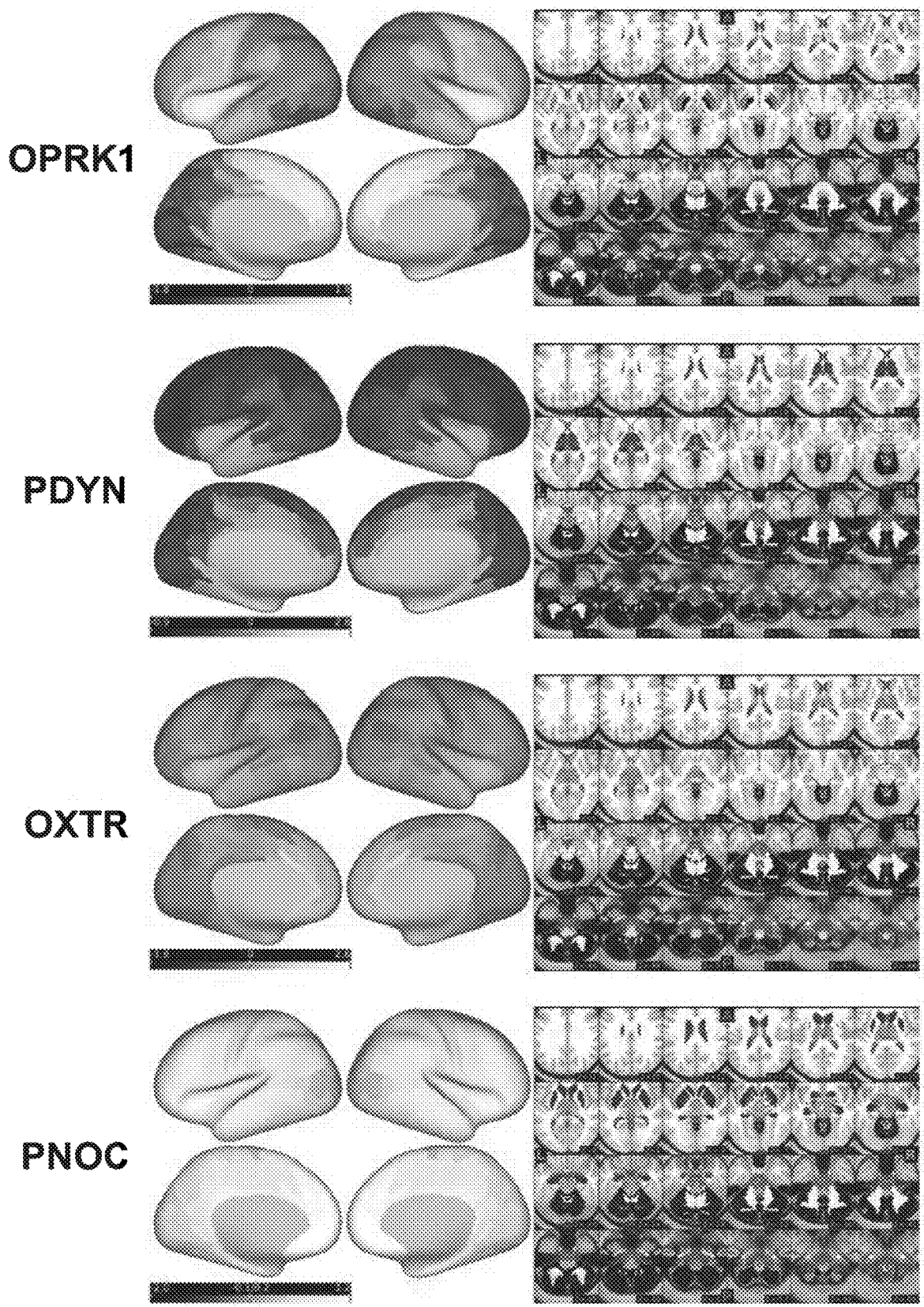
FIGS. 6A, 6B, and 6C provide an example of cortical and subcortical gene group-averaged expression maps for four genes, OPRK1, PDYN, OXTR, and PNOC.
Figure 6B:
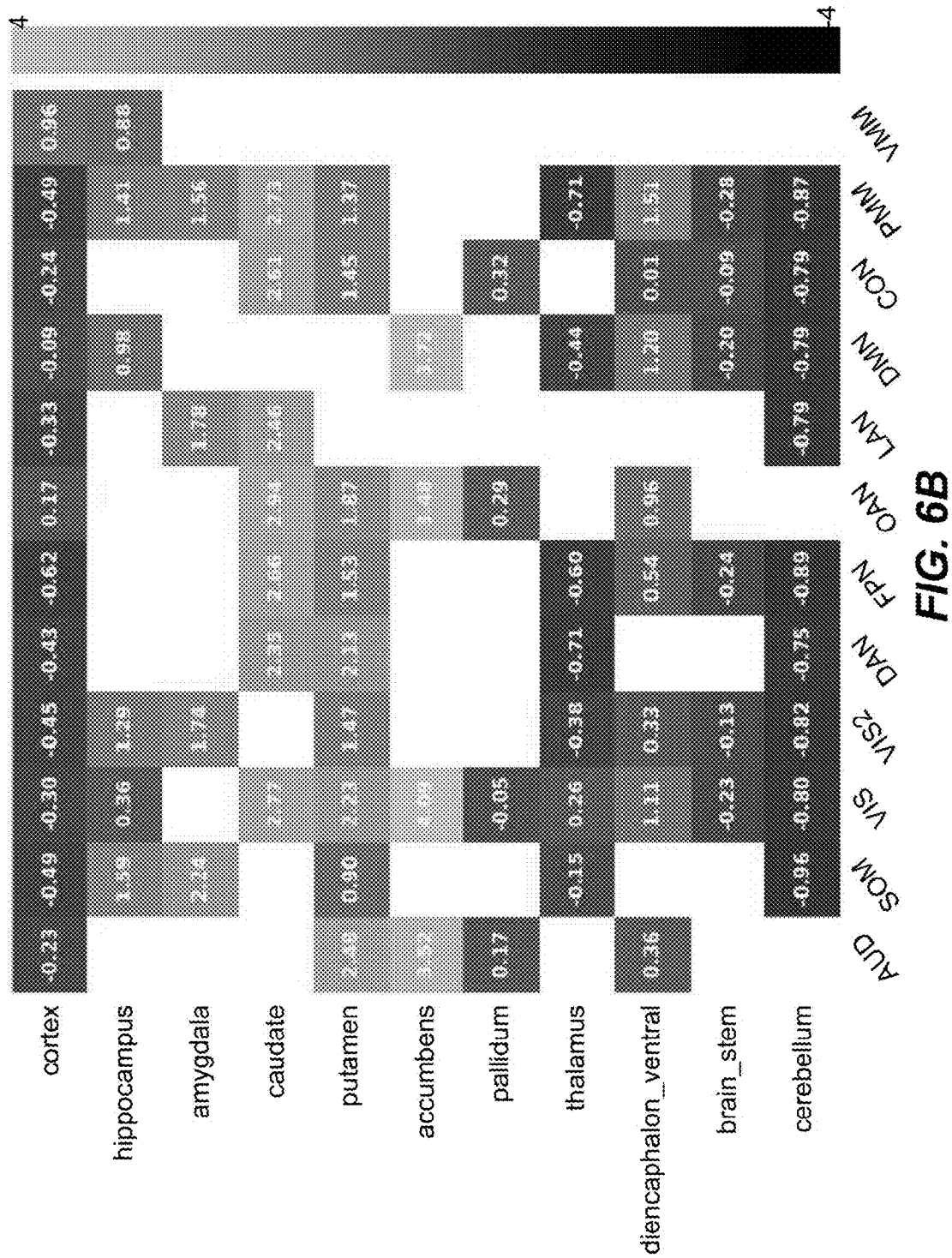

FIG. 6A shows these parcellated group-averaged expression maps for four genes of interest (OPRK1, PDYN, OXTR, and PNOC) in cortex (left) and subcortex (right). These maps reveal substantial yet systematic variation and structure in the expression patterns for these genes across cortex and subcortical structures. For instance, within cortex, PDYN shows high expression in anterior/medial temporal and medial prefrontal regions, but low expression in lateral prefrontal regions. Gene expression patterns can also be analyzed and visualized by their mean values across gross brain structures (e.g., cortex, caudate, thalamus, cerebellum), and across different functionally defined brain networks (e.g., auditory (AUD), somatomotor (SOM), visual (VIS)). FIG. 6B shows this structure-by-network analysis for the gene PDYN, which shows that PDYN has high expression in structures of the striatum (caudate, putamen, accumbens).

The validity of gene expression maps for serotonin receptors was assessed through correspondence with PET maps because biological validity of these gene expression maps is crucial to the ability to interpret their meaning and apply them to inform therapeutic targets. Validity and interpretability can be supported through convergent evidence from another experimental methodology, such as PET imaging. For instance, validity is supported by observation of a high similarity between the PET-derived map for the density of a given binding target (which may be closer to 'ground truth') and the expression map for the gene coding for that binding target. Shown are juxtaposed PET and gene expression maps for multiple serotonin receptor subunits, using the PET maps from the following article, Beliveau et al., *A high-resolution in vivo atlas of the human brain's serotonin system*, J. NEUROSCI. (2016) ("Beliveau").

A strong overall correspondence was found between PET and gene expression maps. For instance, in both maps, the 5-HT1AR subunit (encoded by the gene HTR1A) has low levels in primary visual cortex and high levels in anterior temporal cortex, whereas the 5-HT2AR subunit (encoded by the gene HTR2A) has high levels in primary visual cortex. This correspondence between measures provides support for the biological validity and interpretability of the gene expression maps.

Figure 6C:
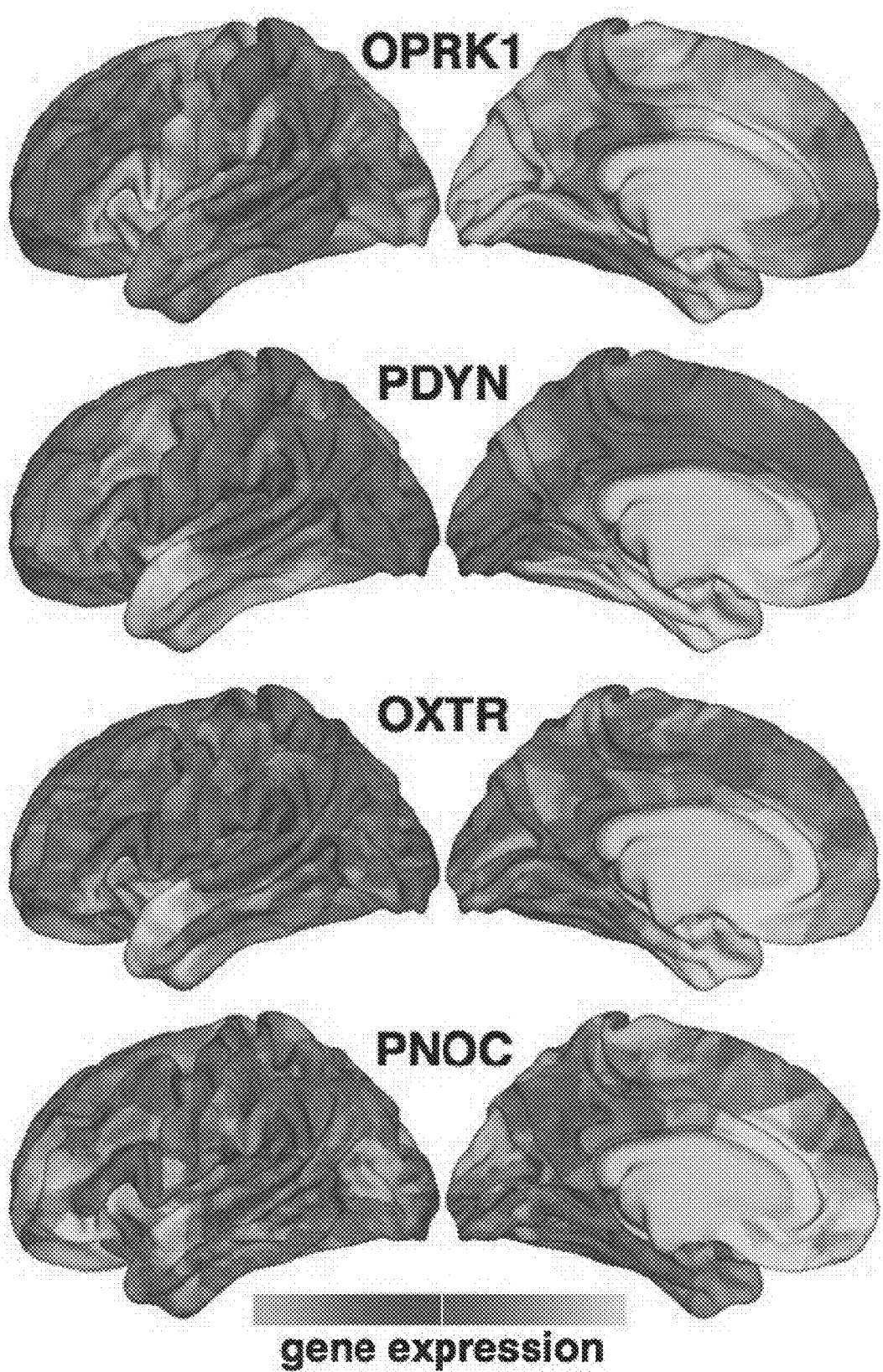

FIG. 6C also provides images of the dense (in contrast to parcellated) cortical maps of gene expression for OPRK1, PDYN, OXTR, and PNOC.

Example 2: Opposing Correlations with T1w/T2w (Myelin) Map for Two $GABA_A$ Receptor Subunit Genes: GABRA1 and GABRA5

A crucial step in the present platform is measuring the similarity between a gene expression map and a neuroimaging map. As a test case for a neurophenotype map, the present inventors used the map of T1w/T2w ratio which is derived from structural MRI (i.e., ratio of T1-weighted and T2-weighted MRI images). Glasser et al., *Trends and properties of human cerebral cortex: correlations with cortical myelin content*, NEUROIMAGE 93 Pt 2:165-75 (2014). The T1w/T2w map functions as an interpretable neurophenotype map because it captures microstructural specialization of cortical areas related to the hierarchical organization of cortex. Burt. The T1w/T2w map has high values in sensory cortex and low values in association cortex. Therefore if a cortical gene expression pattern exhibits a positive correlation with the T1w/T2w map, it is well distributed to preferentially modulate sensory cortex; conversely, if a cortical gene expression pattern exhibits a negative correlation with the T1w/T2w map, it is well distributed to preferentially modulate association cortex.

FIGS. 7A-7E shows the relationship between the T1w/T2w map and expression maps for two genes coding for subunits of the GABAA receptor: GABRA1 and GABRA5, which encode the α1 and α5 subunit, respectively. The α1 and α5 GABAA subunits have different biophysical properties, cellular distributions, and developmental trajectories. Gonzalez-Burgos et. al, *GABA neurons and the mechanisms of network oscillations: implications for understanding cortical dysfunction in schizophrenia*, SCHIZOPHR. BULL. 34:944-961 (2008); Datta et al., *Developmental expression patterns of gabaa receptor subunits in layer 3 and 5 pyramidal cells of monkey prefrontal cortex*, CEREB. CORTEX 25:2295-305 (2015).

In pyramidal neurons, the a1 subunit is in intra-synaptic receptors that are preferentially distributed in the peri-somatic region and activated by parvalbumin-expressing interneurons, and has fast kinetics. In contrast, the α5 subunit is in extra-synaptic receptors that are preferentially distributed in the distal dendritic regions and activated by somatostatin-expressing interneurons, and has slow kinetics. They are also differentially sensitive to some drugs; for instance, α5 PAMs have been investigated for cognitive symptoms in schizophrenia. Gill et al., *The role of α5 gabaa receptor agonists in the treatment of cognitive deficits in schizophrenia*, CURR. PHARM. DES. 20:5069-76 (2014). Here, the inventors found opposing trends in their inter-areal distributions, in relation to the T1w/T2w map.

Figure 7A:
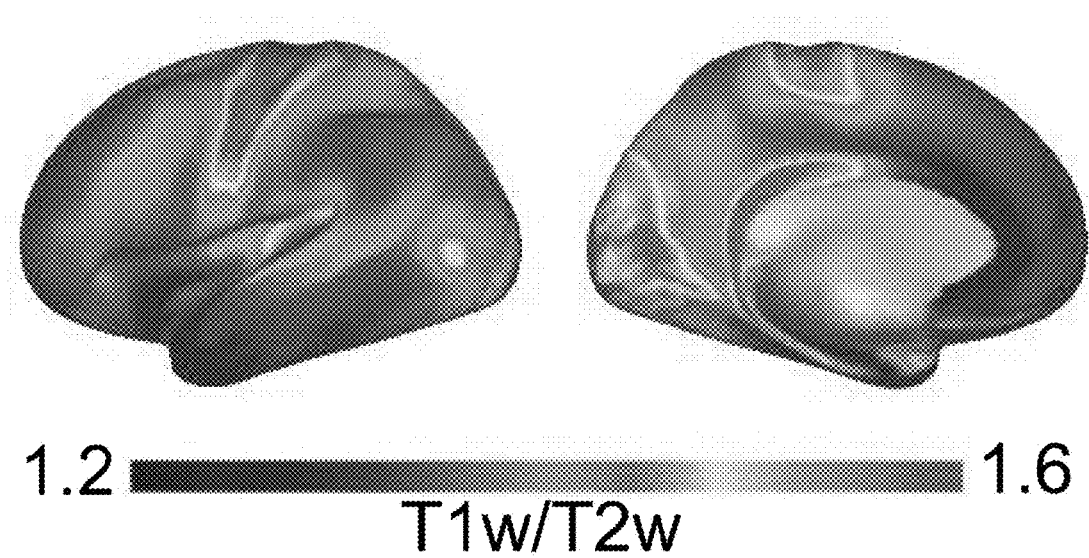
FIGS. 7A, 7B, 7C, 7D, and 7E provide opposing correlations with the T1w/T2w (myelin) map for two GABA receptor subunit genes, GABRA1 and GABRA5.
Figure 7B:
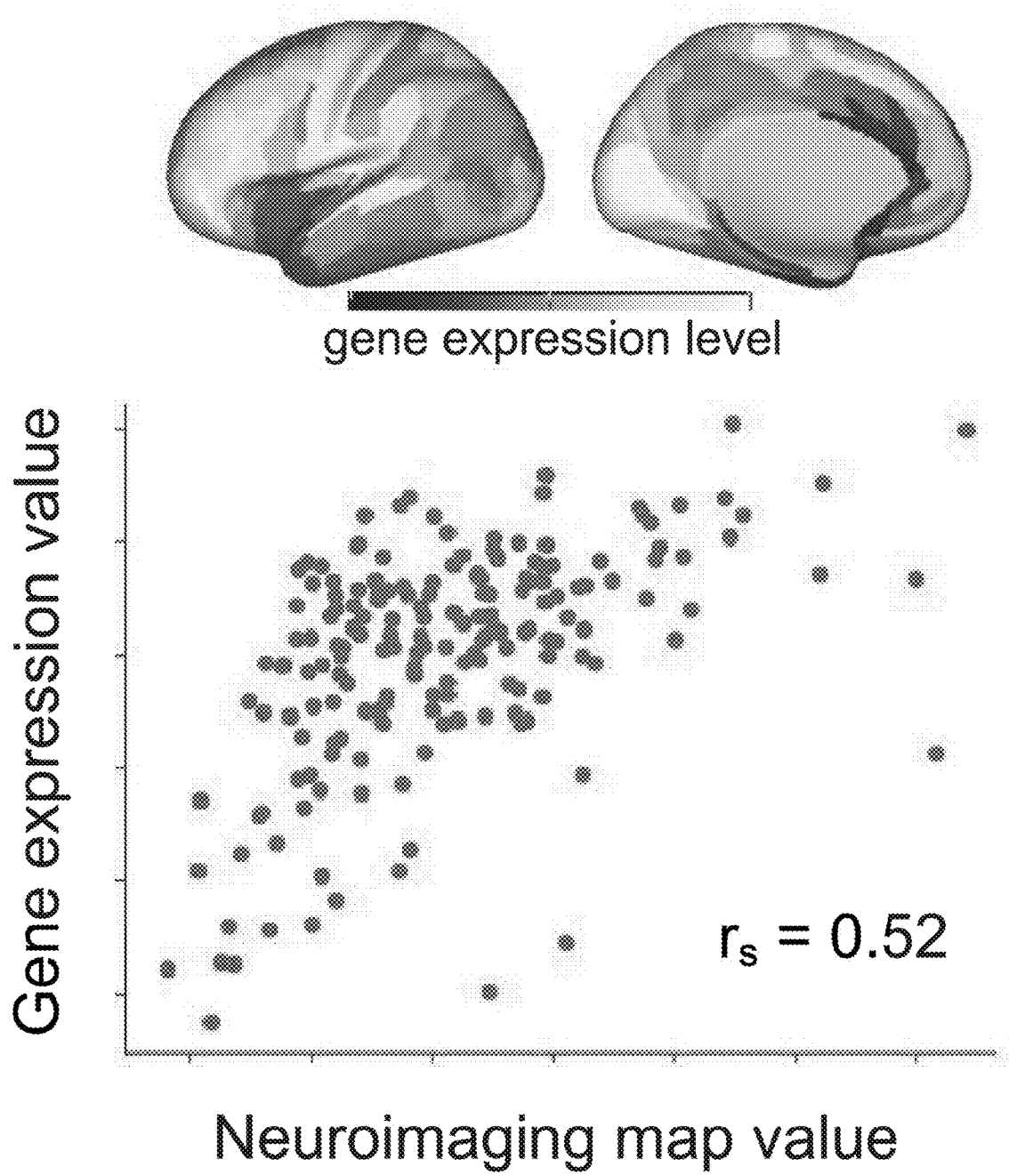
Figure 7C:
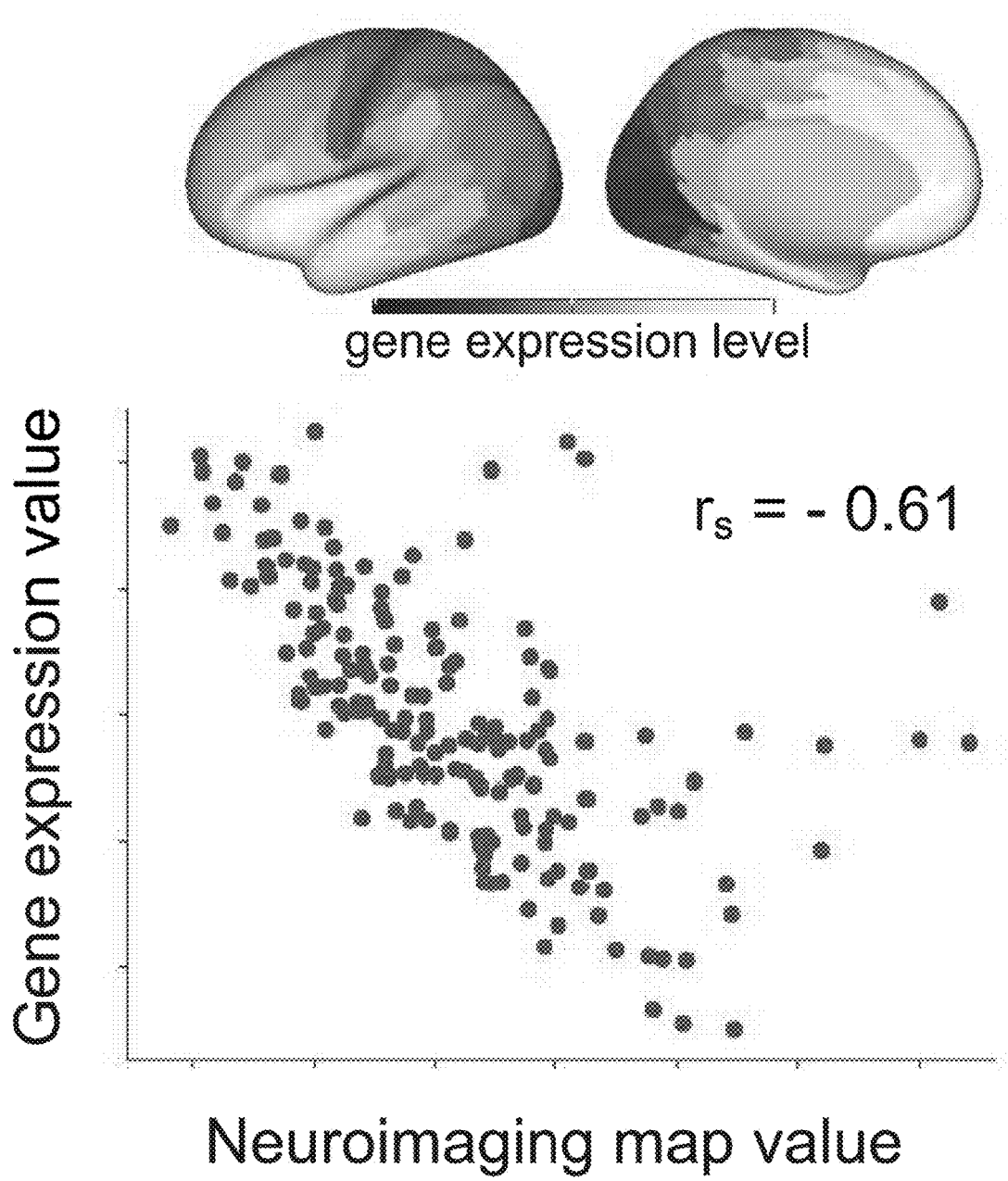

FIG. 7A shows the neurophenotype topography of the cortical T1w/T2w map, as an example neurophenotype map. FIG. 7B and FIG. 7C show the cortical gene expression maps, or genotype topographies, (top) for the genes GABRA1 and GABRA5, respectively, and their relationship with the neurophenotype map (bottom). GABRA1 expression exhibits a strong positive correlation with T1w/T2w (Spearman rank correlation, $r_s$=0.52), whereas GABRA5 exhibits a negative correlation ($r_s$=−0.61).

Figure 7D:
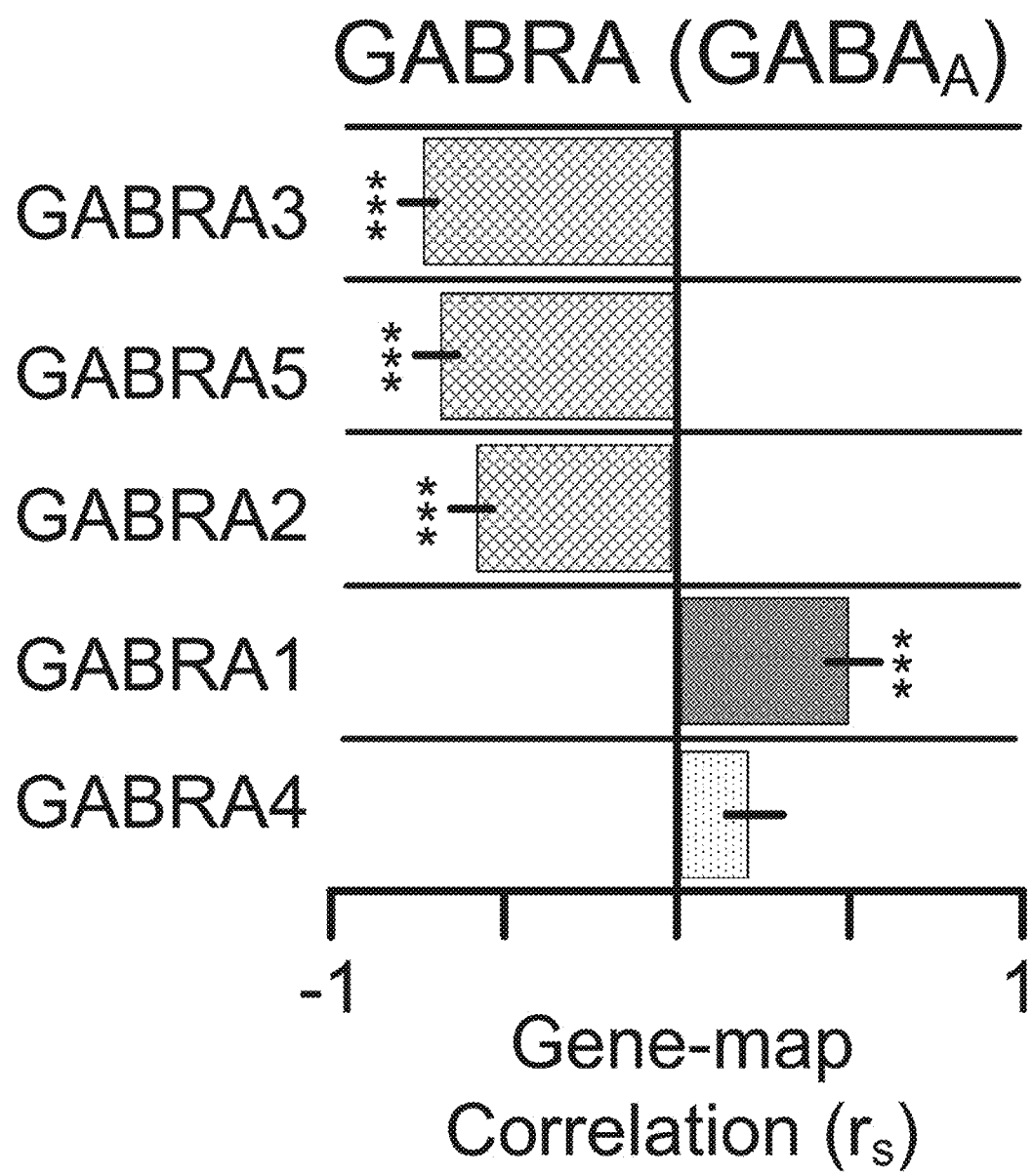

The platform also allows the user to sweep across and compare genes within a given set of genes, returning the gene-map alignment scores. FIG. 7D shows such results for the T1w/T2w map comparing across a set of GABAA receptor subunit genes (GABRA1, GABRA2, GABRA3, GABRA4, and GABRA5). This analysis shows that GABRA1 exhibits a strong positive correlation with the neurophenotype map, which is statistically significant; GABRA2, GABRA3, and GABRA5 exhibit strong negative correlations, which are statistically significant; GABRA4 exhibits a weak correlation that is not statistically significant. These findings demonstrate the feasibility of the present platform, demonstrating that it can reveal significant structured relationships between gene expression maps and neurophenotype maps.

These findings derived from the platform can inform actionable decisions in development and application of therapeutics, with multiple methods of use. For example, one can examine a case in which the goal were to treat disinhibition preferentially in higher association areas (low T1w/T2w values) relative to primary sensory areas (high T1w/T2w values). This is plausible because multiple neuropsychiatric and neurological disorders may involve preferential alteration in association cortical areas, relative to sensory cortical areas. Informing this example goal, these specific findings provide evidence that an α5 PAM may be more effective than an a1 PAM at maximizing effects on prioritized target areas while minimizing effects on off-target areas. This evidence could be used to inform design of clinical trials, to better align a patient population (e.g., for a disorder exhibiting with association vs. sensory cortical alterations) with a pharmacological drug (e.g., ones preferentially modulating association vs. sensory cortical regions). The correlation between these maps' values can serve as the quantitative score of similarity for the gene-map pair. These results demonstrate meaningful variation of gene expression patterns even for two subunits of the same receptor, which can be related to neuroimaging maps.

Figure 7E:
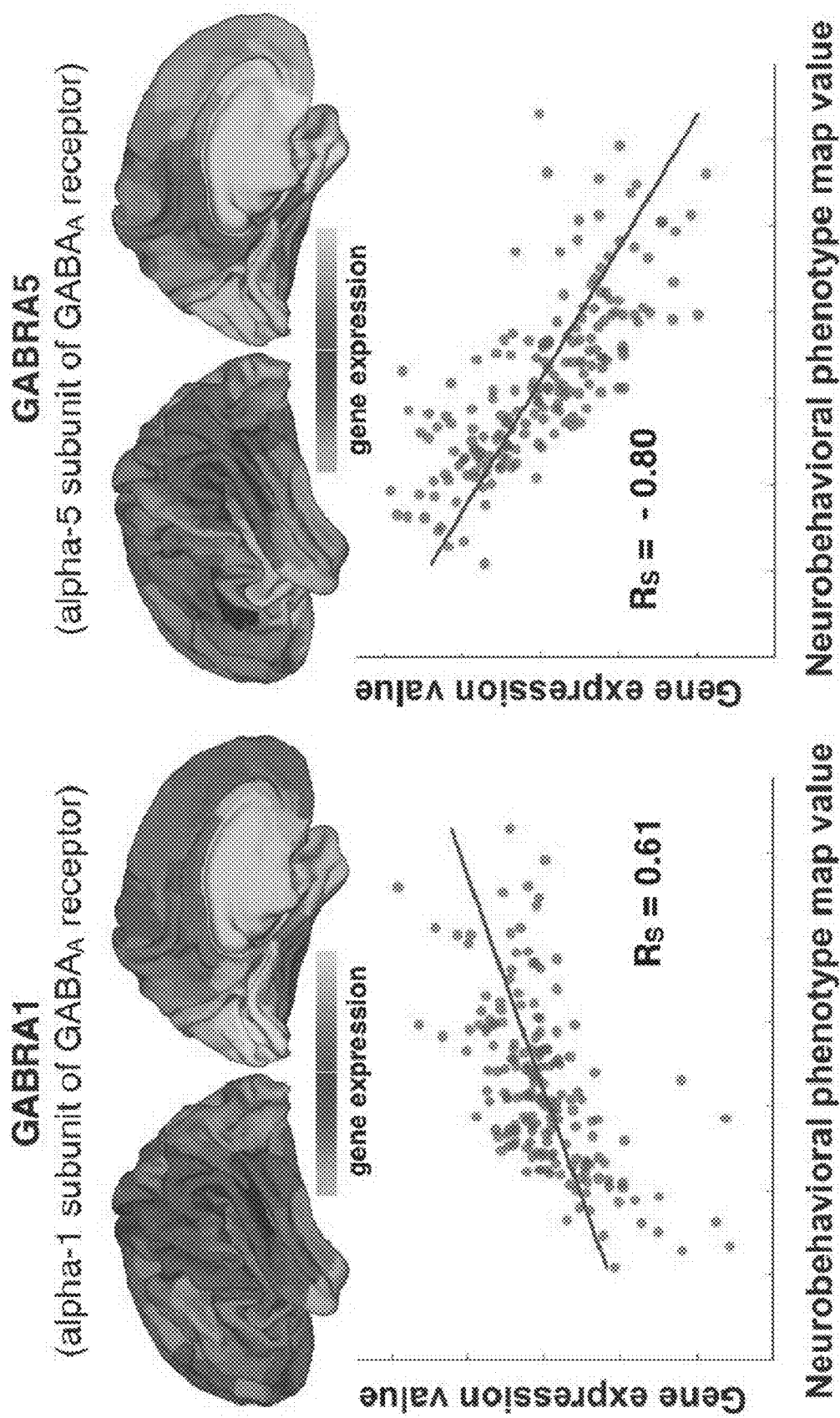

FIG. 7E shows images from another embodiment of the present platform. The results indicated here differ quantitatively, but not qualitatively, from those provided in FIG. 7B and FIG. 7C, for reasons that include, but are not necessarily limited to, methodological differences in surface based mapping and interpolation method (parcellated vs. dense) used to generate the figures.

Example 3: Gene-Map Correlations for Genes of Interest

Figure 8:
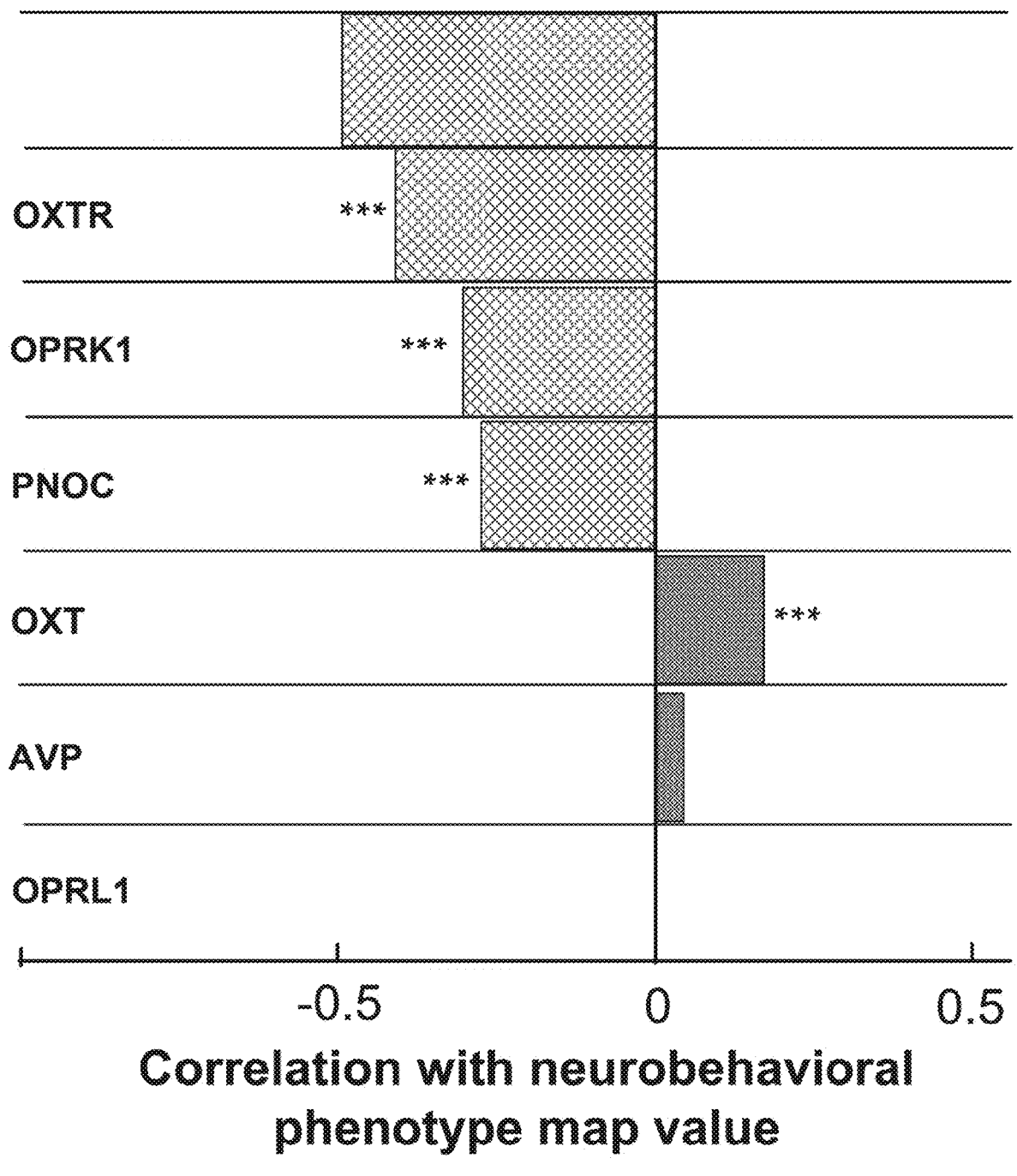
FIG. 8 provides a correlation between gene expression and the T1/T2w (myelin) map for seven (7) genes, PDYN, OXTR, OPRK1, PNOC, OXT, AVP, and OPRL1.

FIG. 8 shows scores, here the correlation with the T1w/T2w (myelin) map, for seven genes of interest (PDYN, OXTR, OPRK1, PNOC, OXT, AVP, and OPRL1). The inventors found that four of the seven genes had highly significant negative correlations with T1w/T2w (myelin) map values (PDYN, OXTR, OPRK1, and PNOC), only one gene had a significant positive correlation (OXT), and two genes did not have a significant correlation (AVP, OPRL1).

These findings demonstrate the feasibility of the present platform, demonstrating that it can reveal significant structured relationships between gene expression maps and neuroimaging maps.

Example 4: Proof-of-Principle Demonstrations of Platform Bi-Directionality

FIGS. 9A, 9B, 10A, and 10B provide proof-of-principle demonstrations of the bi-directional platform, using HCP task activation maps.

Figure 9A:
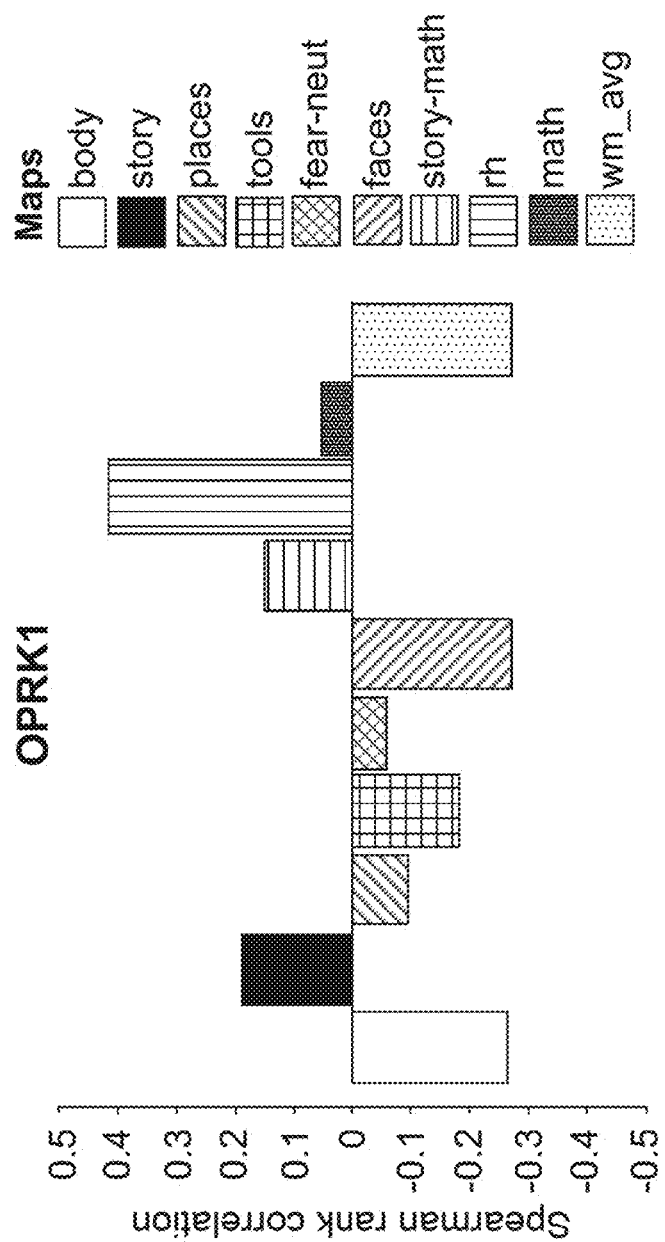
FIGS. 9A and 9B provide a proof-of-principle demonstration showing the bi-directionality of the platform using HCP task activation maps.
Figure 9B:
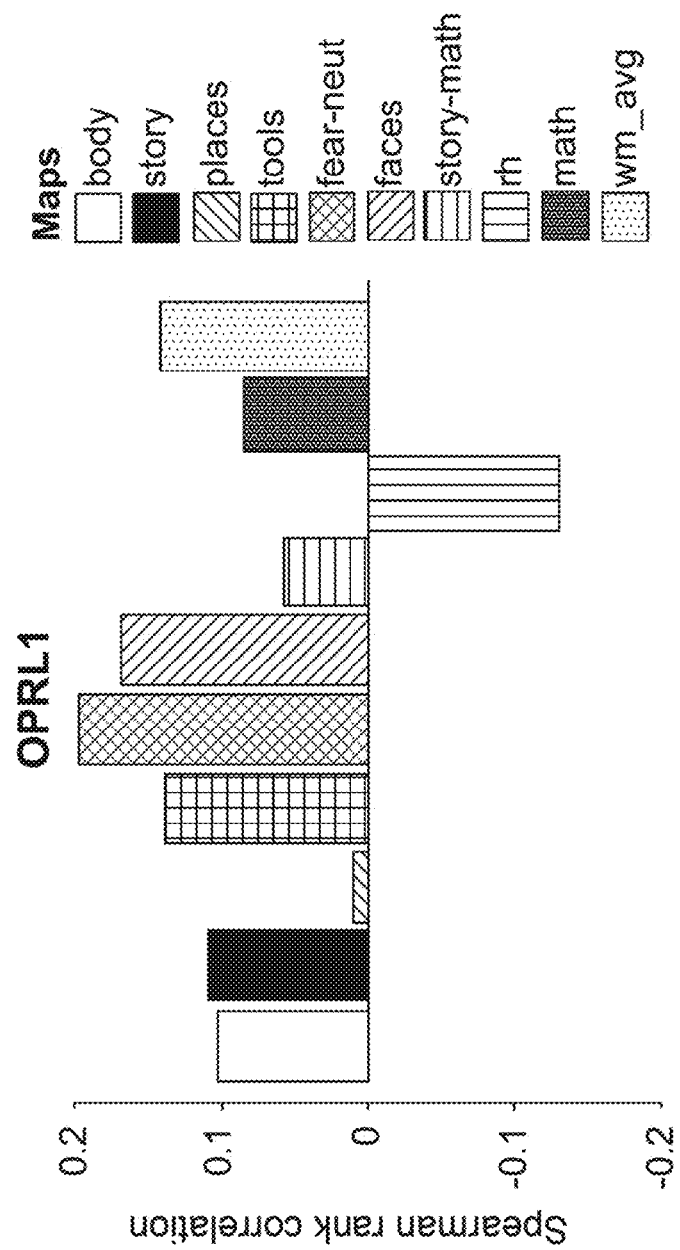

FIGS. 9A and 9B depict a gene-to-phenotype approach. Here, the proof-of-principle implementation flows in the direction from a gene as therapeutic target to neurobehavioral phenotypes, corresponding to FIG. 5A. The set of example neurophenotype maps was calculated from fMRI-derived task activation maps for cortex, for specific tasks from the Human Connectome Project. For FIG. 9A the gene expression map is that of OPRK1 and for FIG. 9B is that of OPRL1. Plotted is the correlation between the cortical gene expression map and each of a set of neurobehavioral phenotype maps. The gene-phenotype score (here the spearman rank correlation) varies markedly across neurobehavioral phenotypes, differently for the two example genes.

Figure 10A:
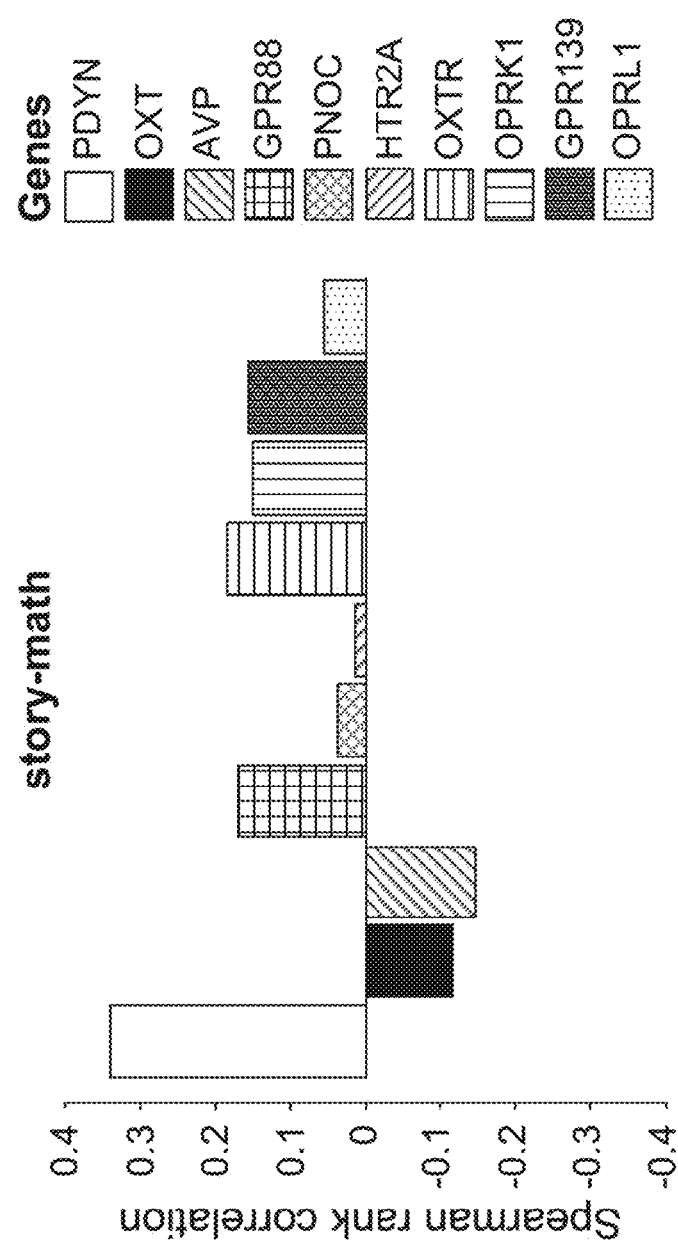
FIGS. 10A and 10B provide another proof-of-principle demonstration showing the bi-directionality of the platform using HCP task activation maps.
Figure 10B:
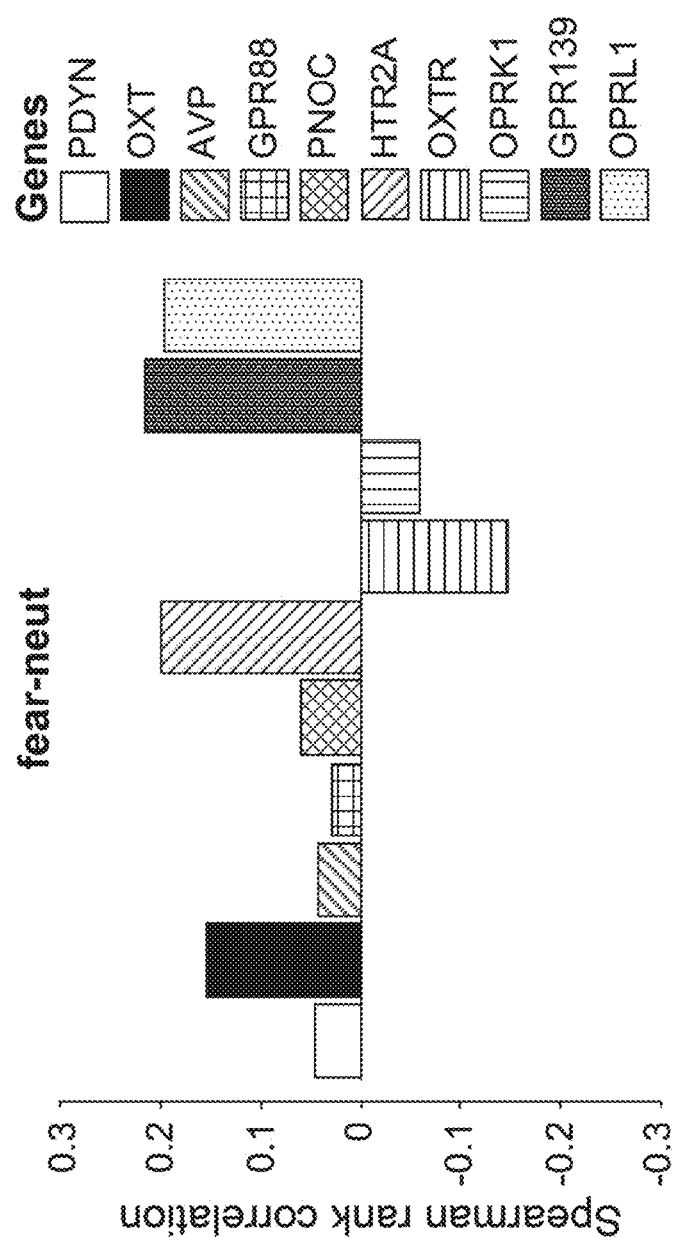

FIGS. 10A and 10B depict a phenotype-to-gene approach. Here, the proof-of-principle implementation flows in the direction from a neurobehavioral phenotype to genes as therapeutic targets, corresponding to FIG. 5B. Each of the two example neurophenotype maps was calculated as the contrast between two fMRI-derived task activation maps for cortex, for specific tasks from the Human Connectome Project. For FIG. 10A the phenotype map is the contrast between story vs. math tasks (to isolate language processing), and for FIG. 10B it is the contrast between presentation of fearful vs. neutral face stimuli (to isolate fear processing). Plotted is the correlation between the neurobehavioral phenotype map and each of a set of gene expression maps, for various genes which may encode for drug targets. The gene-phenotype score (here the spearman rank correlation) varies markedly across genes, differently for the two example neurobehavioral phenotypes.

Such bi-directional sweeps, across phenotypes for a given gene of interest and across genes for a given phenotype, can inform actionable decisions for multiple methods of use, such as: selecting tasks or behavioral measures to evaluate efficacy of given a drug in a clinical trial (in the gene-to-phenotype direction), or identifying and selecting candidate drug targets for a given behavioral or cognitive deficit (in the phenotype-to-gene direction).

Example 5: Gene-to-Gene Alignment for the Gene APOE

Figure 11A:
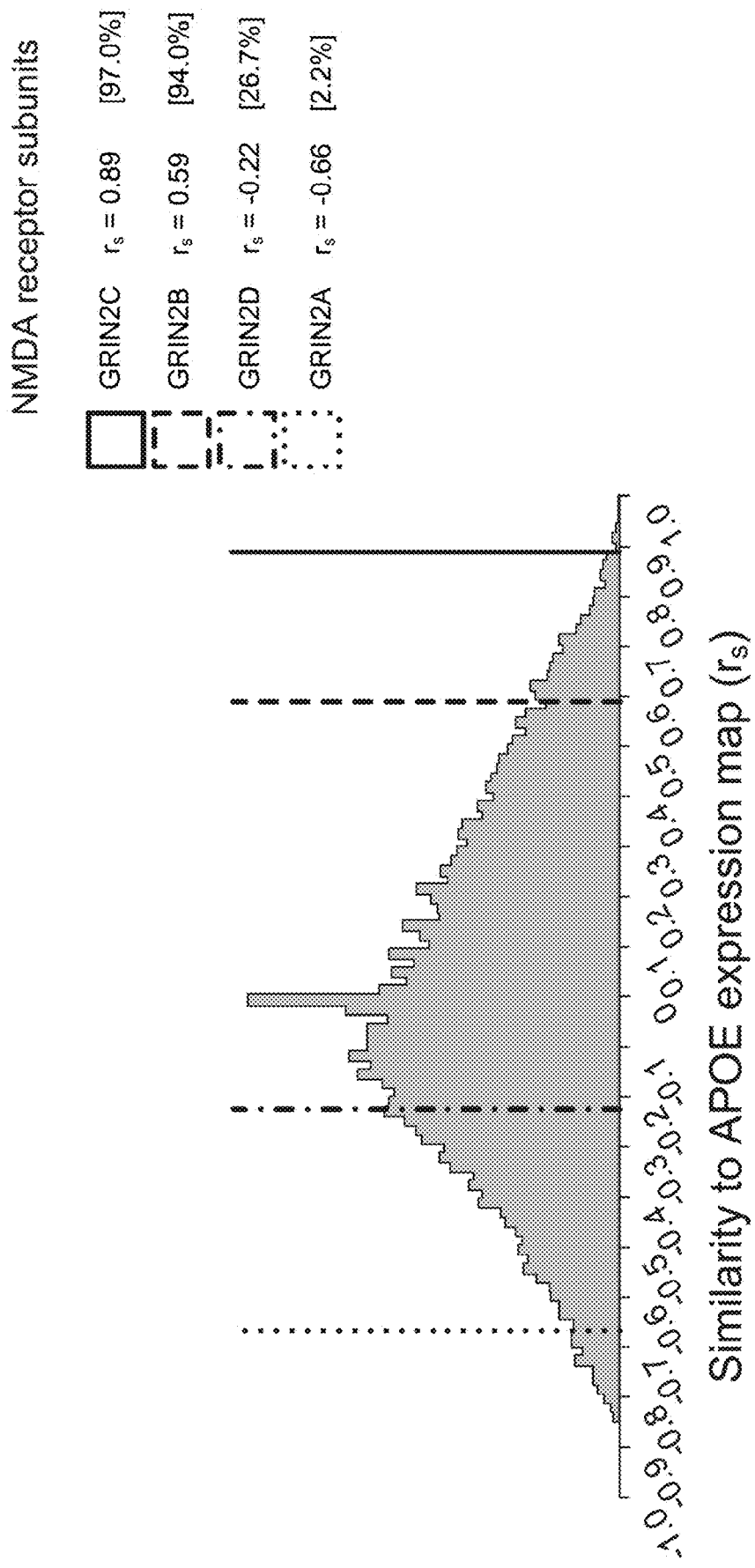
FIGS. 11A and 11B illustrate a gene-to-gene approach.
Figure 11B:
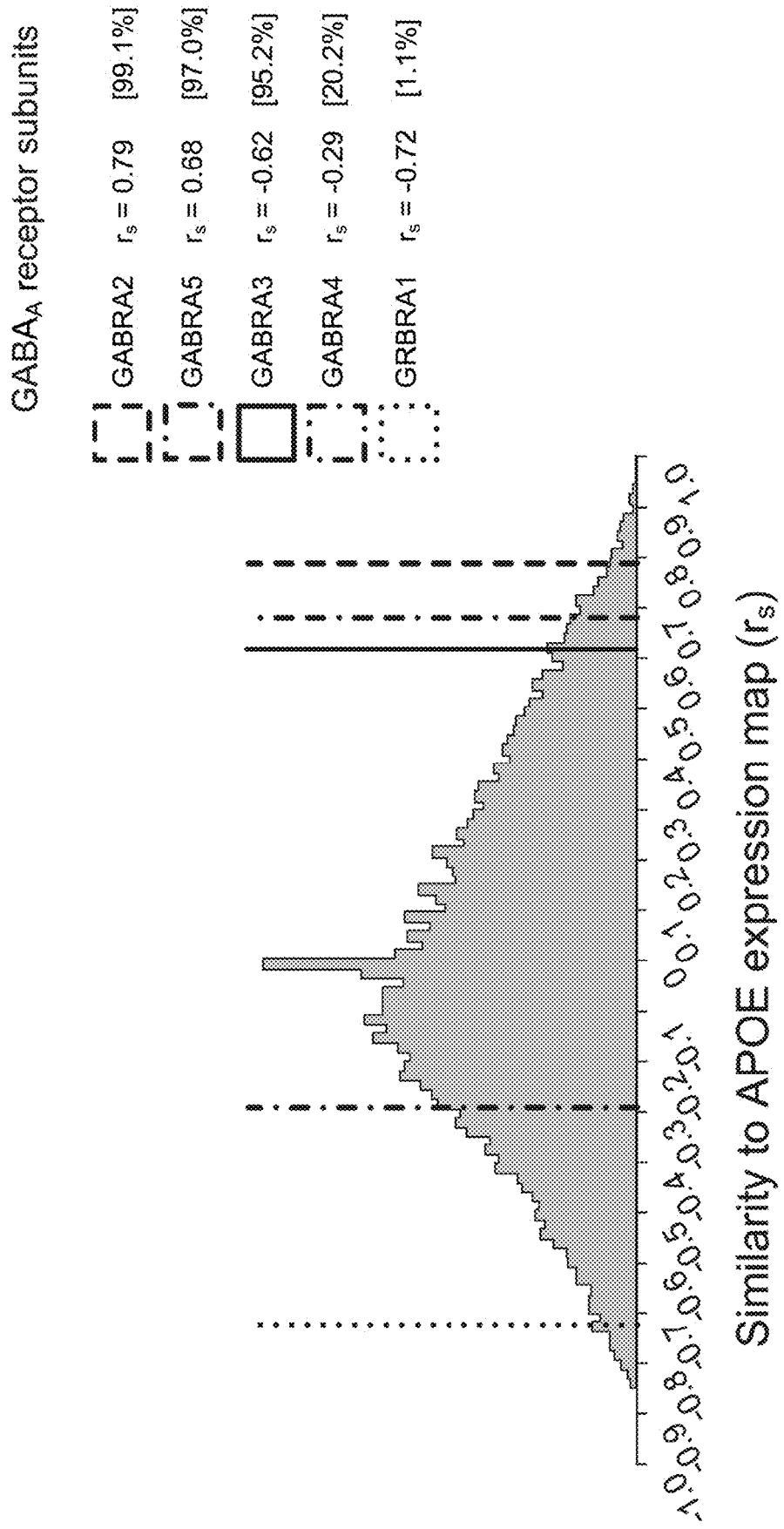

One method of use is identification of drug targets based on similarity to a gene implicated in a given disorder or process, corresponding to direction (C) in FIG. 5. For instance, the gene APOE is important in Alzheimer's disease. Because APOE and its associated protein have proven difficult to modulate pharmacologically, a therapeutic strategy may be modulate another drug target whose brain-wide gene expression pattern is aligned with that of APOE. The platform can identify such genes based on sweeping across genes and quantifying gene-to-gene alignment of expression patterns. FIGS. 11A and 11B illustrates a gene-to-gene approach. FIG. 11A shows the cortical gene similarity scores for four NMDA receptor subunits (GRIN2A, GRIN2B, GRIN2C, and GRIN2D). FIG. 11B shows the cortical gene similarity scores for four $GABA_A$ receptor subunits (GABRA1, GABRA2, GABRA3, GABRA4, and GABRA5). The background distribution histogram shows the distribution of scores across all available genes. These analyses show that among these gene sets, GRIN2C and GABRA2 have cortical expression topographies highly similar to APOE, and are in the top 1% of all available genes. This gene-to-gene alignment provides evidence that drugs which target the receptor proteins associated with GRIN2C and GABRA2 are well-distributed to preferentially modulate the same cortical regions that strongly express APOE. These results could inform identification and selection of genes with high alignment to APOE (e.g., GRIN2C and GABRA2) as potential therapeutic targets for Alzheimer's disease.

Example 6: Gene Expression Topography Relates to Brain-Wide Pattern of Pharmacological Effects of LSD Multiple methods of use evaluate alignment of a gene's expression map with a neuroimaging map related to a phenotype, to inform decision making about pharmacological therapeutics. The utility and feasibility of this approach, to make predictions for pharmacological therapeutics, can be supported by demonstrating that the brain wide effects of a drug on neuroimaging measures can be related to the gene expression topographies of the receptors modulated by that particular drug.

Figure 12C:
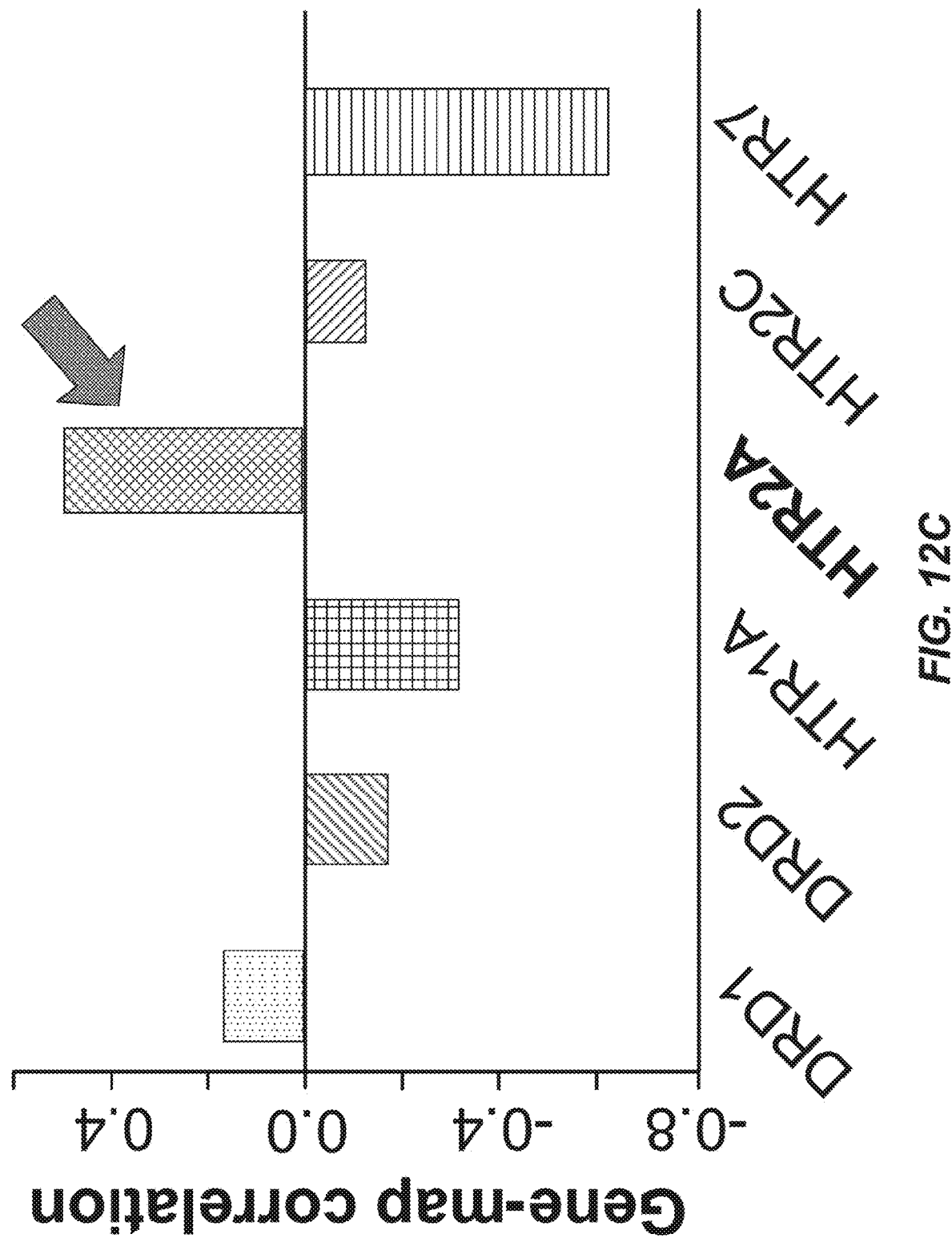
Figure 12D:
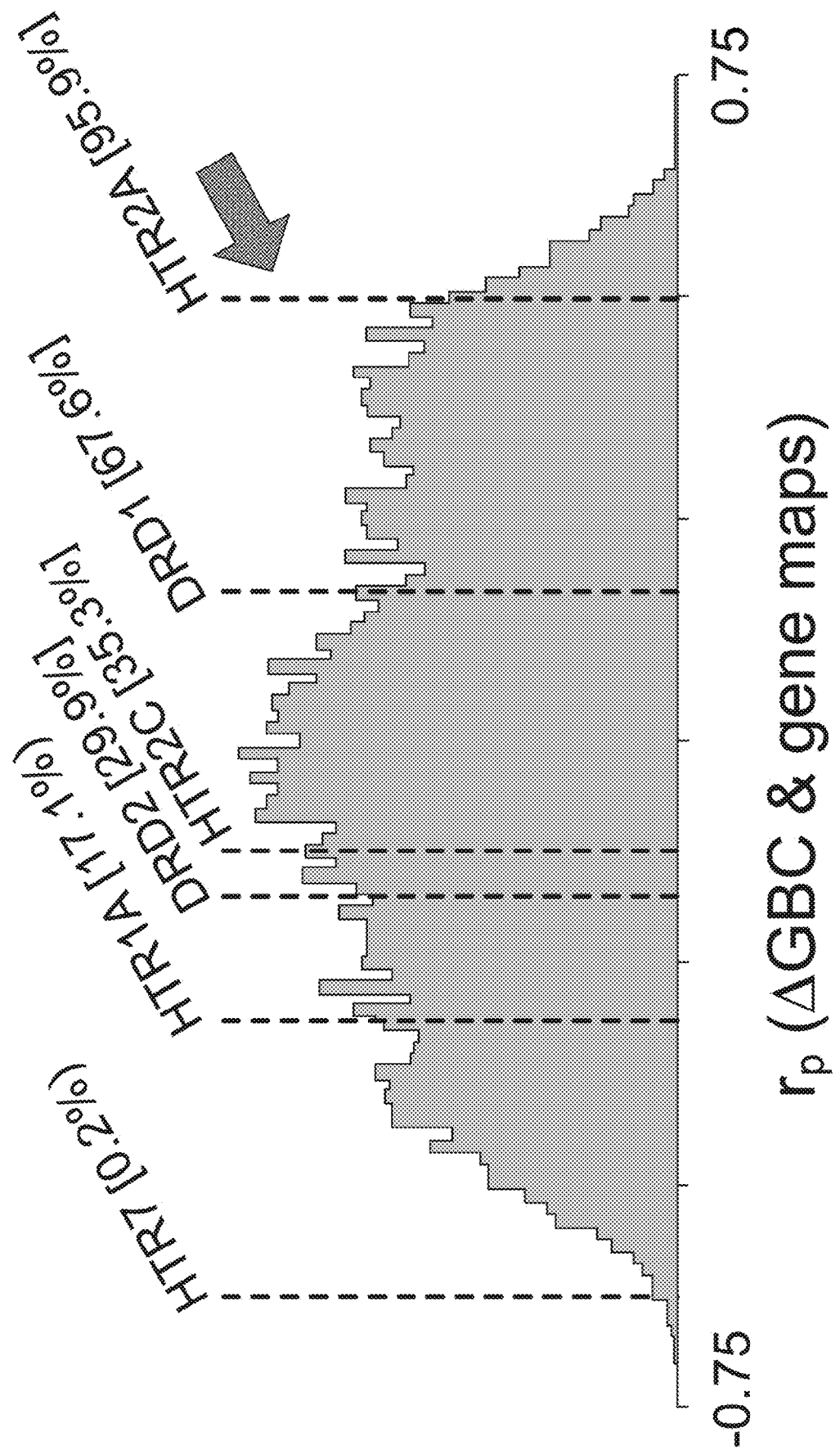

FIGS. 12A-12D show that the platform can link from gene expression patterns to the neural effects of a drug. In this study, resting-state fMRI was used to measure the change in functional connectivity induced by acute administration of lysergic acid diethylamide (LSD) in healthy human subjects. Preller et al., *Changes in global and thalamic brain connectivity in LSD-induced altered states are attributable to the 5-HT2A receptor*. ELIFE. (In Press) ("Preller"). FIG. 12A shows the fMRI-derived cortical map showing the change in mean functional connectivity (Global Brain Connectivity, GBC), which exhibits a large increase in occipital visual cortex. Importantly, this neural change, as well as behavioral effects of LSD, were found to be blocked by pre-administration with ketanserin, a selective antagonist of the 5-HT2A serotonin receptor. Preller. This finding strongly implicates the gene HTR2A, which codes for the 5-HT2A receptor, in the neural and behavioral effects of LSD. FIG. 12B shows gene expression maps for three serotonin receptor genes, including HTR2A. FIG. 12C shows the gene-map correlation between the LSD-related neurophenotype map and six candidate genes which code for serotonin and dopamine receptors. Among these six candidate genes, HTR2A exhibits the greatest alignment (i.e., highest positive correlation) with the LSD-related neurophenotype map. FIG. 12D shows these correlation values in relation to the gray background distribution histograms showing the distribution of scores across all available genes in the AHBA dataset, showing that HTR2A is in the top 5% of all genes in its alignment with the LSD-related neurophenotype map. Preller. This example illustrates the potential for the platform to predict the neural effects of pharmacology based on the topography of gene expression.

Figure 13A:
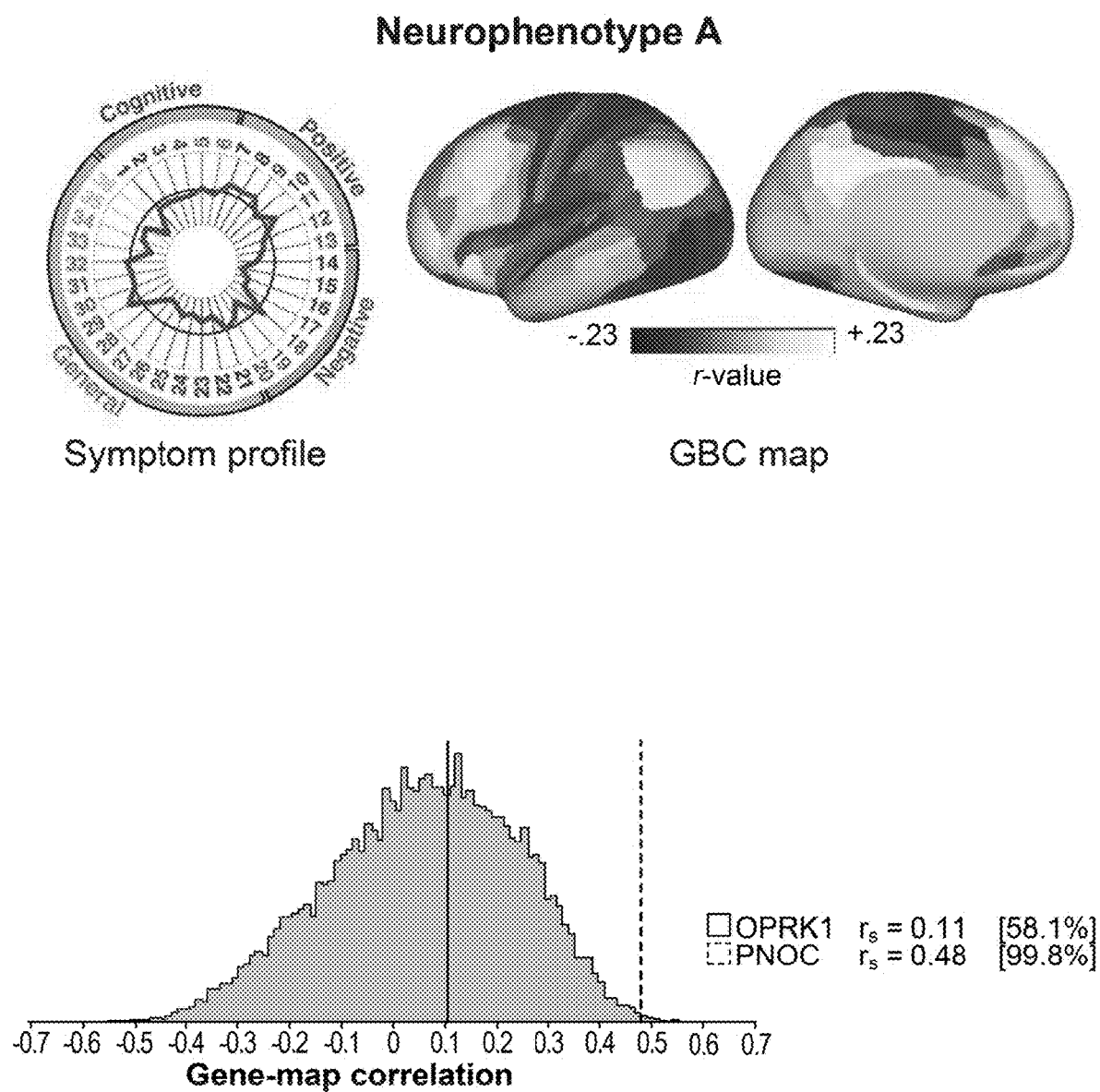
FIGS. 13A and 13B (left) shows the behavioral symptom profile and neural GBC map for two latent dimensions of individual variation and FIG. 13A and FIG. 13B (right) also shows the gene-map correlation scores for specific genes of interest.
Figure 13B:
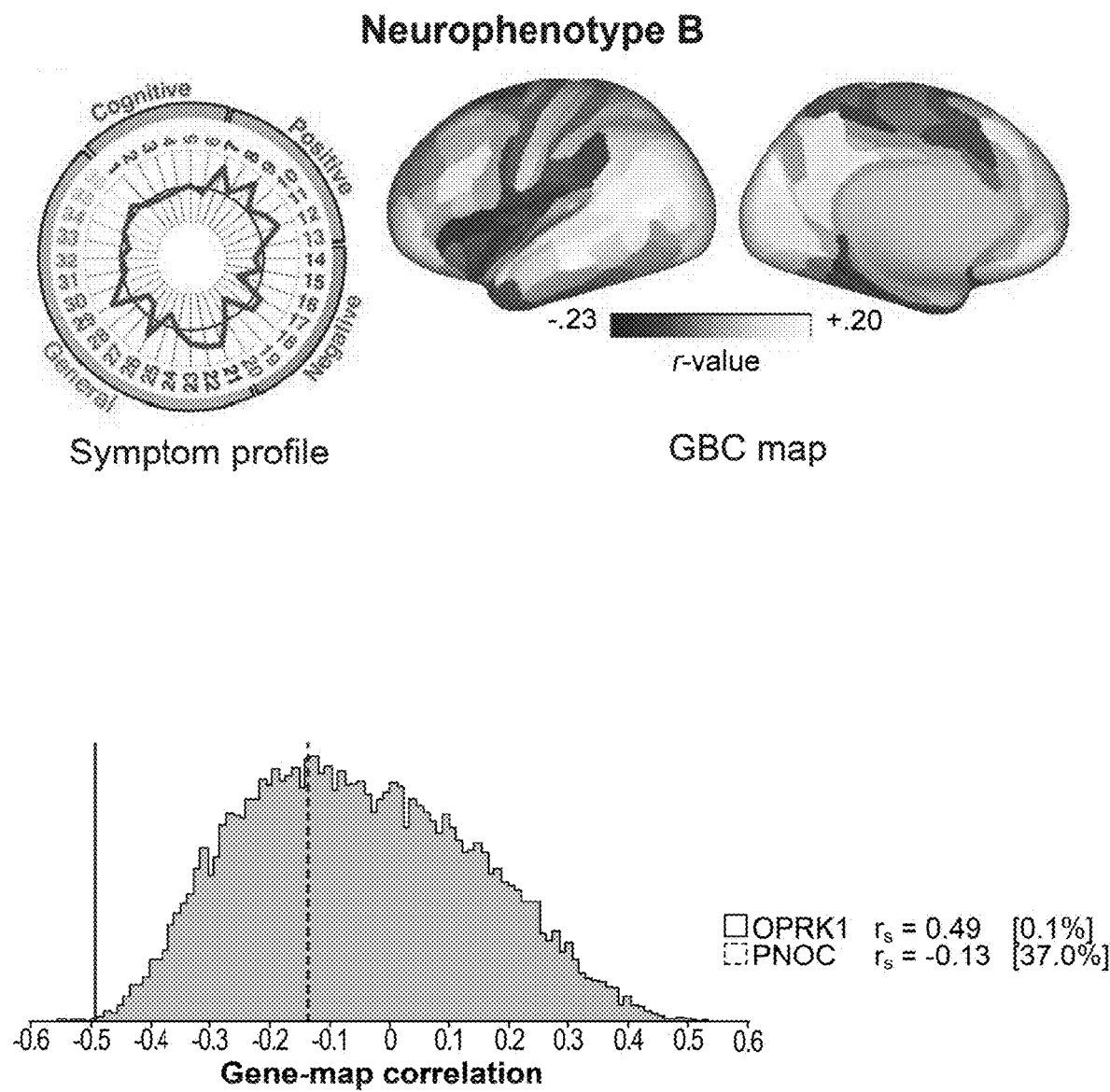

Example 7: Bi-Directional Identification of Drug Targets and Phenotypes in the BSNIP Dataset FIGS. 13A-13B show application of platform to show bi-directional identification of drug targets and phenotypes in the BSNIP dataset. The BSNIP (Bipolar-Schizophrenia Network for Intermediate Phenotypes) dataset includes resting-state fMRI data and symptom scores from a large number of subjects along a schizophrenia-bipolar continuum. Tamminga et al., *Bipolar and Schizophrenia Network for Intermediate Phenotypes: Outcomes Across the Psychosis Continuum*. SCHIZOPHR. BULL. 40:S131-S137 (2014) ("Tamminga"). Combined analysis of resting-state fMRI and behavioral symptom scores yielded multiple latent neuro-behavioral dimensions of individual variation, each of which characterizes both a behavioral symptom profile and a related brain map of individual differences in GBC. An individual with high GBC in the positive (light-colored) regions and low GBC in the negative (dark-colored) regions would score highly on symptoms associated with that latent dimension. FIG. 13A and FIG. 13B (top) shows the behavioral symptom profile and neural GBC map for two latent dimensions of individual variation. An individual patient may exhibit a neuro-behavioral phenotype similar to one specific latent dimension and not the other, or exhibit a mixture of the phenotypes.

The platform to these cortical phenotype maps. For each neurophenotype map, the gene-map correlation score was computed across all genes in the AHBA dataset, yielding a background distribution histogram shown in FIG. 13A and FIG. 13B (bottom). FIG. 13A and FIG. 13B (bottom) also shows the gene-map correlation scores for specific genes of interest. For the latent dimension shown in FIG. 13A (top), "Neurophenotype A," the score for the gene OPRK1 is near zero, indicating that the cortical expression topography of OPRK1 is uncorrelated with the neural map associated with that phenotype. In contrast, for the latent dimension shown in FIG. 13B (top), "Neurophenotype B," OPRK1 exhibits a strong negative correlation in the extreme 1% of all genes.

These results provide evidence that OPRK1 is a promising therapeutic target for the behavioral symptom profile provided by Neurophenotype B, due to overlap in the cortical topography. The Neurophenotype B symptom profile could therefore be used for patient segmentation in the design of a clinical trial for a kappa-opioid pharmaceutical. Pharmacological neuroimaging could provide further useful evidence by characterizing the impact on GBC by kappa-opioid modulation. This example demonstrates how operation of the platform can inform decision making in the context of the development and application of therapeutics.

Example 8: Gene to Phenotype Example Demonstrating Explanation of Negative Result and Repurposing of Therapeutic Agent for Different Phenotype The following example addresses the question of whether an H3 antagonist should be tested in CIAS. Here, the answer is "no" (r=0.04). Another follow-up question then is, for what phenotype would H3 inverse agonist be useful?

Figure 14A:
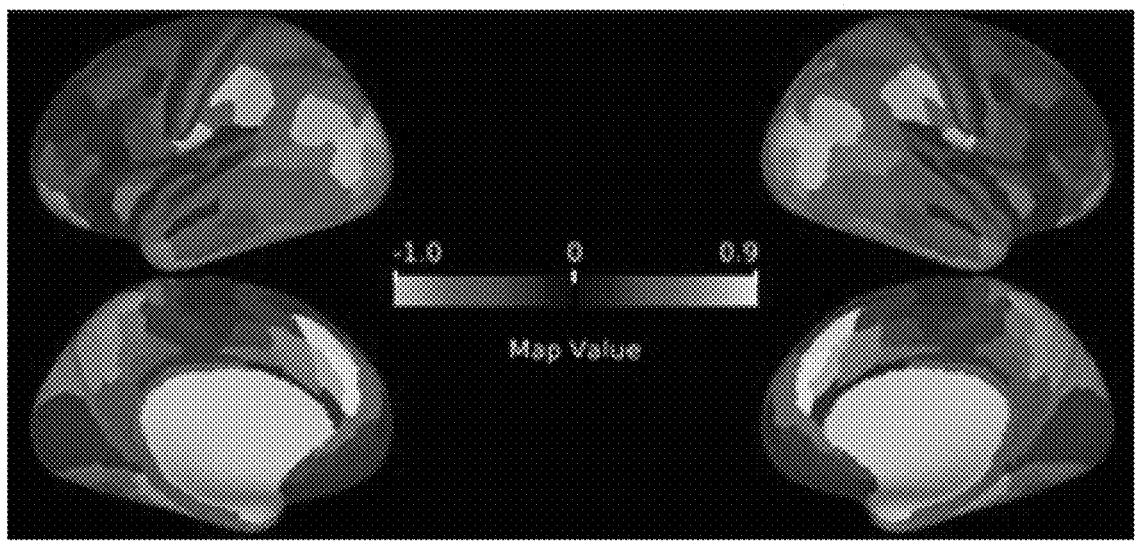
FIGS. 14A, 14B, and 14C provide images for a gene to phenotype example, wherein a negative results is explained and a drug is repurposed for a different neurobehavioral phenotype.
Figure 14B:
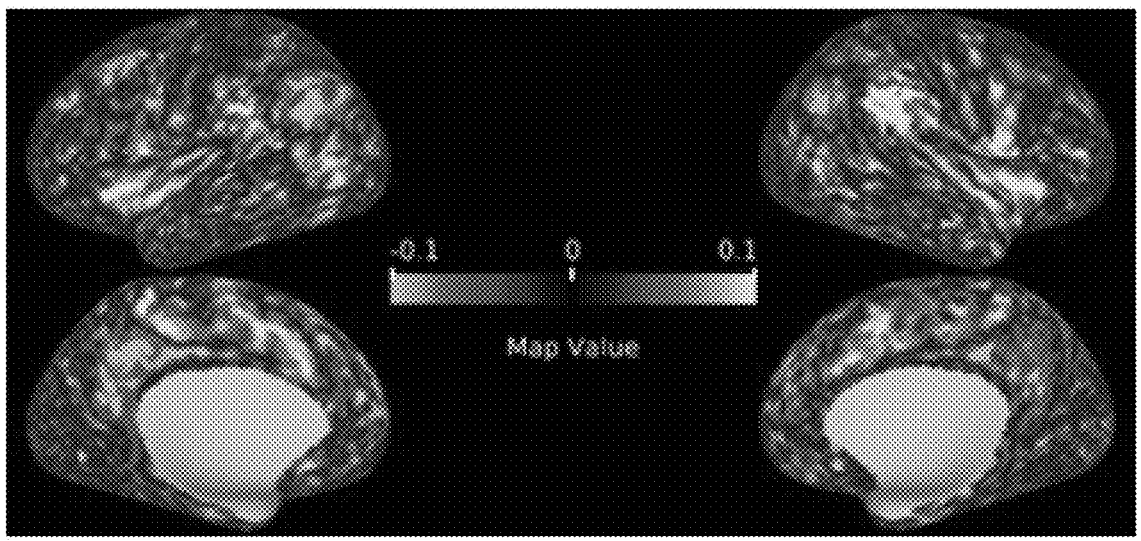
Figure 14C:
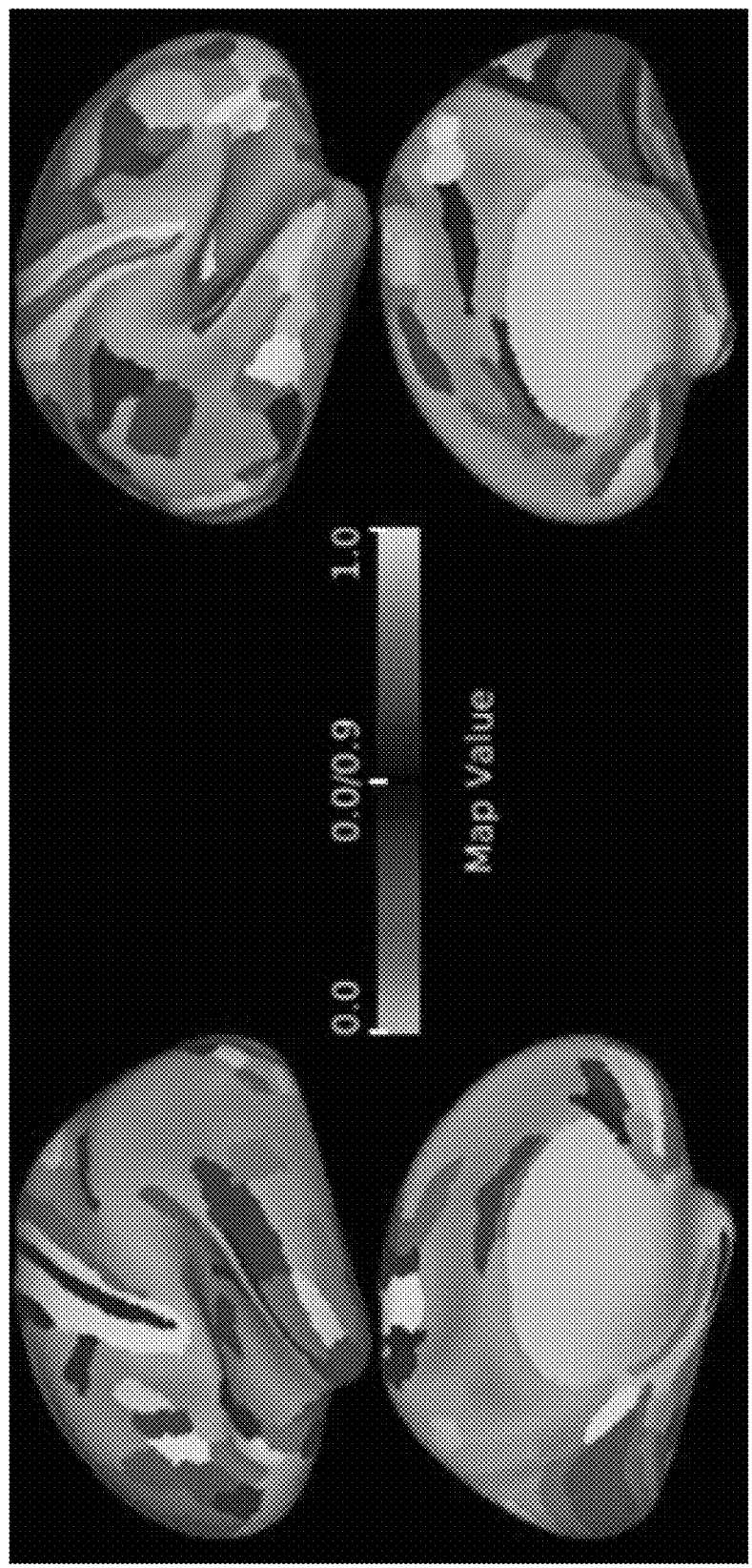

To support potential drug repurposing, one can examine the relationship between a gene and a phenotype. Here a gene map for gene HRH3 is provided in FIG. 14A, and a phenotype map for BSNIP Symptom Correlation GBCS Comp Correlation rZ is provided in FIG. 14B. The similarity score between a gene and a phenotype computes the correlation and associated p-value between two maps. Here, FIG. 14C shows the HRH3 gene and the phenotype map for BSNIP Symptom Correlation GBCS Comp Correlation rZ, wherein the cortex only was masked, as mapped for alignment. A correlation measure of 0.039666395207 was found.

Here, the expression pattern of the HRH3 gene, which encodes for the human histamine H3 receptor, was compared to the phenotype map associated derived from Global Brain Connectivity measures associated with the Brief Assessment of Cognition in Schizophrenia (BACS) Battery. There was very poor alignment between these two maps at the level of the cortex (Pearson's r=0.04). This result suggests that pharmacological intervention targeting the H3 receptor would not be expected to improve cognitive impairment associated with schizophrenia.

Indeed, Egan and colleagues showed that promoting histamine release with MK-0249 failed to improve cognitive deficits in patients with schizophrenia. Egan et al., *Randomized crossover study of the histamine H3 inverse agonist MK-0249 for the treatment of cognitive impairment in patients with schizophrenia*, SCHIZOPHR RES., 146(1-3): 224-30 May (2013); doi: 10.1016/j.schres.2013.02.030 (2013). However, H3 receptor expression was significantly correlated with whole-brain connectivity changes associated with questions that comprise the General subscale of the PANSS instrument (r=0.21; P<0.0001). This result suggests a potential benefit of H3 receptor modulation in patients with schizophrenia who present with symptoms indexed by the PANSS-General scale such as anxiety, depression, or poor attention.

Example 9: Gene to Gene Example (De Novo Therapeutic and Patient Selection)

The following example addresses the question of how to pursue disease modification within Parkinson's disease.

To support novel therapeutic intervention and patient selection in CNS disease, one can examine the relationship between a gene implicated in the disease and another gene that has not yet been implicated. The similarity score between two genes computes the correlation and associated p-value between two expression maps. Recent genetic findings in patients with Parkinson's disease (PD) led to the possibility of developing therapies against specific genotypes by targeting alpha-synuclein (SNCA), glucocerebrosidase (GBA), and leucine-rich repeat kinase (LRRK2). In addition to directly targeting the proteins encoded by these genes, evidence suggests other proteins can indirectly modulate these proteins to modify symptoms or disease progression in patients with PD.

For example, β2-adrenoreceptor (encoded by ADRB2) agonists may regulate alpha-synuclein. Mittal et al., *β2-Adrenoreceptor is a regulator of the α-synuclein gene driving risk of Parkinson's disease*, SCIENCE, 357(6354):891-898 (2017). And use of dopamine agonists acting via the D2 receptors (encoded by DRD2) may be beneficial in PD patients with LRRK2 mutations. Tozzi et al., *Dopamine D2 receptor activation potently inhibits striatal glutamatergic transmission in a G2019S LRRK2 genetic model of Parkin-* son's disease, NEUROBIOL DIS, 118: 1-8 (2018). The similarity scores between ADRB2 and SNCA (r=−0.16; P<0.0001) as well as DRD2 and LRRK1 (r=0.2; P<0.0001) are consistent with the published literature.

These observations may be extended using the tools and methods described herein to identify non-obvious genes that could alter symptoms and/or disease progression in PD patients. By comparing whole brain maps for the PNOC gene (which encodes the peptide N/OFQ) with maps for genes implicated in PD, one can predict the involvement of N/OFQ signaling in patients with SNCA (r=0.51; P<0.0001), LRRK2 (r=0.62; P<0.0001) and GBA (r=0.71; P<0.0001) mutations. This hypothesis can be tested preclinically by examining the effect of blocking N/OFQ signaling, via NOP receptors (NOPR) in alpha-synuclein-based models of PD and by testing NOPR antagonists in PD patients with these mutations. Moreover, this approach can be applied to identify novel drug targets that might regulated GBA activity such as those that modulate dipeptidyl-peptidase-like proteins (DPP10—GBA correlation: r=0.85; 99.3% similarity).

Example 10: Phenotype to Gene Example (Patient Screening Risks and Novel Therapeutic Intervention The following example addresses the question of which non-disease phenotypes can be associated with genes.

To identify patients who could be placed at higher risk with a therapeutic intervention or to guide the identification of novel therapeutics, we can examine the relationship between a particular phenotype and a gene or set of genes associated with the symptoms that comprise it.

For example, the antiretroviral drug efavirenz, which is effective in suppressing HIV-1, is known to increase the risk of neuropsychiatric symptoms. These neuropsychiatric adverse events have been attributed to the drug's interactions with multiple drug targets. Dalwadi et al., *Molecular mechanisms of serotonergic action of the HIV-1 antiretroviral efavirenz*, PHARMACOL RES., 110:10-24 (2016).

Figure 15A:
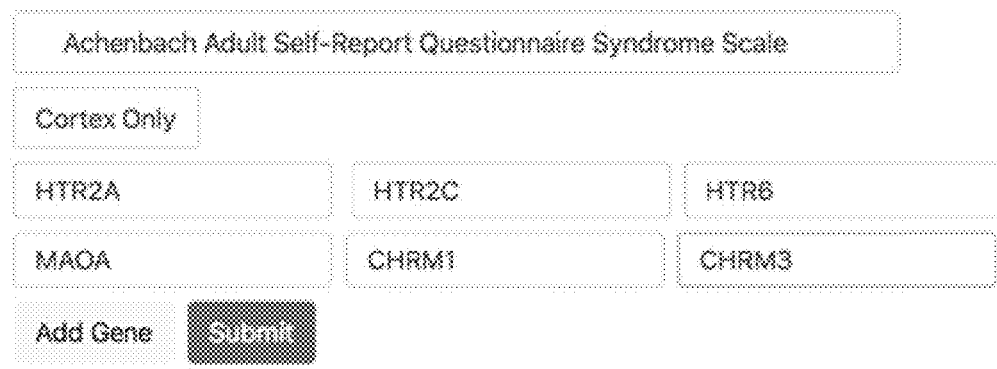
FIGS. 15A, 15B, 15C, 15D, 15E, 15F, and 15G provide images for a phenotype to gene example, wherein patient screening risks and novel therapeutic intervention are taken into account.
Figure 15B:
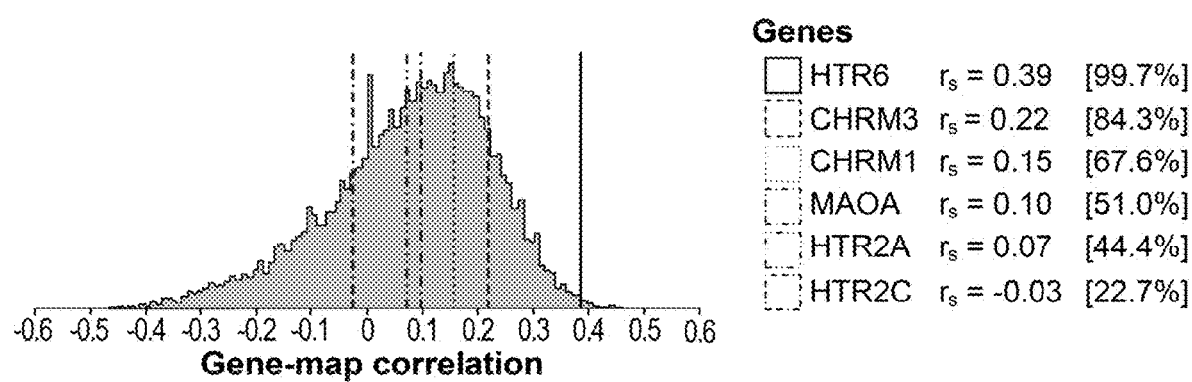
Figure 15C:
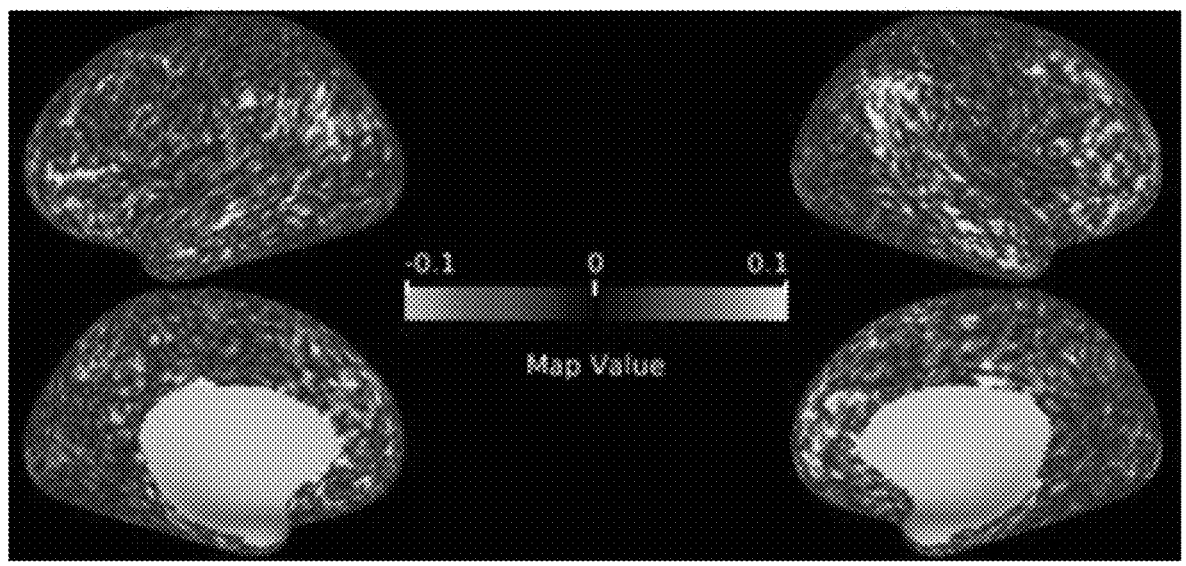

The Adult Self-Report (ASR) Syndrome Scale (SS) contains symptom-based scales that allows individuals to report on psychiatric symptoms such as depression, mood, anxiety, ADHD and psychotic behavior. By comparing responses on the ASR with resting-state brain connectivity measures, one can assess the relationship between behavioral variations along this scale with global brain connectivity (GBC). As shown in FIG. 15C, a phenotype map (HCP Cognitive Behavioral GBC ASR SS Correlation) the "hot spots" in red correspond to hyperconnected regions in individuals with high ASR scores.

Figure 15D:
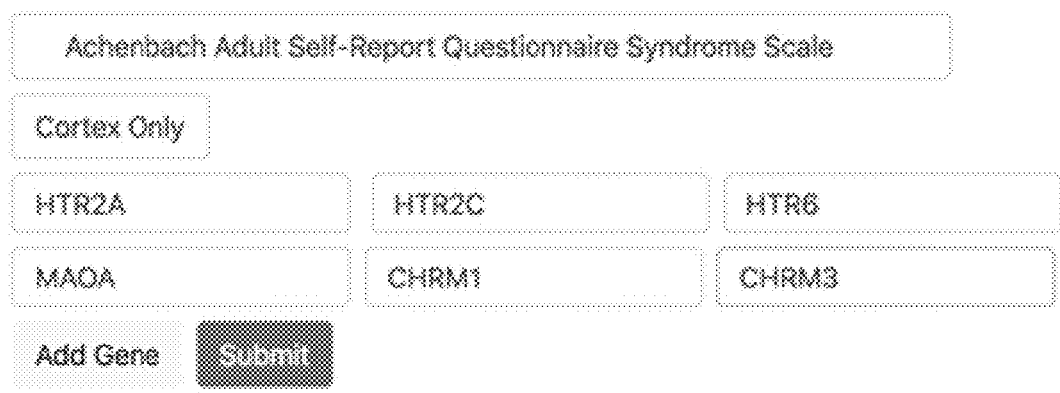
Figure 15E:
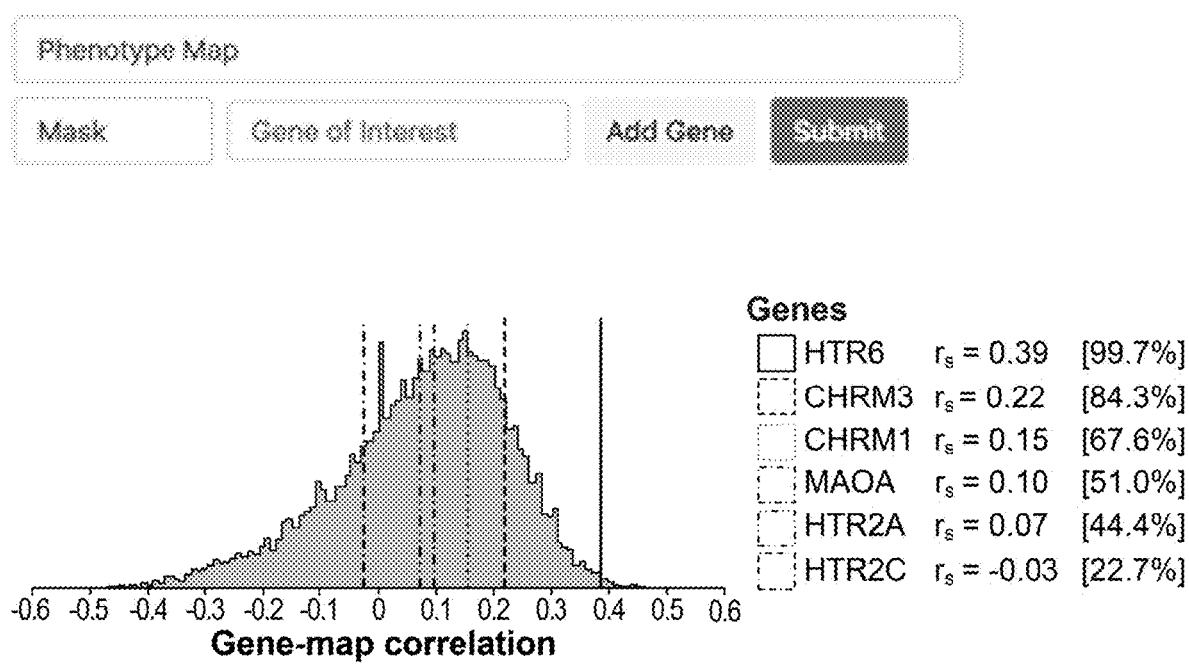

FIG. 15D shows a phenotype gene distribution chart. FIG. 15E shows a gene-map correlation for six (6) genes (HTR6, CHRM3, CHRM1, MAOA, HTR2A, and HTR2C).

Next, we build on reported observations to make new predictions about different drugs.

Next, one can examine the relationship between the ASR-SS GBC map and the molecular targets with which efavirenz interacts. The finding that HTR6 gene exhibits a high correlation with the ASR-SS GBC map (r=0.39, 99.7% similarity) is consistent with the published literature that suggests at least part of the psychiatric side effects associated with efavirenz can be attributed to the inverse agonist activity of the drug at 5HT6 receptors and antagonist activity at the muscarinic M3 (CHRM3) receptor.

Figures 15F, 15G:
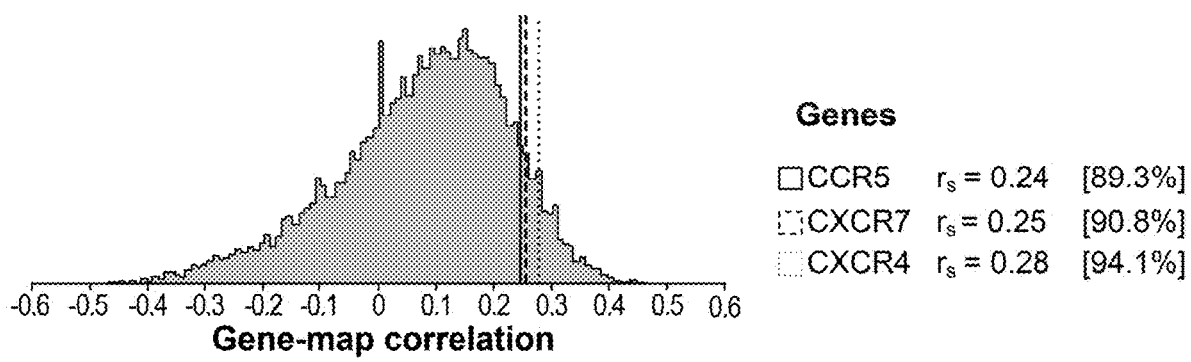

We extend this observation to assess whether individuals receiving different medicines to treat cancer or HIV infection could be at risk for psychiatric symptoms. FIG. 15F shows a phenotype gene distribution chart.

Two such drugs are plerixafor and maraviroc which target chemokine receptors, CXCR4 and CXCR (plerixafor) and CCR5 (maraviroc). An ASR-SS GBC phenotype by gene comparison revealed that these genes have statistically significant correlations with the psychiatric phenotype map (CCR5, r=0.24; CXCR7, r=0.25; CXCR4, r=0.28 with 94.1% similarity). These results are shown in FIG. 15G. These results suggest that individuals receiving plerixafor or maraviroc should be screened for psychiatric symptoms using the ASR-SS form.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A computing device, comprising:
a memory that stores computer instructions;
a processor that, when executing the computer instructions, performs actions to:
generate a neurophenotype topography for a selected neurobehavioral phenotype based on neurobehavioral phenotype mapping data for the selected neurobehavioral phenotype;
generate a genotype topography for each respective gene of a plurality of genes based on gene expression mapping data for the respective gene;
define a plurality of phenotype-gene pair topographies between the selected neurobehavioral phenotype and the plurality of genes, each phenotype-gene pair topography for each respective phenotype-gene pair being defined based on the neurophenotype topography of the selected neurobehavioral phenotype and the genotype topography of the respective gene for the respective phenotype-gene pair;
determine a quantitative score for each of the plurality of phenotype-gene pair topographies based on a correlation between the neurophenotype topography of the selected neurobehavioral phenotype and the genotype topography of the respective gene for the respective phenotype-gene pair;
select one or more of the plurality of phenotype-gene pair topographies having a respective score above a selected threshold; and
cause the respective genes of the selected one or more phenotype-gene pair topographies to be displayed on a display device for a user, the display device being configured to receive inputs from the user.

2. The computing device of claim 1, wherein the processor, when executing the computer instructions, further performs actions to identify one or more respective neural drug targets associated with the respective genes of the selected one or more phenotype-gene pair topographies.

3. The computing device of claim 1, wherein the processor generates the neurophenotype topography by executing further computer instructions to generate the neurophenotype topography from the neurobehavioral phenotype mapping data for each of a plurality of people having the selected neurobehavioral phenotype.

4. The computing device of claim 1, wherein the processor determines the score for each of the plurality of phenotype-gene pair topographies by executing further computer instructions to determine a statistical significance for each phenotype-gene pair topography based on an alignment between the gene expression mapping data for the respective gene with the neurobehavioral phenotype mapping data.

5. The computing device of claim 1, wherein the processor selects the one or more phenotype-gene pair topographies by executing further computer instructions to select a target phenotype-gene pair topography having a highest determined measure of association between the neurophenotype topography of the selected neurobehavioral phenotype and the genotype topography of the respective gene for the target phenotype-gene pair topography.

6. The computing device of claim 1, wherein the gene expression mapping data for each of the plurality of genes includes gene expression mapping data for a plurality of gene expressions from a plurality of people without the selected neurobehavioral phenotype.

7. The computing device of claim 6, wherein the processor generates the genotype topography for each respective gene by executing further computer instructions to select a representative probe for each of the plurality of genes across the plurality of gene expressions for the plurality of people.

8. The computing device of claim 1, wherein the processor generates the genotype topography for each respective gene by executing further computer instructions to map gene expression mapping samples to locations in brain structures, wherein causing the respective genes of the selected one or more phenotype-gene pair topographies to be displayed on the display device includes sending, to a second processor at the display device:
   the respective genes of the selected one or more phenotype-gene pair topographies; and
   one or more instructions to display a graphical representation of the respective genes on the display device.

9. The computing device of claim 1, wherein the processor generates the genotype topography for each respective gene by executing further computer instructions to filter gene expression mapping samples by excluding samples with measured expression levels below a threshold level above background signals.

10. The computing device of claim 1, wherein the processor generates the genotype topography for each respective gene by executing further computer instructions to impute probe values in gene expression mapping samples that are missing probe values.

11. The computing device of claim 1, wherein the processor generates the genotype topography for each respective gene by executing further computer instructions to remove extraneous biases from the gene expression mapping data.

12. The computing device of claim 11, wherein the processor removes the extraneous biases by executing further computer instructions to de-mean and normalize z-scores across gene probes used to capture the gene expression mapping data.

13. The computing device of claim 1, wherein the processor generates the genotype topography for each respective gene by executing further computer instructions to increase a signal-to-noise ratio in the gene expression mapping data.

14. The computing device of claim 13, wherein the processor increases the signal-to-noise ratio by executing further computer instructions to average expression levels of the gene expression mapping data for samples mapped onto a same surface vertex.

15. The computing device of claim 1, wherein the processor generates the genotype topography for each respective gene by executing further computer instructions to interpolate sparse gene expression samples from sampled brain regions to other non-sampled brain regions.

16. The computing device of claim 15, wherein the processor interpolates the sparse gene expression samples by executing further computer instructions to generate at least one of parcellated cortical or subcortical maps or a dense cortical or subcortical map.

17. The computing device of claim 1, wherein the processor generates the genotype topography for each respective gene by executing further computer instructions to assign a weight value for each of a plurality of brain regions in the gene expression mapping data.

18. The computing device of claim 1, wherein the processor generates the neurobehavioral topography by executing further computer instructions to assign a weight value for each of a plurality of brain regions in the neurobehavioral phenotype mapping data.

19. The computing device of claim 18, wherein the processor assigns the weight value for each of the plurality of brain regions by executing further computer instructions to:
   assign a first set of weight values above a threshold value for a first set of brain regions of the plurality of brain regions in the neurobehavioral phenotype mapping data; and
   assign a second set of weight values below the threshold value for a second set of brain regions of the plurality of brain regions in the neurobehavioral phenotype mapping data.

20. The computing device of claim 18, wherein the processor assigns the weight value for each of the plurality of brain regions by executing further computer instructions to assign a masking weight value to a target brain region of the plurality of brain regions to remove information associated with the target brain region from the neurobehavioral phenotype mapping data.

21. The computing device of claim 1, wherein the processor defines the plurality of phenotype-gene pair topographies by executing further computer instructions to define at least one combination phenotype-gene pair topography between the neurobehavioral phenotype topography and a combination of genotype topographies for a combination of genes.

22. The computing device of claim 21, wherein the processor, when executing the computer instructions, further performs actions to:
   select the at least one combination phenotype-gene pair topography as the one or more of the plurality of phenotype-gene pair topographies having the respective score above the selected threshold; and
   display the combination of genes to the user.

23. The computing device of claim 1, wherein the processor, when executing the computer instructions, further performs actions to:
   identify combinations of genes or neural drug targets by combining gene expression mapping data that exhibits improved alignment with the neurobehavioral phenotype mapping data relative to the alignment of gene expression mapping data and neurobehavioral phenotype mapping data for each separate gene or neural drug target.

24. The computing device of claim 1, wherein the display device is a touch sensitive screen.

25. A method, comprising:
- obtaining, by a computing device, neurobehavioral phenotype mapping data for a selected neurobehavioral phenotype;
- generate a neurophenotype topography for the selected neurobehavioral phenotype based on the neurobehavioral phenotype mapping data for the selected neurobehavioral phenotype;
- obtaining, by the computing device, gene expression mapping data for a plurality of genes;
- generate a genotype topography for each respective gene of the plurality of genes based on the gene expression mapping data for the respective gene;
- determining, by the computing device, a quantitative score for each respective phenotype-gene pair between the selected neurobehavioral phenotype and a respective gene of the plurality of genes based on a correlation between the neurobehavioral phenotype mapping data for the selected neurobehavioral phenotype and the gene expression mapping data for the respective gene of the respective phonotype-gene pair; and
- causing, by the computing device, the determined score for each phenotype-gene pair to be presented to a user on a display device, the display device being configured to receive inputs from the user.

* * * * *